US012685636B2

(12) United States Patent
Fine et al.

(10) Patent No.: US 12,685,636 B2
(45) Date of Patent: Jul. 21, 2026

(54) EXPANDABLE SHEATH FOR INTRODUCING AN ENDOVASCULAR DELIVERY DEVICE INTO A BODY

(71) Applicant: Edwards Lifesciences Corporation, Irvine, CA (US)

(72) Inventors: Maxwell Harrison Fine, Costa Mesa, CA (US); Ilan Tamir, Irvine, CA (US); Jeong Soo Lee, Diamond Bar, CA (US); Sonny Tran, Westminster, CA (US); Leah Paige Gaffney, Orange, CA (US); Erik Bulman, Lake Forest, CA (US); Nasser William Saleh, Stockton, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 919 days.

(21) Appl. No.: 17/981,395

(22) Filed: Nov. 5, 2022

(65) Prior Publication Data

US 2023/0056245 A1 Feb. 23, 2023

Related U.S. Application Data

(63) Continuation of application No. PCT/US2021/031227, filed on May 7, 2021.
(Continued)

(51) Int. Cl.
*A61F 2/24* (2006.01)
*A61M 25/00* (2006.01)
*A61M 25/06* (2006.01)

(52) U.S. Cl.
CPC ... *A61F 2/2436* (2013.01); *A61M 2025/0006* (2013.01); *A61M 2025/0024* (2013.01); *A61M 2025/0681* (2013.01)

(58) Field of Classification Search
CPC .... A61F 2/2436; A61F 2/2427; A61F 2/2418; A61F 2/2433; A61F 2/011; A61M 25/1038
See application file for complete search history.

(56) References Cited

U.S. PATENT DOCUMENTS

| 4,601,713 | A | 7/1986 | Fuqua |
| 4,710,181 | A | 12/1987 | Fuqua |
| | | (Continued) | |

FOREIGN PATENT DOCUMENTS

| EP | 0103546 B1 | 5/1988 |
| EP | 0592410 B1 | 10/1995 |
| | (Continued) | |

*Primary Examiner* — Brian A Dukert
(74) *Attorney, Agent, or Firm* — Meunier Carlin Curfman LLC

(57) ABSTRACT

Examples of an expandable sheath can be used in conjunction with a catheter assembly to introduce a prosthetic device, such as a heart valve, into a patient. Such examples can minimize trauma to the vessel by allowing for temporary expansion of a portion of the introducer sheath to accommodate the delivery apparatus, followed by a return to the original diameter once the prosthetic device passes through. Some examples can include a sheath with inner and outer layers, where a folded portion of the inner layer extends through a slit in the outer layer and a portion of the outer layer overlaps the folded portion of the inner layer. Some examples include an elastic outer cover positioned outside the outer layer. Examples of the present expandable sheath can avoid the need for multiple insertions for the dilation of the vessel, thus offering advantages over prior art introducer sheaths.

19 Claims, 41 Drawing Sheets

Related U.S. Application Data

(60) Provisional application No. 63/021,945, filed on May 8, 2020.

(56) References Cited

U.S. PATENT DOCUMENTS

| | | | |
|---|---|---|---|
| 4,738,666 A | 4/1988 | Fuqua | |
| 4,921,479 A | 5/1990 | Grayzel | |
| 5,104,388 A | 4/1992 | Quackenbush | |
| 5,318,588 A | 6/1994 | Horzewski et al. | |
| 5,320,611 A | 6/1994 | Bonutti et al. | |
| 5,501,667 A | 3/1996 | Verduin | |
| 5,674,240 A | 10/1997 | Bonutti et al. | |
| 5,810,776 A | 9/1998 | Bacich et al. | |
| 5,817,100 A | 10/1998 | Igaki | |
| 5,882,345 A | 3/1999 | Yoon | |
| 5,997,508 A | 12/1999 | Lunn et al. | |
| 6,080,141 A | 6/2000 | Castro et al. | |
| 6,090,072 A | 7/2000 | Kratoska et al. | |
| 6,090,136 A | 7/2000 | McDonald et al. | |
| 6,190,357 B1 | 2/2001 | Ferrari et al. | |
| 6,312,443 B1 | 11/2001 | Stone | |
| 6,346,092 B1 | 2/2002 | Leschinsky | |
| 6,358,238 B1 | 3/2002 | Sherry | |
| 6,443,979 B1 | 9/2002 | Stalker et al. | |
| 6,494,860 B2 | 12/2002 | Rocamora et al. | |
| 6,632,236 B2 | 10/2003 | Hogendijk | |
| 6,652,492 B1 | 11/2003 | Bell et al. | |
| 6,814,715 B2 | 11/2004 | Bonutti et al. | |
| 6,899,727 B2 | 5/2005 | Armstrong et al. | |
| 7,438,712 B2 | 10/2008 | Chouinard | |
| 7,591,832 B2 | 9/2009 | Eversull et al. | |
| 7,655,016 B2 | 2/2010 | Demarais et al. | |
| 7,678,128 B2 | 3/2010 | Boyle et al. | |
| 7,713,193 B2 | 5/2010 | Nance et al. | |
| 7,762,995 B2 | 7/2010 | Eversull et al. | |
| 7,766,820 B2 | 8/2010 | Core | |
| 7,780,692 B2 | 8/2010 | Nance et al. | |
| 7,785,360 B2 | 8/2010 | Freitag | |
| 7,837,692 B2 | 11/2010 | Mulholland et al. | |
| 7,892,203 B2 | 2/2011 | Lenker et al. | |
| 7,927,309 B2 | 4/2011 | Palm | |
| 7,963,952 B2 | 6/2011 | Wright et al. | |
| 8,034,072 B2 | 10/2011 | Nguyen et al. | |
| 8,048,034 B2 | 11/2011 | Eversull et al. | |
| 8,090,936 B2 | 1/2012 | Fallon et al. | |
| 8,092,481 B2 | 1/2012 | Nance et al. | |
| 8,252,015 B2 | 8/2012 | Leeflang et al. | |
| 8,282,664 B2 | 10/2012 | Nance et al. | |
| 8,414,645 B2 | 4/2013 | Dwork et al. | |
| 8,562,559 B2 | 10/2013 | Bishop et al. | |
| 8,562,673 B2 | 10/2013 | Yeung et al. | |
| 8,652,203 B2 | 2/2014 | Quadri et al. | |
| 8,668,668 B2 | 3/2014 | Bishop et al. | |
| 8,690,936 B2 | 4/2014 | Nguyen et al. | |
| 8,790,387 B2 * | 7/2014 | Nguyen | A61F 2/2433 |
| | | | 604/525 |
| 9,044,577 B2 | 6/2015 | Bishop et al. | |
| 9,192,751 B2 | 11/2015 | Macaulay et al. | |
| 9,192,752 B2 | 11/2015 | Leeflang et al. | |
| 9,254,374 B2 | 2/2016 | Thorstenson et al. | |
| 9,259,813 B2 | 2/2016 | Heideman et al. | |
| 9,301,840 B2 | 4/2016 | Nguyen et al. | |
| 9,301,841 B2 | 4/2016 | Nguyen et al. | |
| 9,320,508 B2 | 4/2016 | Carroux | |
| 9,393,041 B2 | 7/2016 | Barker et al. | |
| 9,642,704 B2 | 5/2017 | Tuval et al. | |
| 9,788,944 B2 | 10/2017 | Daly et al. | |
| 9,907,931 B2 | 3/2018 | Birmingham et al. | |
| 10,327,896 B2 | 6/2019 | Zhou et al. | |
| 10,639,152 B2 | 5/2020 | Le et al. | |
| 10,792,471 B2 | 10/2020 | Zhou et al. | |
| 10,912,919 B2 | 2/2021 | Bulman et al. | |
| 11,344,698 B2 | 5/2022 | Worthley et al. | |
| 2001/0012950 A1 | 8/2001 | Nishtala et al. | |
| 2002/0032459 A1 | 3/2002 | Horzewski et al. | |
| 2002/0099431 A1 | 7/2002 | Armstrong et al. | |
| 2002/0123793 A1 | 9/2002 | Schaldach et al. | |
| 2002/0128702 A1 | 9/2002 | Menz et al. | |
| 2002/0173785 A1 | 11/2002 | Spear et al. | |
| 2003/0004537 A1 | 1/2003 | Boyle et al. | |
| 2004/0087968 A1 | 5/2004 | Core | |
| 2004/0122415 A1 | 6/2004 | Johnson | |
| 2005/0080430 A1 | 4/2005 | Wright et al. | |
| 2005/0085842 A1 | 4/2005 | Eversull et al. | |
| 2005/0125021 A1 | 6/2005 | Nance et al. | |
| 2006/0020321 A1 | 1/2006 | Parker | |
| 2006/0135962 A1 | 6/2006 | Kick et al. | |
| 2006/0135981 A1 | 6/2006 | Lenker et al. | |
| 2006/0217755 A1 | 9/2006 | Eversull et al. | |
| 2007/0021768 A1 | 1/2007 | Nance et al. | |
| 2007/0074805 A1 | 4/2007 | Leeflang et al. | |
| 2007/0087148 A1 | 4/2007 | Okushi et al. | |
| 2008/0004521 A1 | 1/2008 | Hundley et al. | |
| 2008/0004571 A1 | 1/2008 | Voss | |
| 2008/0082120 A1 | 4/2008 | Mauch et al. | |
| 2008/0114331 A1 | 5/2008 | Holman et al. | |
| 2008/0243081 A1 | 10/2008 | Nance et al. | |
| 2009/0182411 A1 | 7/2009 | Irwin et al. | |
| 2009/0287182 A1 | 11/2009 | Bishop et al. | |
| 2010/0094209 A1 | 4/2010 | Drasler et al. | |
| 2010/0094392 A1 | 4/2010 | Nguyen et al. | |
| 2010/0198160 A1 | 8/2010 | Voss | |
| 2010/0324490 A1 | 12/2010 | Pini et al. | |
| 2011/0112567 A1 | 5/2011 | Lenker et al. | |
| 2011/0190697 A1 | 8/2011 | Farnan | |
| 2011/0251681 A1 | 10/2011 | Shipley et al. | |
| 2012/0083877 A1 | 4/2012 | Nguyen et al. | |
| 2012/0116439 A1 | 5/2012 | Ho | |
| 2012/0158033 A1 | 6/2012 | Deal et al. | |
| 2012/0323180 A1 | 12/2012 | Chebator et al. | |
| 2013/0090624 A1 | 4/2013 | Munsinger | |
| 2013/0131718 A1 | 5/2013 | Jenson et al. | |
| 2013/0178711 A1 | 7/2013 | Avneri et al. | |
| 2013/0211324 A1 | 8/2013 | Voss et al. | |
| 2013/0231735 A1 | 9/2013 | Deem et al. | |
| 2013/0268064 A1 | 10/2013 | Duffy | |
| 2013/0281787 A1 | 10/2013 | Avneri et al. | |
| 2014/0012281 A1 | 1/2014 | Wang et al. | |
| 2014/0121629 A1 | 5/2014 | Macaulay et al. | |
| 2014/0142509 A1 | 5/2014 | Bonutti et al. | |
| 2014/0236122 A1 | 8/2014 | Anderson et al. | |
| 2014/0236123 A1 | 8/2014 | Birmingham et al. | |
| 2014/0379067 A1 | 12/2014 | Nguyen et al. | |
| 2015/0112428 A1 | 4/2015 | Daly et al. | |
| 2015/0182723 A1 | 7/2015 | Leeflang et al. | |
| 2015/0238178 A1 | 8/2015 | Carroux | |
| 2015/0265798 A1 | 9/2015 | Nihonmatsu et al. | |
| 2015/0320971 A1 | 11/2015 | Leeflang et al. | |
| 2016/0074067 A1 | 3/2016 | Furnish et al. | |
| 2016/0135840 A1 | 5/2016 | Kick et al. | |
| 2016/0213882 A1 | 7/2016 | Fitterer et al. | |
| 2016/0296332 A1 | 10/2016 | Zhou et al. | |
| 2016/0296730 A1 | 10/2016 | Zhou et al. | |
| 2017/0014157 A1 | 1/2017 | Coyle et al. | |
| 2017/0072163 A1 | 3/2017 | Lim et al. | |
| 2017/0196690 A1 | 7/2017 | Racchini et al. | |
| 2017/0209133 A1 | 7/2017 | Ciulla et al. | |
| 2017/0245864 A1 | 8/2017 | Franano et al. | |
| 2017/0252062 A1 | 9/2017 | Fitterer et al. | |
| 2018/0043133 A1 | 2/2018 | Wong | |
| 2018/0161064 A1 | 6/2018 | Fitterer et al. | |
| 2018/0199960 A1 | 7/2018 | Anderson et al. | |
| 2018/0207395 A1 | 7/2018 | Bulman et al. | |
| 2018/0229000 A1 | 8/2018 | Anderson et al. | |
| 2018/0256858 A1 | 9/2018 | Zhou et al. | |
| 2018/0325549 A1 | 11/2018 | Thoreson et al. | |
| 2019/0029824 A1 | 1/2019 | Nguyen et al. | |
| 2019/0076167 A1 | 3/2019 | Fantuzzi et al. | |
| 2019/0083082 A1 | 3/2019 | Tassoni, Jr. et al. | |
| 2019/0192290 A1 | 6/2019 | Pfenniger et al. | |
| 2019/0247627 A1 | 8/2019 | Korkuch et al. | |
| 2019/0269510 A1 | 9/2019 | Zeng et al. | |
| 2020/0078571 A1 | 3/2020 | Kirt et al. | |

(56) References Cited

U.S. PATENT DOCUMENTS

| | | |
|---|---|---|
| 2021/0008344 A1 | 1/2021 | Chen et al. |
| 2021/0236783 A1 | 8/2021 | Korkuch et al. |
| 2022/0032015 A1 | 2/2022 | Campbell et al. |
| 2022/0346950 A1 | 11/2022 | Le et al. |
| 2023/0029387 A1 | 1/2023 | Yadav et al. |
| 2023/0069245 A1 | 3/2023 | Tran et al. |
| 2023/0149674 A1 | 5/2023 | Neumann et al. |
| 2023/0381455 A1 | 11/2023 | Fantuzzi et al. |
| 2024/0091038 A1 | 3/2024 | Acharya |
| 2024/0299722 A1 | 9/2024 | Ruiz et al. |
| 2025/0001139 A1 | 1/2025 | Farrell et al. |
| 2025/0144367 A1 | 5/2025 | Anderson et al. |
| 2025/0249213 A1 | 8/2025 | Belcher et al. |
| 2025/0276153 A1 | 9/2025 | Moran et al. |
| 2025/0276155 A1 | 9/2025 | Moran et al. |
| 2025/0367411 A1 | 12/2025 | Mak et al. |

FOREIGN PATENT DOCUMENTS

| | | | |
|---|---|---|---|
| EP | 1139889 | B1 | 4/2006 |
| EP | 1804860 | B1 | 4/2014 |
| EP | 2288403 | B1 | 11/2014 |
| EP | 1694398 | B1 | 3/2016 |
| EP | 2101661 | B1 | 3/2016 |
| EP | 2995268 | A1 | 3/2016 |
| EP | 2475417 | B1 | 10/2018 |
| EP | 2911729 | B1 | 12/2018 |
| EP | 2862590 | B1 | 2/2019 |
| EP | 1793881 | B1 | 4/2020 |
| JP | 2012040145 | A | 3/2012 |
| JP | 2013526899 | A | 6/2013 |
| WO | 2004037333 | A1 | 5/2004 |
| WO | 2008147964 | A1 | 12/2008 |
| WO | 2009035745 | A1 | 3/2009 |
| WO | 2013044942 | A1 | 4/2013 |
| WO | 2014140093 | A1 | 9/2014 |
| WO | WO-2015063497 | A1 | 5/2015 |
| WO | 2018148488 | A1 | 8/2018 |
| WO | WO-2019199692 | A1 | 10/2019 |
| WO | 2022026026 | A1 | 2/2022 |
| WO | WO-2024205785 | A1 | 10/2024 |
| WO | WO-2024226928 | A1 | 10/2024 |
| WO | WO-2024263844 | A1 | 12/2024 |
| WO | WO-2025029777 | A1 | 2/2025 |
| WO | WO-2025048911 | A1 | 3/2025 |

* cited by examiner

28

28

28

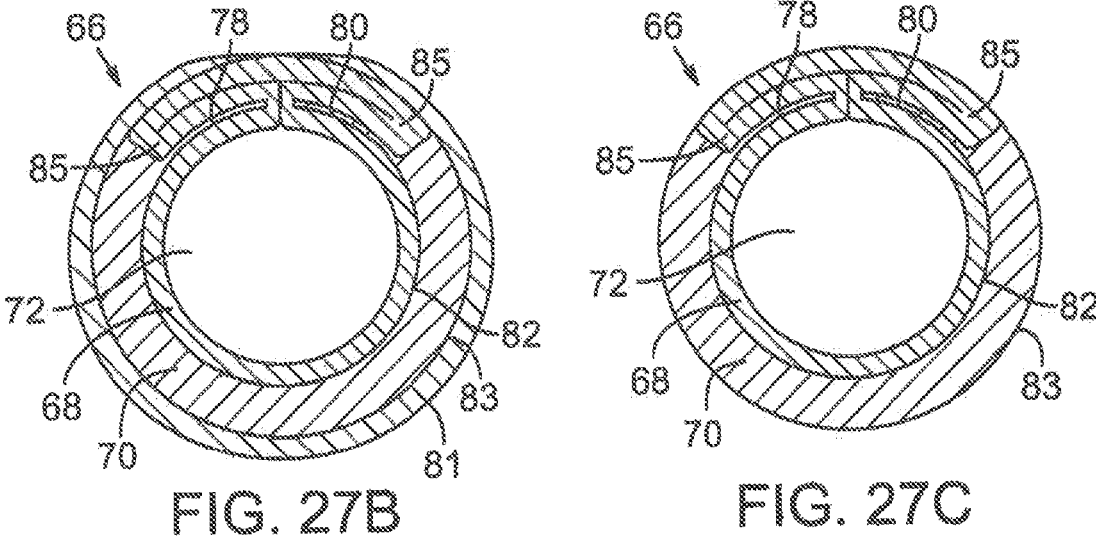
FIG. 27B          FIG. 27C
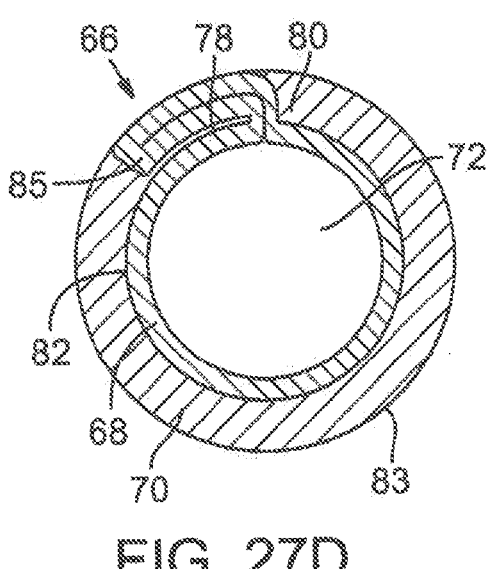 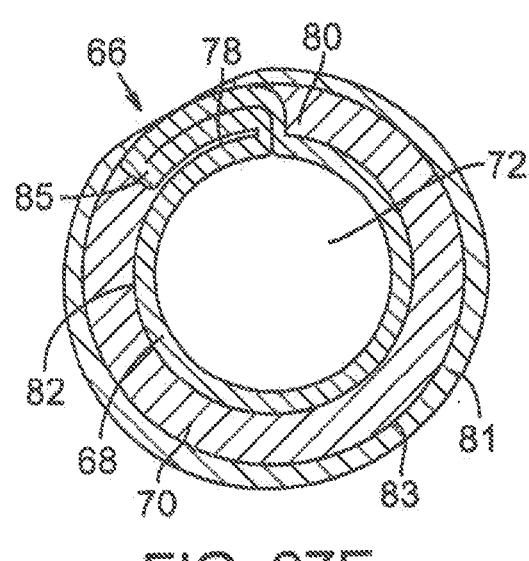
FIG. 27D          FIG. 27E

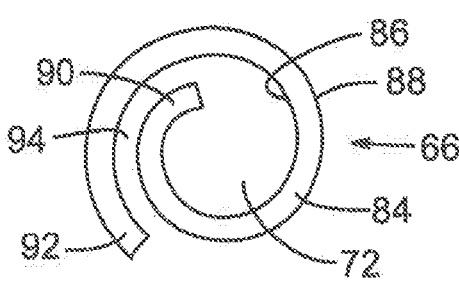
FIG. 29A
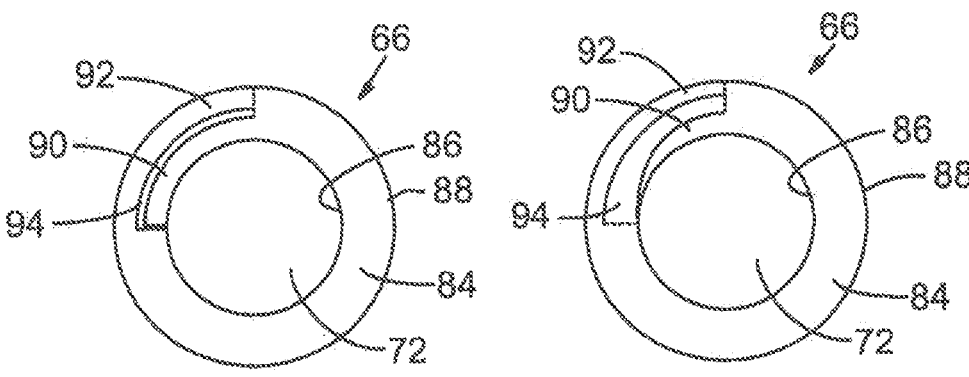
FIG. 29B                    FIG. 29C
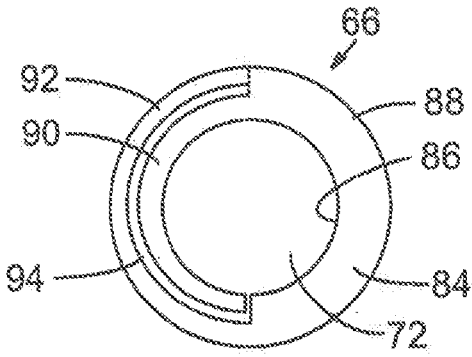
FIG. 29D FIG. 32F
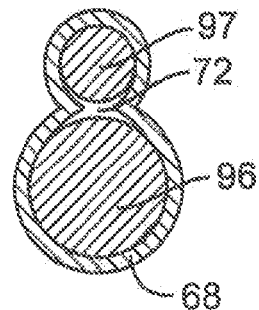
FIG. 32G
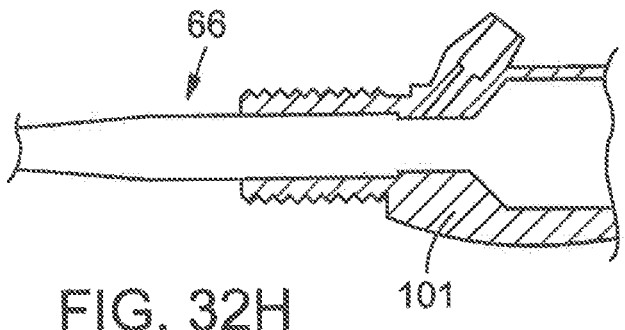
FIG. 32H

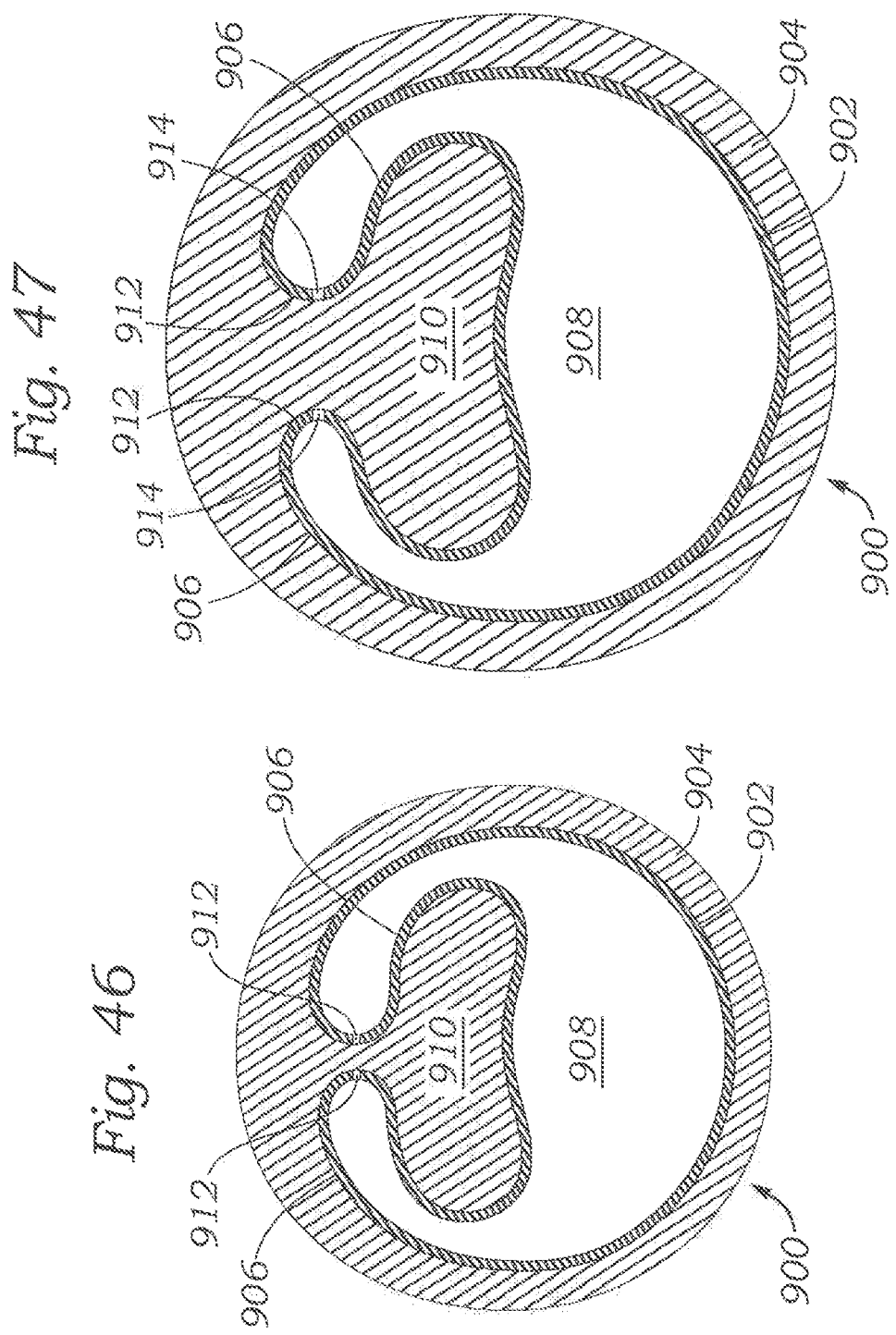

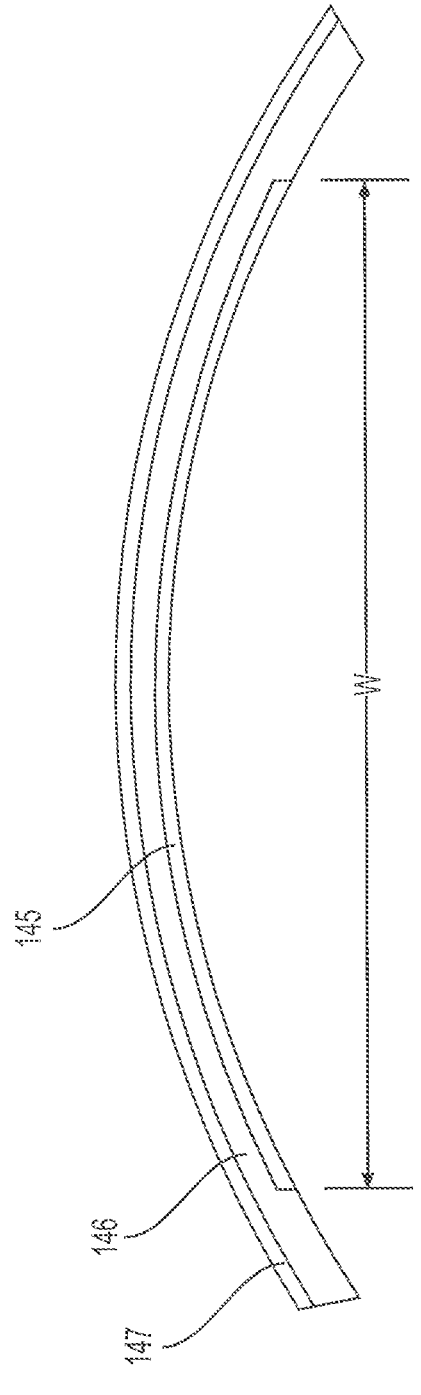
*FIG. 65*

EXPANDABLE SHEATH FOR INTRODUCING AN ENDOVASCULAR DELIVERY DEVICE INTO A BODY

CROSS-REFERENCE TO RELATED APPLICATIONS

This application is a continuation of International Application No. PCT/US2021/031227, filed May 7, 2021, which claims the benefit of U.S. Provisional Application No. 63/021,945, filed May 8, 2020, where each of above-referenced applications is incorporated herein by reference in its entirety.

FIELD

The present application concerns examples of a sheath for use with catheter-based technologies for repairing and/or replacing heart valves, as well as for delivering a prosthetic device, such as a prosthetic valve to a heart via the patient's vasculature.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths have been disclosed. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a significant risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque.

Accordingly, there remains a need in the art for an improved introducer sheath for endovascular systems used for implanting valves and other prosthetic devices.

SUMMARY

Examples of the present expandable sheath can minimize trauma to the vessel by allowing for temporary expansion of a portion of the introducer sheath to accommodate a delivery system, followed by a return to the original diameter once the delivery system passes through. Some examples can comprise a sheath with a smaller profile than that of prior art introducer sheaths. Furthermore, certain examples can reduce the length of time a procedure takes, as well as reduce the risk of a longitudinal or radial vessel tear, or plaque dislodgement because only one sheath is required, rather than several different sizes of sheaths. Examples of the present expandable sheath can require only a single vessel insertion, as opposed to requiring multiple insertions for the dilation of the vessel.

One example of a sheath for introducing a prosthetic device comprises an inner layer and an outer layer. At least a portion of the sheath can be designed or configured to locally expand from a first diameter to a second diameter as the prosthetic device is pushed through a lumen of the sheath, and then at least partially return to the first diameter once the prosthetic device has passed through. Some examples can additionally include an elastic outer cover disposed about the outer layer.

The inner layer can comprise polytetrafluoroethylene (PTFE), polyimide, polyetheretherketone (PEEK), polyurethane, nylon, polyethylene, polyamide, or combinations thereof. The outer layer can comprise PTFE, polyimide, PEEK, polyurethane, nylon, polyethylene, polypropylene, polyamide, polyether block amides, polyether block ester copolymer, thermoset silicone, latex, poly-isoprene rubbers, high density polyethylene (HDPE), Tecoflex™, or combinations thereof. In one example, the inner layer can comprise PTFE and the outer layer can comprise a combination of HDPE and Tecoflex™. If present, the elastic outer cover can include any suitable materials, such as any suitable heat shrink materials. Examples include Pebax, polyurethane, silicone, and/or polyisoprene.

Disclosed examples of a sheath comprise a proximal end and a distal end opposite one another. Some examples can include a hemostasis valve at or near the proximal end of the sheath. In some examples, the outer diameter of the sheath decreases along a gradient from the proximal end to the distal end of the sheath. In other examples, the outer diameter of the sheath is substantially constant along at least a majority of the length of the sheath.

One example of a sheath for introducing a prosthetic device into a body can comprise a continuous inner layer defining a lumen therethrough, the inner layer having a folded portion and a discontinuous outer layer having an overlapping portion and an underlying portion. In some examples, the inner layer can have at least two folded portions. The outer layer can be configured so that the overlapping portion overlaps the underlying portion, wherein at least a portion of the folded portion of the inner tubular layer is positioned between the overlapping and underlying portions. At least a portion of the sheath is configured to expand to accommodate the prosthetic device.

In some examples, at least a portion of the sheath is configured such that a plurality of segments of the sheath each locally expands one at a time from a rest configuration having a first diameter to an expanded configuration having a second diameter that is larger than the first diameter to facilitate passage of the prosthetic device through the lumen of the inner layer. Each segment can have a length defined along the longitudinal axis of the sheath, and each segment of the sheath can be configured to at least partially return to the first diameter once the prosthetic device has passed through. In some examples, when each segment of the sheath is in the expanded configuration, a length of the folded portion corresponding to the length of the segment at least partially unfolds (e.g., by separating and/or straightening). A length of the overlapping portion corresponding to the length of the segment can be configured to move with respect to the underlying portion when each segment of the sheath expands from the rest configuration to the expanded configuration.

In one specific example, the inner layer comprises PTFE and the outer layer comprises HDPE and/or Tecoflex™. The inner and outer layers can be thermally fused together in some examples. In some examples, the inner layer comprises a woven fabric and/or braided filaments such as yarn filaments of PTFE, PET, PEEK, and/or nylon.

Some disclosed expandable sheaths can further include an elastic outer cover disposed on an external surface of the outer layer. The elastic outer cover can comprise, for example, heat shrink tubing. Some sheaths include one or more radiopaque marker or fillers, such as a C-shaped band positioned between the inner and outer layers near the distal end of the sheath. Some examples include a soft tip secured to the distal end of the sheath.

In some examples, the inner layer can include at least one folded portion and at least one weakened portion. A discontinuous outer layer can have an outer surface and an inner surface and a longitudinal gap, and a portion of the inner layer can extend through the longitudinal gap. The at least one folded portion of the inner layer can be positioned adjacent a portion of the outer surface of the outer layer. In some examples, the weakened portion can comprise a score line along at least a portion of the inner layer and/or a slit along at least a portion of the inner layer. The weakened portion can be positioned at the at least one folded portion of the inner layer. In some examples, the longitudinal gap can be positioned between a first end and a second end of the outer layer.

In some examples, an expandable sheath can include a hydrophilic inner liner defining a generally horseshoe-shaped lumen therethrough, the inner liner including at least two weakened portions and an elastic cover positioned radially outward of the inner liner. In some examples, when the sheath is in the expanded configuration, the inner liner splits apart at the weakened portions so as to form a discontinuous inner liner.

Methods of making a sheath are also disclosed. One method includes providing a mandrel having a first diameter, providing a first tube having a second diameter, the second diameter being larger than the first diameter, mounting the first tube on the mandrel, gathering excess material of the first tube and folding the excess material to one side to form a folded portion of the inner layer. A second tube can then be provided, and the second tube can be cut to form a coiled layer. An adhesive can be applied to at least a portion of the coiled layer and the coiled layer can be mounted on the first tube such that the adhesive is positioned between the first tube and the coiled layer. The folded portion can be lifted in order to position a portion of the coiled layer under the folded portion.

Some methods include applying heat to the first tube, coiled layer, and mandrel so as to thermally fuse the first tube and the coiled layer together. In some methods, an elastic outer cover can be secured to the outer surface of the coiled layer. In some methods, a soft tip portion can be coupled to a distal end of the expandable sheath to facilitate passing the expandable sheath through a patient's vasculature.

In another example, a sheath for introducing a prosthetic device into a body can comprise an inner tubular layer comprising a longitudinal slit and partially defining an inner lumen, an outer tubular layer enveloping the inner layer, the outer tubular layer comprising a longitudinally extending, folded flap that overlies a portion of an outer surface of the outer layer when the sheath is in an unexpanded state, a tie layer positioned between and adhering the inner tubular layer to the outer tubular layer, wherein an outwardly directed radial force from a prosthetic device moving through the inner lumen widens the longitudinal slit and unfolds the folded flap to allow expansion of the sheath.

In a further example, a method of delivering a prosthetic device to a procedure site comprises inserting an expandable sheath into the vasculature of a subject, advancing the prosthetic device through an inner lumen of the expandable sheath, the prosthetic device applying an outwardly directed radial force to an inner tubular layer of the expandable sheath, widening a longitudinal slit in the inner tubular layer via the outwardly directed radial force, unfolding a longitudinally extending flap of an outer tubular layer via the outwardly directed radial force, narrowing the longitudinal slit of the inner tubular layer once the outwardly directed radial force has ceased, and delivering the prosthetic device to a procedure site.

In a further example, a method of manufacturing a sheath for introducing a prosthetic device into a body comprises loading an inner layer onto a tapered mandrel; applying heat to inner layer; flaring a proximal section of inner layer under heat; applying a tie layer to a body section of the inner layer; cutting a longitudinal slit in the inner layer and tie layer; loading inner layer and tie layer with longitudinal slit onto a mandrel; loading an outer layer over the tie layer; folding the outer layer to create a longitudinally extending flap; heat setting the folded outer layer; and removing the expandable sheath from mandrel.

In yet a further example, a sheath for introducing a prosthetic device into a body can comprise a continuous inner layer defining a lumen therethrough, the inner layer including a first fold and a second fold and an overlapping folded portion extending circumferentially between the first and second folds (e.g., when the sheath is in the unexpanded configuration), the folded portion comprising overlap in a radial direction of at least two thicknesses of the inner layer; a discontinuous outer layer extending at least partially around the inner layer, the outer layer having an overlapping portion and an underlying portion, at least a portion of the folded portion of the inner layer is positioned between the overlapping portion and the underlying portion; an adhesive layer (e.g., tie layer) is provided between the inner layer and the outer layer and at least partially adhering the inner layer to the outer layer; and an outer jacket extending around the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the prosthetic device passes through the lumen.

In another example, a sheath for introducing a prosthetic device into a body can comprise a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer; a discontinuous outer layer extending at least partially around the inner layer, the outer layer having an overlapping portion and an underlying portion, at least a portion of the folded portion of the inner layer is positioned between the overlapping portion and the underlying portion; a tie layer provided between the inner layer and the outer layer and at least partially adhering the inner layer to the outer layer; and an outer jacket extending around the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the prosthetic device passes through the lumen, wherein a lubricant is provided between the outer jacket and the outer layer.

In a further example, a method of delivering a prosthetic device to a procedure site comprises introducing an expandable sheath into the vasculature of a subject, advancing the prosthetic device through an inner lumen of the expandable sheath, the prosthetic device applying an outwardly directed radial force to an inner tubular layer of the expandable sheath, locally expanding the lumen of the sheath at a local axial location due to an outwardly directed radial force exerted by a prosthetic device against an inner surface of the lumen during advancement of the prosthetic device through the local axial location, wherein locally expanding the lumen comprises: moving a first fold of the inner layer circumferentially closer to a second fold of the inner layer and shortening an overlapping portion of the inner layer extending circumferentially between the first and second folds; and expanding an outer layer along at least one elongate gap generally aligned with the axis of the lumen and positioned adjacent to at least one of the folds, wherein expanding the outer layer along at least one elongate gap comprises moving a first portion of the outer layer away from a second portion of the outer layer, wherein the gap is defined between the first and second portions, as the first fold moves closer to the second fold, wherein the inner layer and the outer layer are at least partially adhered via a tie layer extending therebetween; locally contracting the lumen of the sheath at least partially back to an unexpanded configuration as the prosthetic device passes through the lumen; and delivering the prosthetic device to a procedure site.

In further example, a method of manufacturing a sheath for introducing a prosthetic device into a body comprises providing a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer; providing a discontinuous outer layer at least partially around the inner layer, the outer layer having an overlapping portion and an underlying portion, at least a portion of the folded portion of the inner layer is positioned between the overlapping portion and the underlying portion; providing a tie layer between the inner layer and the outer layer and at least partially adhering the inner layer to the outer layer; bonding the inner layer to the outer layer; providing a lubricant at a location proximate a longitudinally extending edge of the overlapping portion; and providing an outer jacket around the outer layer and bonding the outer jacket to the outer layer at at least one of their proximal and distal ends.

In another example, a sheath for introducing a prosthetic device into a body can comprise a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer; a discontinuous outer layer extending at least partially around the inner layer, the outer layer having an overlapping portion and an underlying portion, at least a portion of the folded portion of the inner layer is positioned between the overlapping portion and the underlying portion; a coiled wire along a length of the sheath, the coil wire providing uniform bending of the sheath to prevent kinking; a tie layer provided between the inner layer and the outer layer and at least partially adhering the inner layer to the outer layer; and an outer jacket extending around the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the prosthetic device passes through the lumen.

In a further example, a method of delivering a prosthetic device to a procedure site comprises introducing an expandable sheath into the vasculature of a subject; advancing the prosthetic device through an inner lumen of the expandable sheath, the prosthetic device applying an outwardly directed radial force to an inner tubular layer of the expandable sheath; locally expanding the lumen of the sheath at a local axial location due to an outwardly directed radial force exerted by a medical device against an inner surface of the lumen during advancement of the prosthetic device through the local axial location, wherein locally expanding the lumen comprises: moving a first fold of the inner layer circumferentially closer to a second fold of the inner layer and shortening an overlapping portion of the inner layer extending circumferentially between the first and second folds, and expanding an outer layer along at least one elongate gap generally aligned with the axis of the lumen and positioned adjacent to at least one of the folds, wherein expanding the outer layer along at least one elongate gap comprises moving a first portion of the outer layer away from a second portion of the outer layer, wherein the gap is defined between the first and second portions, as the first fold moves closer to the second fold, wherein a coiled wire structure is embedded in the inner and/or outer layer, the coiled wire increasing the kink resistance and increasing the column strength of the expandable sheath; locally contracting the lumen of the sheath at least partially back to an unexpanded configuration as the prosthetic device passes through the lumen; and delivering the prosthetic device to a procedure site.

The foregoing and other features and advantages of the invention will become more apparent from the following detailed description, which proceeds with reference to the accompanying figures.

BRIEF DESCRIPTION OF THE DRAWINGS

FIGS. 27B-27E show section views of various examples of a sheath in the unexpanded configuration.

FIGS. 29A-29D show section views of various examples of a sheath having overlapping sections.

FIGS. 32A-32H illustrates section or elevation views of various method steps of the methods shown in FIGS. 30-31.

FIG. 46 illustrates a section view of another example of an expandable sheath.

FIG. 47 shows an expanded configuration of the sheath of FIG. 46.

FIG. 65 is a partial section view of the outer jacket of FIG. 64.

DETAILED DESCRIPTION

Figure 1:
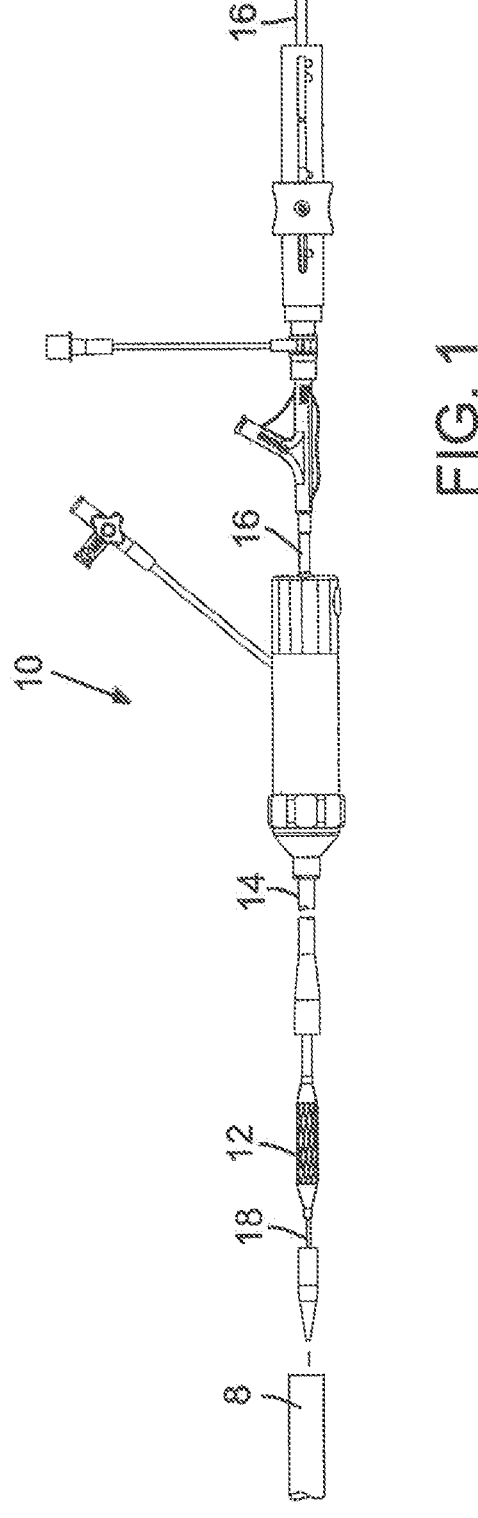
FIG. 1 is an elevation view of a sheath according to the present disclosure along with an endovascular delivery apparatus for implanting a prosthetic valve.

As used in this application and in the claims, the singular forms "a," "an," and "the" include the plural forms unless the context clearly dictates otherwise. Additionally, the term "includes" means "comprises." Further, the terms "coupled" and "associated" generally means electrically, electromagnetically, and/or physically (e.g., mechanically or chemically) coupled or linked and does not exclude the presence of intermediate elements between the coupled or associated items.

Although the operations of exemplary examples of the disclosed method may be described in a particular, sequential order for convenient presentation, it should be understood that disclosed examples can encompass an order of operations other than the particular, sequential order disclosed. For example, operations described sequentially may in some cases be rearranged or performed concurrently. Further, descriptions and disclosures provided in association with one particular example are not limited to that example, and may be applied to any example disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Disclosed examples of an expandable sheath can minimize trauma to the vessel by allowing for temporary expansion of a portion of the introducer sheath to accommodate the delivery system, followed by a return to the original diameter once the device passes through. Some examples can comprise a sheath with a smaller profile (e.g., a smaller diameter in the rest configuration) than that of prior art introducer sheaths. Furthermore, present examples can reduce the length of time a procedure takes, as well as reduce the risk of a longitudinal or radial vessel tear, or plaque dislodgement because only one sheath is required, rather than several different sizes of sheaths. Examples of the present expandable sheath can avoid the need for multiple insertions for the dilation of the vessel. Such expandable sheaths can be useful for many types of minimally invasive surgery, such as any surgery requiring introduction of an apparatus into a subject's vessel. For example, the sheath can be used to introduce other types of delivery apparatus for placing various types of intraluminal devices (e.g., stents, prosthetic heart valves, stented grafts, etc.) into many types of vascular and non-vascular body lumens (e.g., veins, arteries, esophagus, ducts of the biliary tree, intestine, urethra, fallopian tube, other endocrine or exocrine ducts, etc.).

FIG. 1 illustrates a sheath 8 according to the present disclosure, in use with a representative delivery apparatus 10, for delivering a prosthetic device 12, such as a tissue heart valve to a patient. The apparatus 10 can include a steerable guide catheter 14 (also referred to as a flex catheter), a balloon catheter 16 extending through the guide catheter 14, and a nose catheter 18 extending through the balloon catheter 16. The guide catheter 14, the balloon catheter 16, and the nose catheter 18 in the illustrated example are adapted to slide longitudinally relative to each other to facilitate delivery and positioning of the prosthetic device 12 at an implantation site in a patient's body, as described in detail below. Generally, sheath 8 is inserted into a vessel, such as the transfemoral vessel, passing through the skin of patient, such that the distal end of the sheath 8 is inserted into the vessel. Sheath 8 can include a hemostasis valve at the opposite, proximal end of the sheath. The delivery apparatus 10 can be inserted into the sheath 8, and the prosthetic device 12 can then be delivered and implanted within patient.

Figures 2A, 2B, 2C, 2D, 3, 4A, 4B, 5, 6, 7, 8:
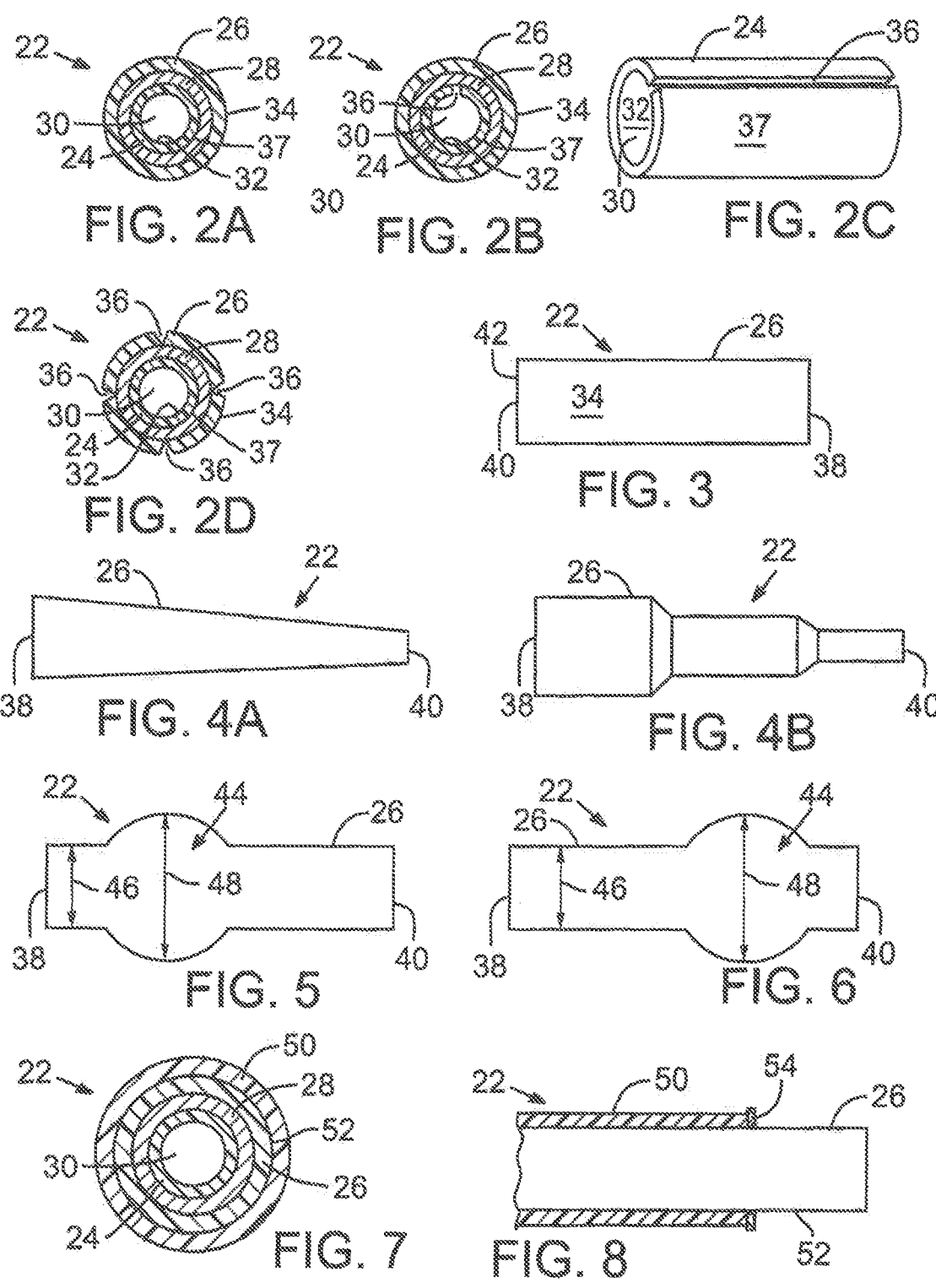
FIGS. 2A, B, and D are section views of examples of a sheath for introducing a prosthetic device into a patient.
FIG. 2C is a perspective view of one component of such a sheath.
FIG. 3 is an elevation view of the sheath shown in FIG. 2.
FIGS. 4A-4B are elevation views of two examples of a sheath according to the present disclosure, having varying outer diameters.
FIG. 5 illustrates an elevation view of one example of a sheath, expanded at a first location to accommodate a delivery system.
FIG. 6 shows an elevation view of the sheath of claim 5, expanded at a second location, farther down the sheath.
FIG. 7 shows a section view of another example of a sheath that further comprises an outer covering or shell.
FIG. 8 illustrates an elevation view of one example of a sheath with an outer covering or shell.
Figures 9, 10:
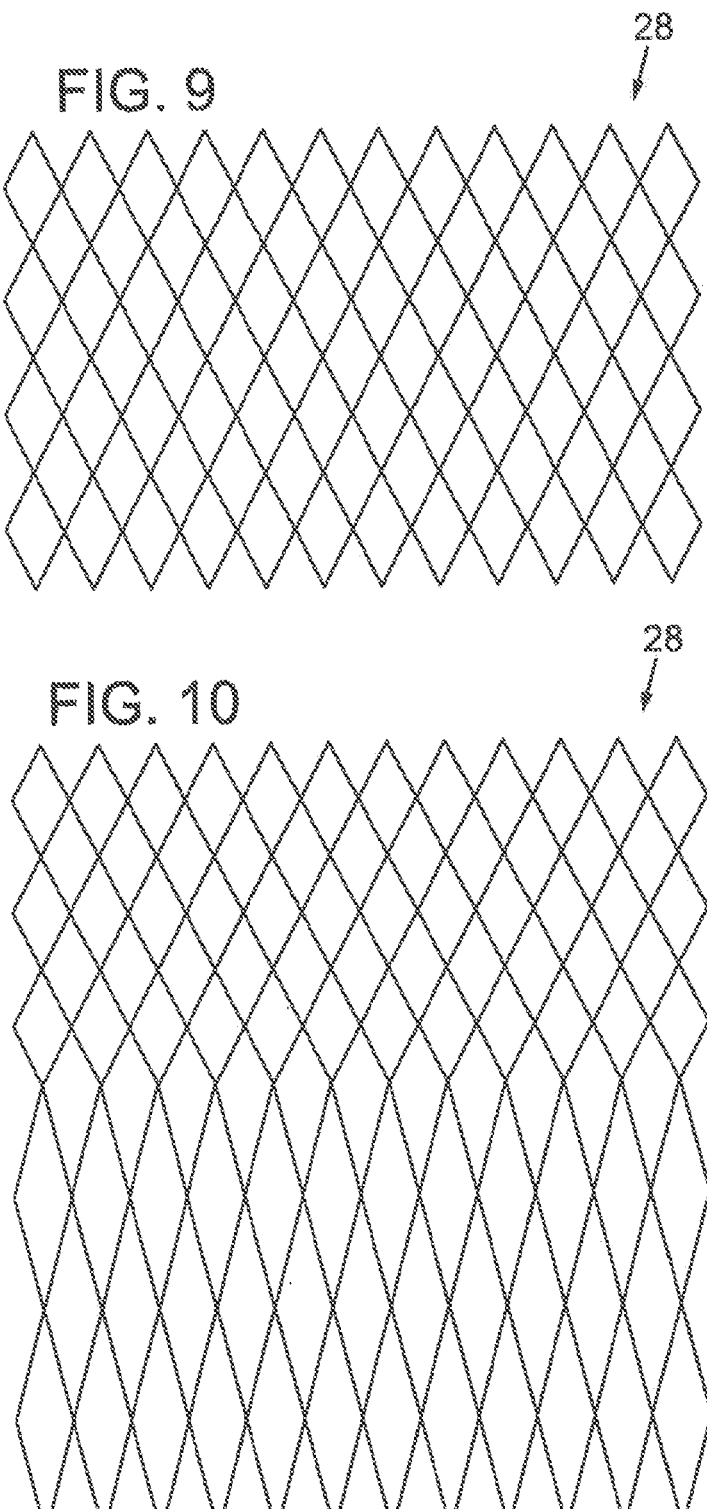
FIG. 9 illustrates a partial elevation view of one example of an intermediate tubular layer that can be used to construct a sheath according to the present disclosure.
FIG. 10 illustrates a partial elevation view of another example of an intermediate tubular layer having a variable diamond design.
Figure 11:
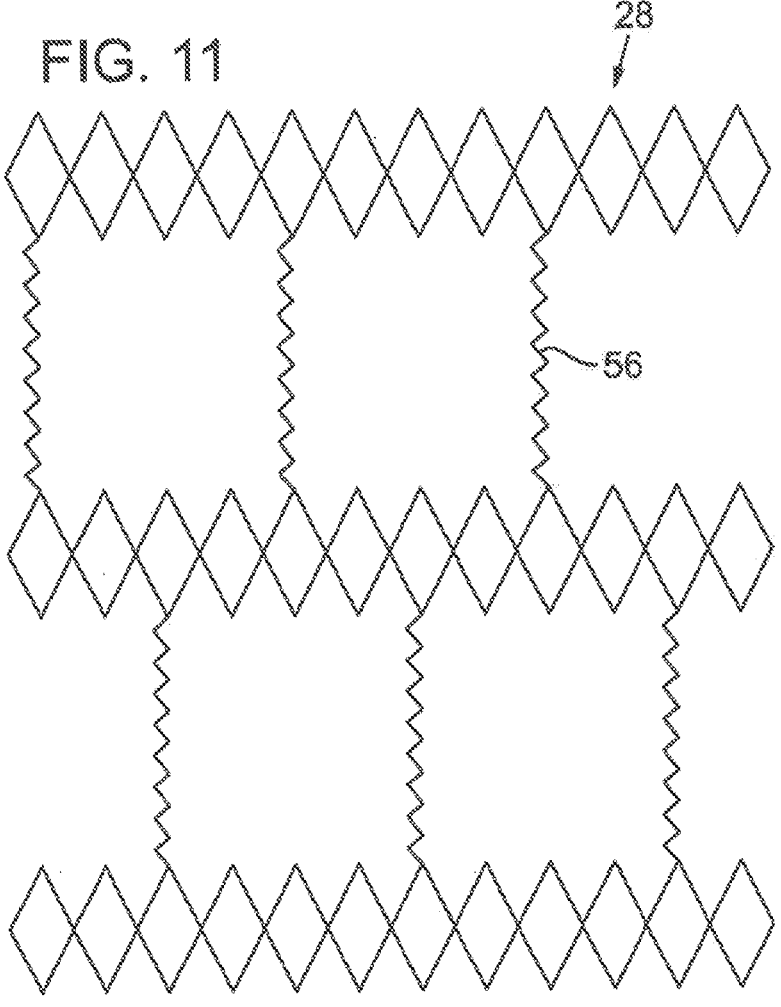
FIG. 11 illustrates a partial elevation view of another example of an intermediate tubular layer having a diamond design with spring struts.
Figure 12:
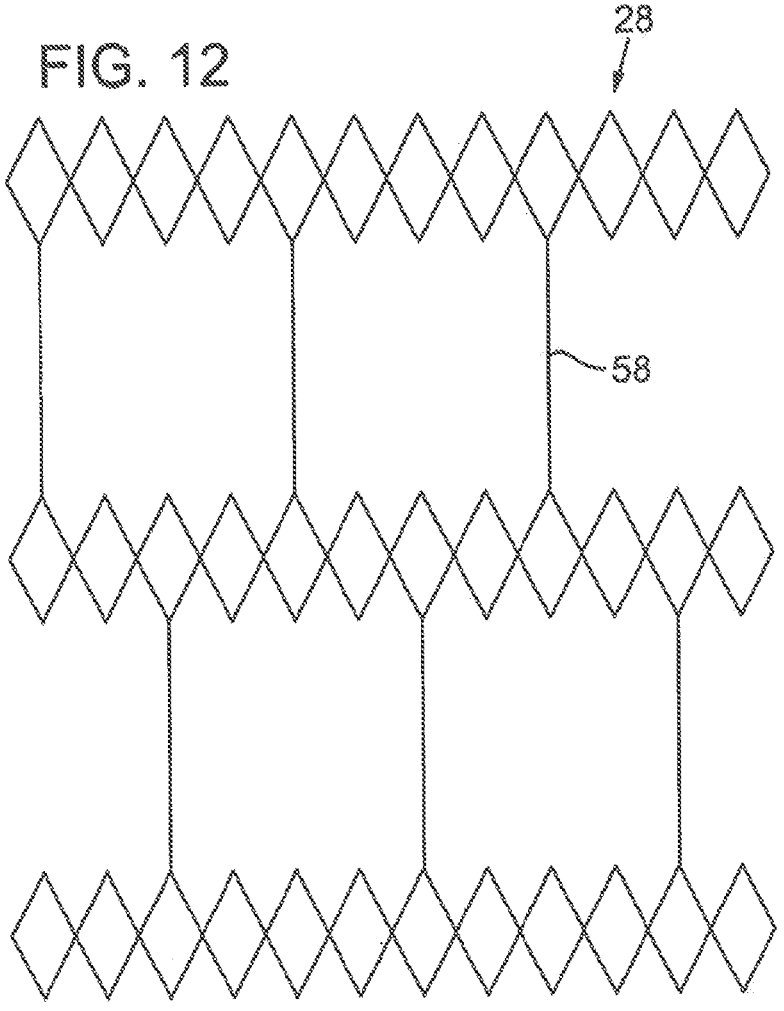
FIG. 12 illustrates a partial elevation view of another example of an intermediate tubular layer having a diamond design with straight struts.
Figures 13, 14:
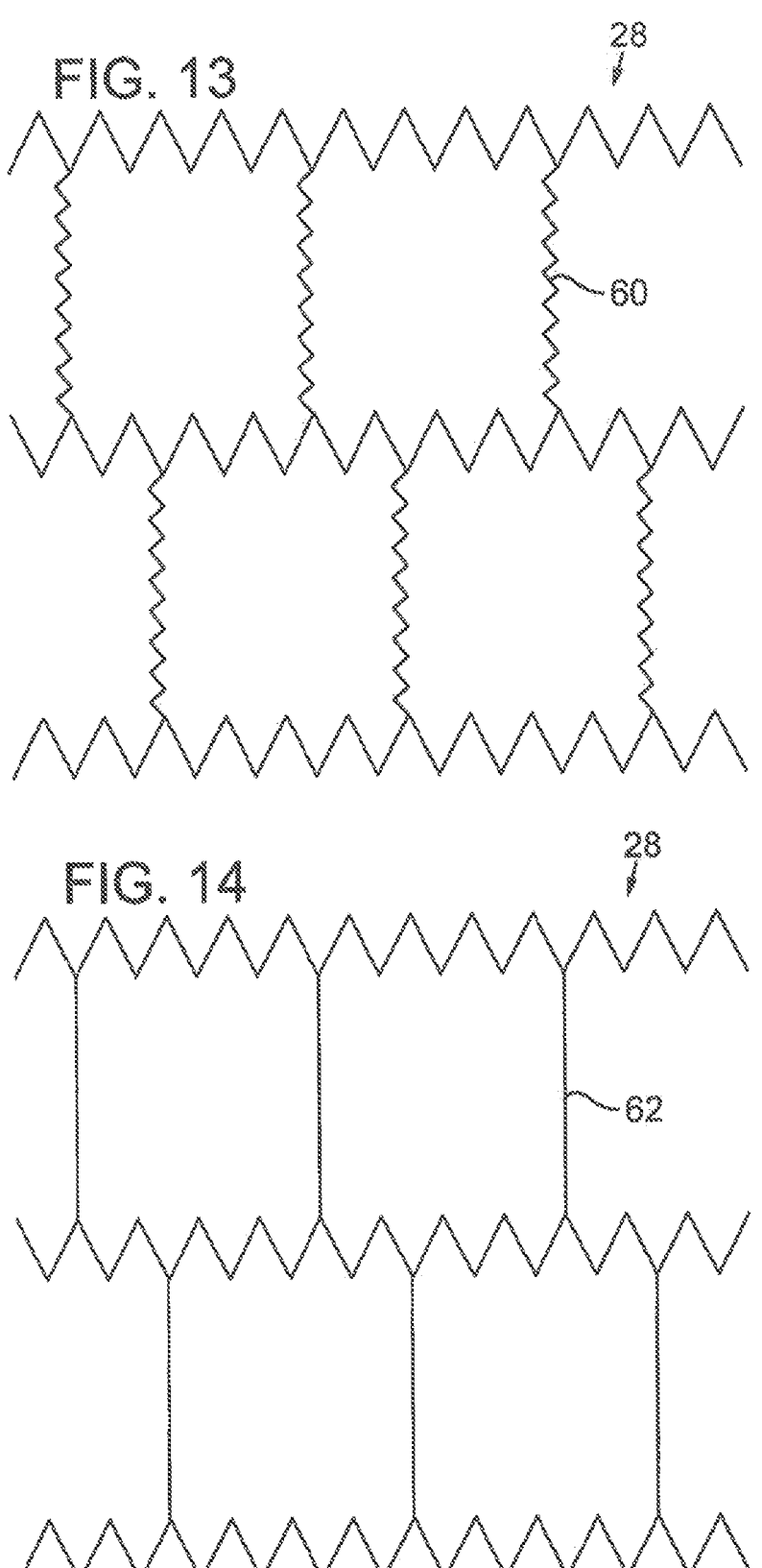
FIG. 13 illustrates a partial elevation view of another example of an intermediate tubular layer having a saw tooth design with spring struts.
FIG. 14 illustrates a partial elevation view of another example of an intermediate tubular layer having a saw tooth design with straight struts.
Figure 15:
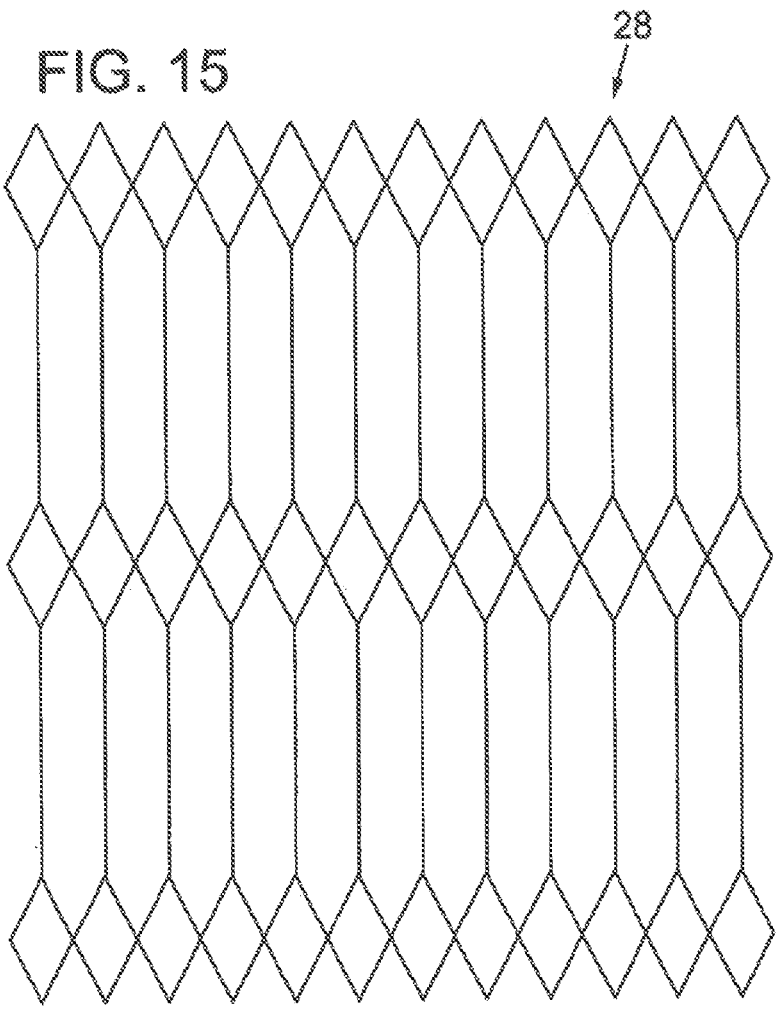
FIG. 15 illustrates a partial elevation view of another example of an intermediate tubular layer having a diamond design with straight struts.
Figure 16:
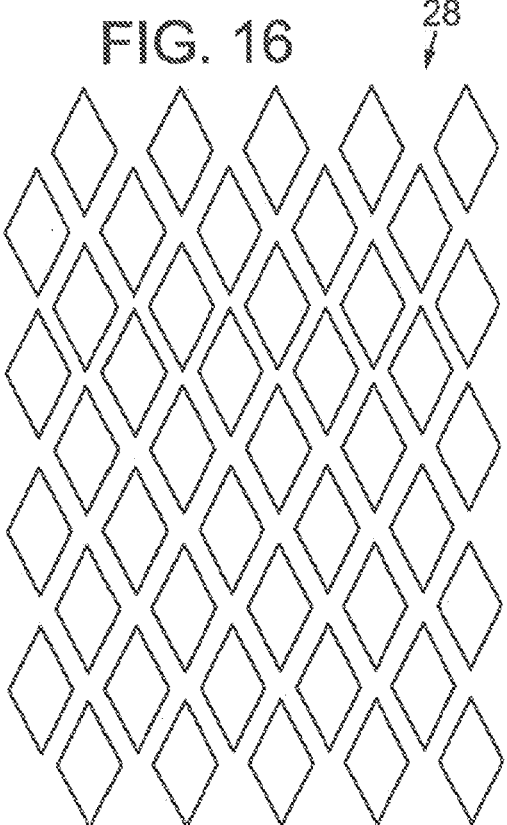
FIG. 16 illustrates a partial elevation view of another example of an intermediate tubular layer having a helical or spiral design.
Figure 17:
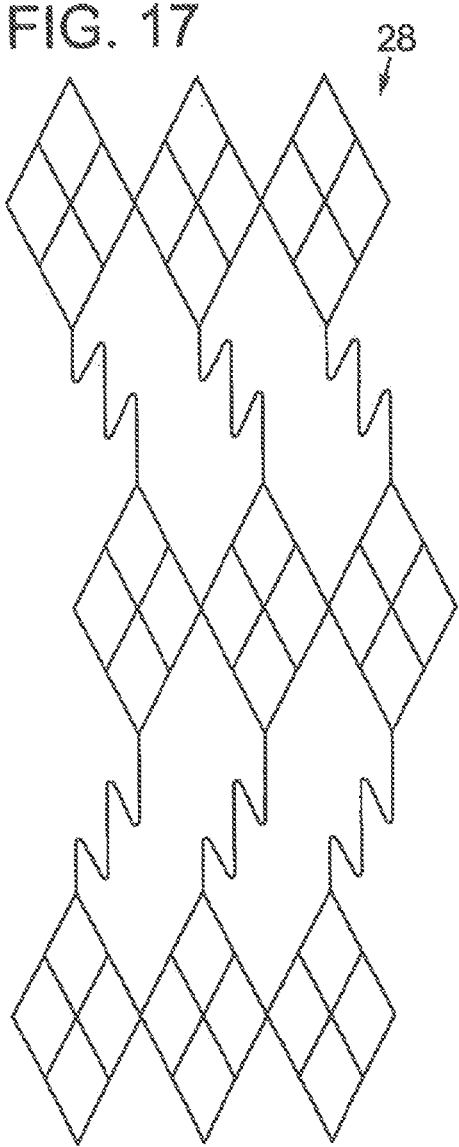
FIG. 17 illustrates a partial elevation view of another example of an intermediate tubular layer having a diamond design with non-straight struts.
Figures 18, 19:
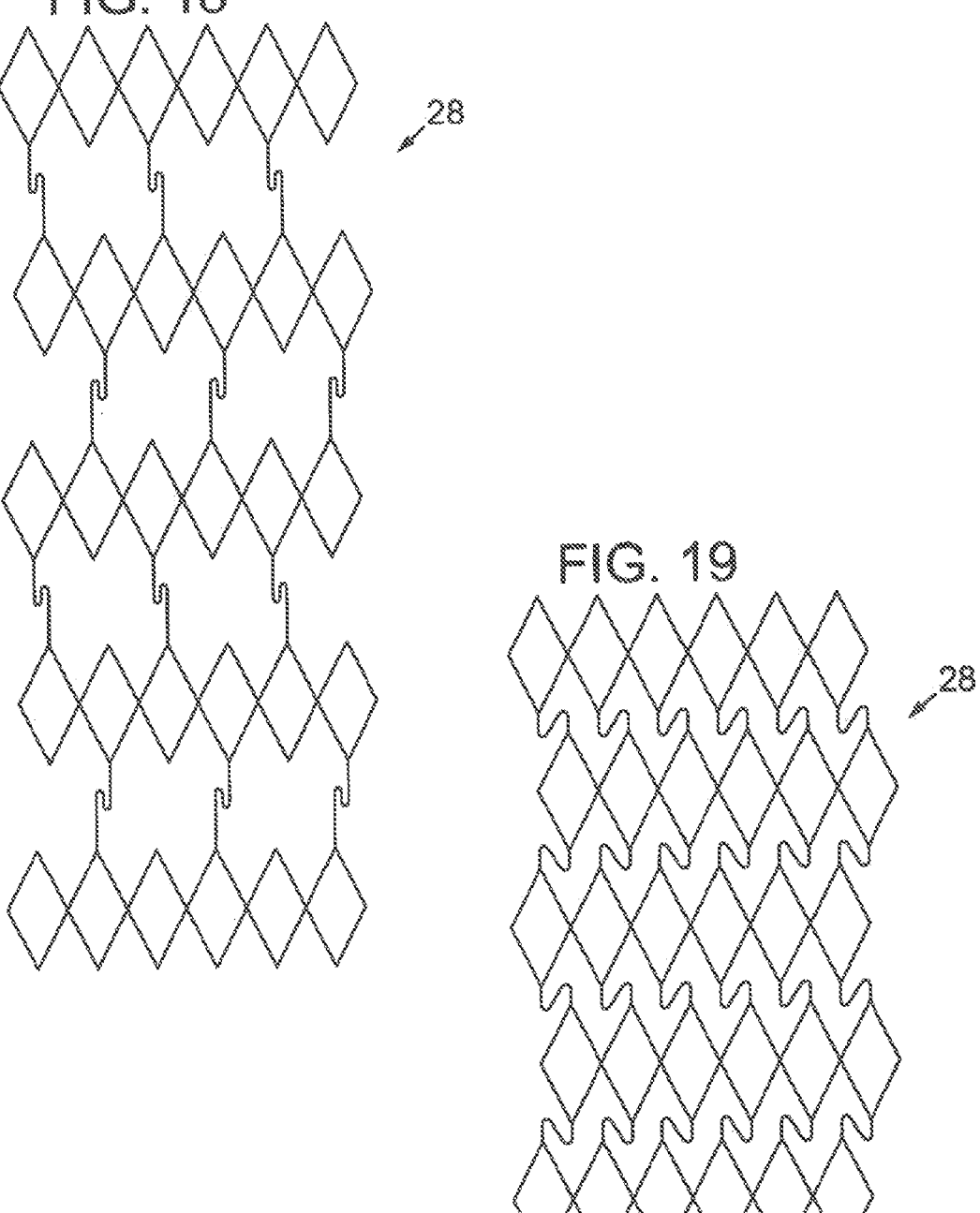
FIG. 18 illustrates a partial elevation view of another example of an intermediate tubular layer having an alternative diamond design with non-straight struts.
FIG. 19 illustrates a partial elevation view of another example of an intermediate tubular layer having yet another diamond design with non-straight struts.
Figure 20:
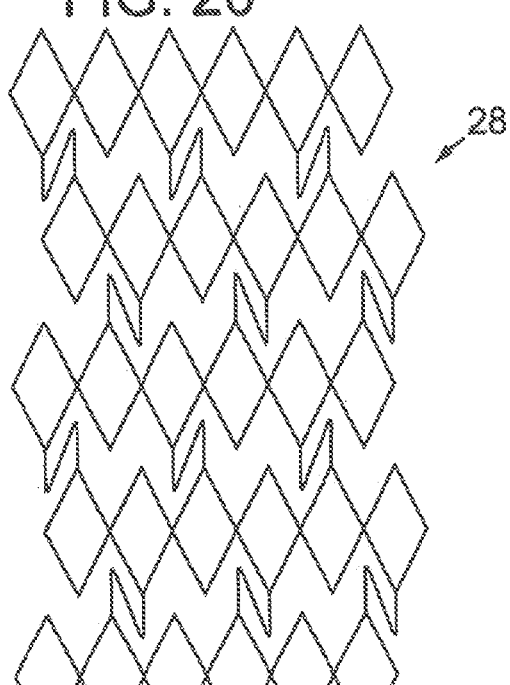
FIG. 20 illustrates a partial elevation view of another example of an intermediate tubular layer having a diamond design with struts.
Figure 21:
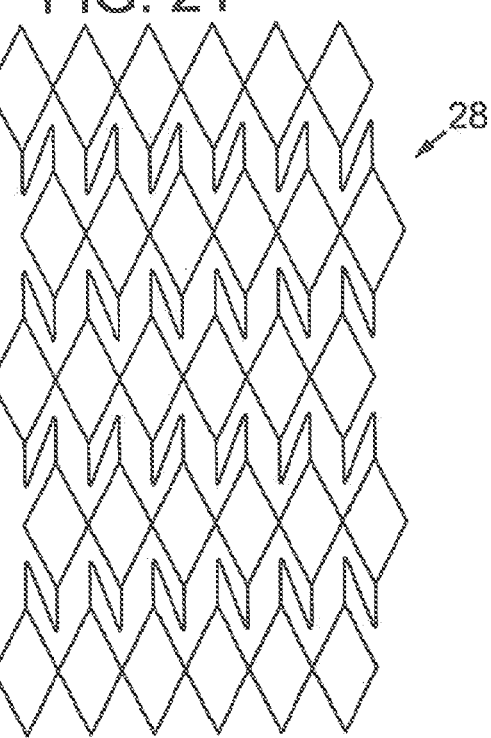
FIG. 21 illustrates a partial elevation view of another example of an intermediate tubular layer having a design similar to that shown in FIG. 20, but with additional struts.
Figure 22:
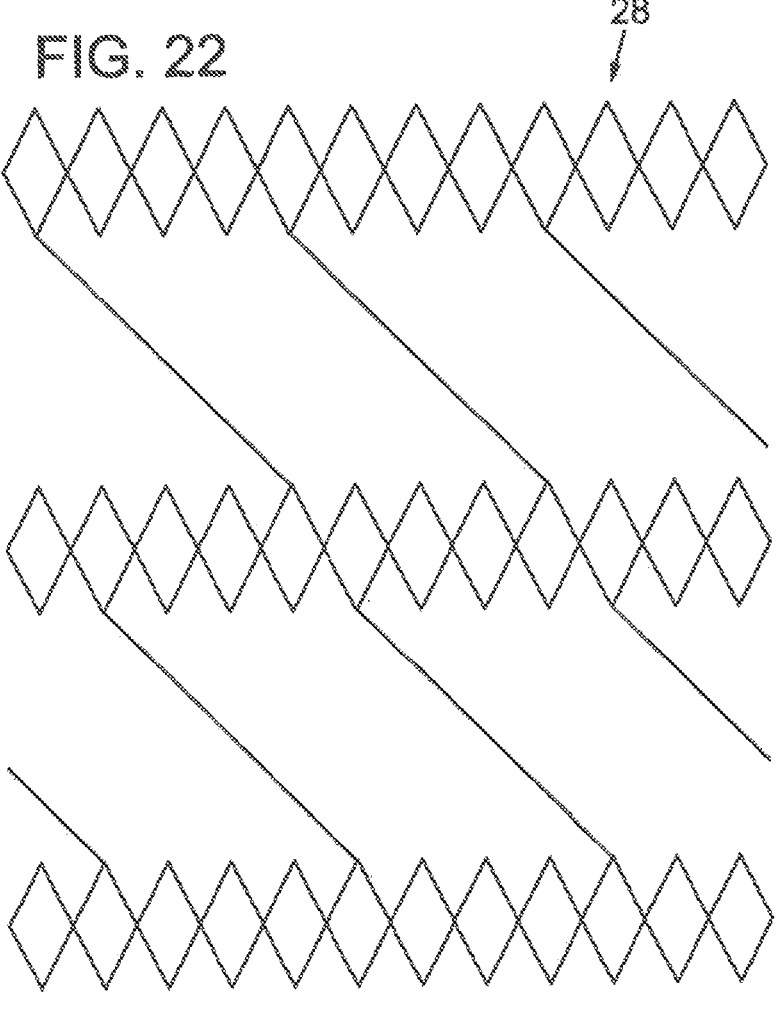
FIG. 22 illustrates a partial elevation view of another example of an intermediate tubular layer having a diamond design with spiral struts.
Figure 23:
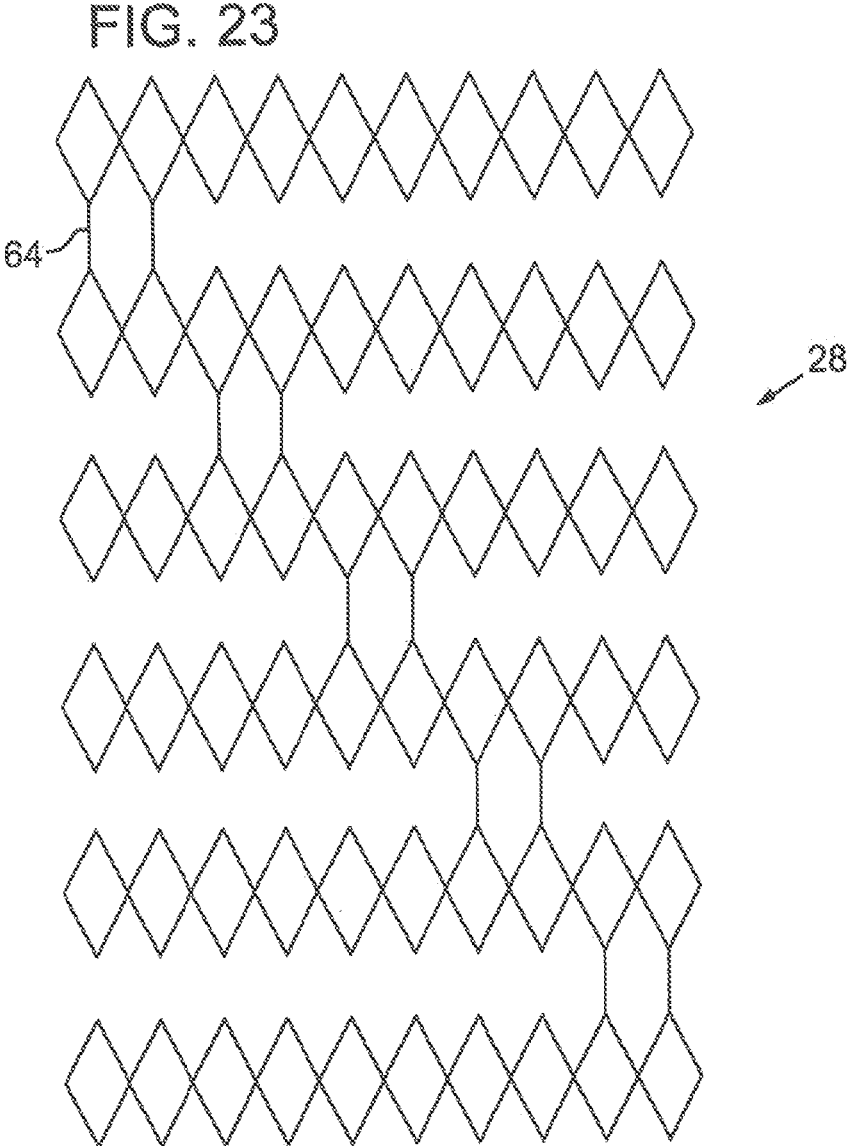
FIG. 23 illustrates a partial elevation view of another example of an intermediate tubular layer having a diamond design with adjacent struts.

FIGS. 2A, 2B, and 2D show section views of examples of a sheath 22 for use with a delivery apparatus such as that shown in FIG. 1. Example expandable sheaths are also disclosed in U.S. patent application Ser. No. 12/249,867, filed Oct. 10, 2008 (now U.S. Pat. No. 8,690,936), U.S. patent application Ser. No. 13/312,739, filed Dec. 6, 2011 (now U.S. Pat. No. 8,790,387), U.S. patent application Ser. No. 14/248,120 filed on Apr. 8, 2014 (now U.S. Pat. No. 9,301,840), U.S. patent application Ser. No. 14/324,894, filed Jul. 7, 2014 (now U.S. Pat. No. 9,301,841), U.S. patent application Ser. No. 15/057,953, filed Mar. 1, 2016 (now U.S. Pat. No. 9,987,134), U.S. patent application Ser. No. 15/997,587, filed Jun. 4, 2018, U.S. patent application Ser. No. 16/149,953, filed on Oct. 2, 2018 (now U.S. Pat. No. 10,524,905), U.S. patent application Ser. No. 16/149,956, filed on Oct. 2, 2018 (now U.S. Pat. No. 10,517,720), U.S. patent application Ser. No. 16/149,960, filed on Oct. 2, 2018

(now U.S. Pat. No. 10,524,906, and U.S. patent application Ser. No. 16/149,969, filed on Oct. 2, 2018 (now U.S. Pat. No. 10,524,907), the disclosures of which are herein incorporated by reference.

FIG. 2C shows a perspective view of one example of an inner layer 24 for use with the sheath 22. Sheath 22 includes an inner layer, such as inner polymeric tubular layer 24, an outer layer, such as outer polymeric tubular layer 26, and an intermediate tubular layer 28 disposed between the inner and outer polymeric tubular layers 24, 26. The sheath 22 defines a lumen 30 through which a delivery apparatus can travel into a patient's vessel in order to deliver, remove, repair, and/or replace a prosthetic device. Such introducer sheaths 22 can also be useful for other types of minimally invasive surgery, such as any surgery requiring introduction of an apparatus into a subject's vessel. For example, the sheath 22 also can be used to introduce other types of delivery apparatus for placing various types of intraluminal devices (e.g., stents, stented grafts, etc.) into many types of vascular and non-vascular body lumens (e.g., veins, arteries, esophagus, ducts of the biliary tree, intestine, urethra, fallopian tube, other endocrine or exocrine ducts, etc.).

The outer polymeric tubular layer 26 and the inner polymeric tubular layer 24 can comprise, for example, PTFE (e.g. Teflon®), polyimide, PEEK, polyurethane, nylon, polyethylene, polyamide, polyether block amides (e.g. PEBAX®), polyether block ester copolymer, polyesters, fluoropolymers, polyvinyl chloride, thermoset silicone, latex, poly-isoprene rubbers, polyolefin, other medical grade polymers, or combinations thereof. The intermediate tubular layer 28 can comprise a shape memory alloy such as Nitinol, and/or stainless steel, cobalt chromium, spectra fiber, polyethylene fiber, aramid fiber, or combinations thereof.

The inner polymeric tubular layer 24 can advantageously be provided with a low coefficient of friction on its inner surface. For example, the inner polymeric tubular layer 24 can have a coefficient of friction of less than about 0.1. Some examples of a sheath 22 can include a lubricious liner on the inner surface 32 of the inner polymeric tubular layer 24. Such a liner can facilitate passage of a delivery apparatus through the lumen 30 of the sheath 22. Examples of suitable lubricious liners include materials that can reduce the coefficient of friction of the inner polymeric tubular layer 24, such as PTFE, polyethylene, polyvinylidene fluoride, and combinations thereof. Suitable materials for a lubricious liner also include other materials desirably having a coefficient of friction of about 0.1 or less.

The inner diameter of the intermediate tubular layer 28 varies depending on the application and size of the delivery apparatus and prosthetic device. In some examples, the inner diameter ranges from about 0.005 inches to about 0.400 inches. The thickness of the intermediate tubular layer 28 can be varied depending on the desired amount of radial expansion, as well as the strength required. For example, the thickness of the intermediate tubular layer 28 can be from about 0.002 inches to about 0.025 inches. The thicknesses of the inner polymeric tubular layer 24 and the outer polymeric tubular layer 26 can also be varied depending on the particular application of the sheath 22. In some examples, the thickness of the inner polymeric tubular layer 24 ranges from about 0.0005 inches to about 0.010 inches, and in one particular example, the thickness is about 0.002 inches. Outer polymeric tubular layers 26 can have a thickness of from about 0.002 inches to about 0.015 inches, and in one particular example the outer polymeric tubular layer 26 has a thickness of about 0.010 inches.

The hardness of each layer of the sheath 22 can also be varied depending on the particular application and desired properties of the sheath 22. In some examples, the outer polymeric tubular layer 26 has a Shore hardness of from about 25 Durometer to about 75 Durometer.

Additionally, some examples of a sheath 22 can include an exterior hydrophilic coating on the outer surface 34 of the outer polymeric tubular layer 26. Such a hydrophilic coating can facilitate insertion of the sheath 22 into a patient's vessel. Examples of suitable hydrophilic coatings include the Harmony™ Advanced Lubricity Coatings and other Advanced Hydrophilic Coatings available from SurModics, Inc., Eden Prairie, MN. DSM medical coatings (available from Koninklijke DSM N.V, Heerlen, the Netherlands), as well as other hydrophilic coatings, are also suitable for use with the sheath 22.

In some examples, the outer surface 34 of the outer polymeric tubular layer 26 can be modified. For example, surface modifications such as plasma etching can be performed on the outer surface 34. Similarly, other surfaces, both outer and inner, can be surface modified according to certain examples and desired application. In some examples, surface modification can improve adhesion between the layers in the areas of the modification.

The sheath 22 also can have at least one radiopaque filler or marker. The radiopaque filler or marker can be associated with the outer surface 34 of the outer polymeric tubular layer 26. Alternatively, the radiopaque filler or marker can be embedded or blended within the outer polymeric tubular layer 24. Similarly, the radiopaque filler or marker can be associated with a surface of the inner polymeric tubular layer 24 or the intermediate tubular layer 28 or embedded within either or both of those layers.

Suitable materials for use as a radiopaque filler or marker include, for example, barium sulfite, bismuth trioxide, titanium dioxide, bismuth subcarbonate, or combinations thereof. The radiopaque filler can be mixed with or embedded in the material used to form the outer polymeric tubular layer 26, and can comprise from about 5% to about 45% by weight of the outer polymeric tubular layer. More or less radiopaque material can be used in some examples, depending on the particular application.

In some examples, the inner polymeric tubular layer 24 can comprise a substantially uniform cylindrical tube. In alternative examples, the inner polymeric tubular layer 24 can have at least one section of discontinuity along its longitudinal axis to facilitate radial expansion of the inner polymeric tubular layer 24. For example, the inner polymeric tubular layer 24 can be provided with one or more longitudinal notches and/or cuts 36 extending along at least a portion of the length of the sheath 22. Such notches or cuts 36 can facilitate radial expansion of the inner polymeric tubular layer 24, thus accommodating passage of a delivery apparatus or other device. Such notches and/or cuts 36 can be provided near the inner surface 32, near the outer surface 37, and/or substantially through the entire thickness of the inner polymeric tubular layer 24. In examples with a plurality of notches and/or cuts 36, such notches and/or cuts 36 can be positioned such that they are substantially equally spaced from one another circumferentially around the inner polymeric tubular layer 24. Alternatively, notches and cuts 36 can be spaced randomly in relation to one another, or in any other desired pattern. Some or all of any provided notches and/or cuts 36 can extend longitudinally along substantially the entire length of the sheath 22. Alternatively, some or all of any provided notches and/or cuts 36 can extend longitudinally only along a portion of the length of the sheath 22.

As shown in FIGS. 2B and 2C (which illustrates only the inner polymeric tubular layer 24), in some examples, the inner polymeric tubular layer 24 contains at least one notch or cut 36 that extends longitudinally and parallel to an axis defined by the lumen 30, extending substantially the entire length of the sheath 22. Thus, upon introduction of a delivery apparatus, the inner polymeric tubular layer 24 can split open along the notch and/or cut 36 and expand, thus accommodating the delivery apparatus.

Additionally or alternatively, as shown in FIG. 2D, the outer polymeric tubular layer 26 can comprise one or more notches and/or cuts 36. Notches and/or cuts 36, in some examples, do not extend through the entire thickness of the outer polymeric tubular layer 26. The notches and/or cuts 36 can be separable upon radial expansion of the sheath 22. The outer polymeric tubular layer 26 can be retractable longitudinally, or able to be pulled back away from the intermediate tubular layer 28 and the inner polymeric tubular layer 24. In examples with a retractable outer polymeric tubular layer 26, the outer polymeric tubular layer 26 can be retracted to accommodate or facilitate passage of a delivery apparatus through the lumen 30, and then can be replaced to its original position on the sheath 22.

FIG. 3 illustrates an elevation view of the sheath 22 shown in FIG. 2A. In this view, only the outer polymeric tubular layer 26 is visible. The sheath 22 comprises a proximal end 38 and a distal end 40 opposite the proximal end 38. The sheath 22 can include a hemostasis valve inside the lumen of the sheath 22, at or near the proximal end 38 of the sheath 22. Additionally, the sheath 22 can comprise a soft tip 42 at the distal end 40 of the sheath 22. Such a soft tip 42 can be provided with a lower hardness than the other portions of the sheath 22. In some examples, the soft tip 42 can have a Shore hardness from about 25 D to about 40 D.

As shown in FIG. 3, the unexpanded original outer diameter of the sheath 22 can be substantially constant across the length of the sheath 22, substantially from the proximal end 38 to the distal end 40. In alternative examples, such as the ones illustrated in FIGS. 4A-4B, the original unexpanded outer diameter of the sheath 22 can decrease from the proximal end 38 to the distal end 40. As shown in the example in FIG. 4A, the original unexpanded outer diameter can decrease along a gradient, from the proximal end 38 to the distal end 40. In alternative examples, such as the one shown in FIG. 4B, the original unexpanded outer diameter of sheath 22 can incrementally step down along the length of the sheath 22, wherein the largest original unexpanded outer diameter is near the proximal end 38 and the smallest original unexpanded outer diameter is near the distal end 40 of the sheath 22.

As shown in FIGS. 5-6, the sheath 22 can be designed to locally expand as the prosthetic device is passed through the lumen of the sheath 22, and then substantially return to its original shape once the prosthetic device has passed through that portion of the sheath 22. For example, FIG. 5 illustrates a sheath 22 have a localized bulge 44, representative of a device being passed through the internal lumen of the sheath 22. FIG. 5 shows the device close to the proximal end 38 of the sheath 22, close to the area where the device is introduced into the sheath 22. FIG. 6 shows the sheath 22 of FIG. 5, with the device having progressed further along the sheath 22. The localized bulge 44 is now closer to the distal end 40 of the sheath 22, and thus is about to be introduced to a patient's vessel. As evident from FIGS. 5 and 6, once the localized bulge associated with the device has passed through a portion of the lumen of the sheath 22, that portion of the sheath 22 can automatically return to its original shape and size, at least in part due to the materials and structure of the sheath 22.

The sheath 22 has an unexpanded inner diameter equal to the inner diameter of the inner polymeric tubular layer (not visible in FIGS. 5-6), and an unexpanded outer diameter 46 equal to the outer diameter of the outer polymeric tubular layer 26. The sheath 22 is designed to be expanded to an expanded inner diameter and an expanded outer diameter 48 which are larger than the unexpanded inner diameter and the unexpanded outer diameter 46, respectively. In one representative example, the unexpanded inner diameter is about 16 Fr and the unexpanded outer diameter 46 is about 19 Fr, while the expanded inner diameter is about 26 Fr and the expanded outer diameter 48 is about 29 Fr. Different sheaths 22 can be provided with different expanded and unexpanded inner and outer diameters, depending on the size requirements of the delivery apparatus for various applications. Additionally, some examples can provide more or less expansion depending on the particular design parameters, the materials, and/or configurations used.

In some examples of a sheath according to the present disclosure, and as shown in section in FIG. 7 and in elevation in FIG. 8, the sheath 22 can additionally comprise an outer covering, such as outer polymeric covering 50, disposed on the outer surface 52 of the outer polymeric tubular layer 26. The outer polymeric covering 50 can provide a protective covering for the underlying sheath 22. In some examples, the outer polymeric covering 50 can contain a self-expandable sheath in a crimped or constrained state, and then release the self-expandable sheath upon removal of the outer polymeric covering 50. For example, in some examples of a self-expandable sheath, the intermediate tubular layer 28 can comprise Nitinol and/or other shape memory alloys, and the intermediate tubular layer 28 can be crimped or radially compressed to a reduced diameter within the outer polymeric tubular layer 26 and the outer polymeric covering 50. Once the self-expandable sheath is at least partially inserted into a patient's vessel, the outer polymeric covering 50 can be slid back, peeled away, or otherwise at least partially removed from the sheath. To facilitate removal of the outer polymeric covering 50, a portion of the outer polymeric covering 50 can remain outside the patient's vessel, and that portion can be pulled back or removed from the sheath to allow the sheath to expand. In some examples, substantially the entire outer polymeric covering 50 can be inserted, along with the sheath, into a patient's vessel. In these examples, an external mechanism attached to the outer polymeric covering 50 can be provided, such that the outer polymeric covering can be at least partially removed from the sheath once the sheath is inserted into a patient's vessel.

Once no longer constrained by the outer polymeric covering 50, the radially compressed intermediate tubular layer 28 can self-expand, causing expansion of the sheath along the length of the intermediate tubular layer 28. In some examples, portions of the sheath can radially collapse, at least partially returning to the original crimped state, as the sheath is being withdrawn from the vessel after completion of the surgical procedure. In some examples, such collapse can be facilitated and/or encouraged by an additional device or layer that, in some examples, can be mounted onto a portion of the sheath prior to the sheath's insertion into the vessel.

The outer polymeric covering 50, in some examples, is not adhered to the other layers of the sheath 22. For example, the outer polymeric covering 50 may be slidable with respect to the underlying sheath, such that it can be easily removed or retracted from its initial position on the sheath 22.

As seen in FIG. 8, the outer polymeric covering 50 can include one or more peel tabs 54 to facilitate manual removal of the outer polymeric covering 50. The outer polymeric covering 50 can be automatically or manually retractable and/or splittable to facilitate radial expansion of the sheath 22. Peel tabs 54 can be located approximately 90 degrees from any cut or notch present in the outer polymeric covering 50, and approximately 180 degrees offset from one another. In alternative examples, the peel tabs 54 can extend substantially around the circumference of the outer polymeric covering 50, thus resulting in a single circular peel tab 54.

Suitable materials for the outer polymeric covering 50 are similar to those materials suitable for the inner polymeric tubular layer and the outer polymeric tubular layer, and can include PTFE and/or high density polyethylene.

Turning now to the intermediate tubular layer 28, several different configurations are possible. The intermediate tubular layer 28 is generally a thin, hollow, substantially cylindrical tube comprising an arrangement, pattern, structure, or configuration of wires or struts, however other geometries can also be used. The intermediate tubular layer 28 can extend along substantially the entire length of the sheath 22, or alternatively, can extend only along a portion of the length of sheath 22. Suitable wires can be round, ranging from about 0.0005 inches thick to about 0.10 inches thick, or flat, ranging from about 0.0005 inches×0.003 inches to about 0.003 inches×0.007 inches. However, other geometries and sizes are also suitable for certain examples. If braided wire is used, the braid density can be varied. Some examples have a braid density of from about thirty picks per inch to about eighty picks per inch and can include up to thirty-two wires in various braid patterns.

One representative example of an intermediate tubular layer comprises a braided Nitinol composite which is at least partially encapsulated by an inner polymeric tubular member and an outer polymeric tubular member disposed on inner and outer surfaces of the intermediate tubular layer, respectively. Such encapsulation by polymeric layers can be accomplished by, for example, fusing the polymeric layers to the intermediate tubular layer, or dip coating the intermediate tubular layer. In some examples, an inner polymeric tubular member, an intermediate tubular layer, and an outer polymeric tubular layer can be arranged on a mandrel, and the layers can then be thermally fused or melted into one another by placing the assembly in an oven or otherwise heating it. The mandrel can then be removed from the resulting sheath. In other examples, dip coating can be used to apply an inner polymeric tubular member to the surface of a mandrel. The intermediate tubular layer can then be applied, and the inner polymeric tubular member allowed to cure. The assembly can then be dip coated again, such as to apply a thin coating of, for example, polyurethane, which will become the outer polymeric tubular member of the sheath. The sheath can then be removed from the mandrel.

Additionally, the intermediate tubular layer 28 can be, for example, braided or laser cut to form a pattern or structure, such that the intermediate tubular layer 28 is amenable to radial expansion. FIGS. 9-23 illustrate partial elevation views of various structures for the intermediate tubular layer. Some illustrated structures, such as those shown in FIGS. 11-14 and 23, include at least one discontinuity. For example, the struts 56, 58, 60, 62, 64 shown in FIGS. 11, 12, 13, 14, and 23, respectively, result in a discontinuous intermediate tubular layer 28 in that the struts 56, 58, 60, 62, 64 separate adjacent sections of the intermediate tubular layer 28 from each other, where the sections are spaced apart from each other along a longitudinal axis parallel to the lumen of the sheath. Thus, the structure of the intermediate tubular layer 28 can vary from section to section, changing along the length of the sheath.

The structures shown in FIGS. 9-23 are not necessarily drawn to scale. Components and elements of the structures can be used alone or in combination within a single intermediate tubular layer 28. The scope of the intermediate tubular layer 28 is not meant to be limited to these particular structures; they are merely exemplary examples.

Figures 24, 25:
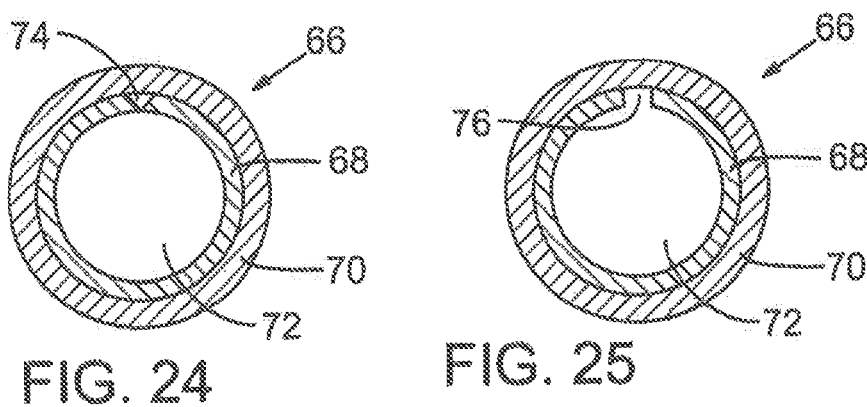
FIG. 24 illustrates a section view of one example of a sheath having a longitudinal notch.
FIG. 25 shows a section view of one example of a sheath having a longitudinal cut in the inner layer.
Figure 26:
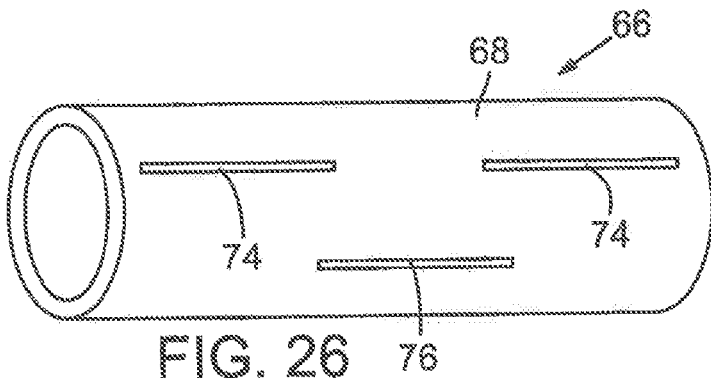
FIG. 26 shows a perspective view of one example of a sheath having a plurality of notches or cuts in the outer tubular layer.

Alternative examples of a sheath for introducing a prosthetic device are also described. For example, FIGS. 24-26 illustrate a section view and a perspective view, respectively, of a sheath 66 for introducing a prosthetic device into a body. The sheath 66 comprises an inner layer, such as inner polymeric layer 68, an outer layer, such as polymeric tubular layer 70, and a hemostasis valve (not shown). The inner polymeric layer 68 and the outer polymeric tubular layer 70 at least partially enclose a lumen 72, through which a delivery apparatus and prosthetic device can pass from outside the patient's body into the patient's vessel. Either or both of the inner polymeric layer 68 and the outer polymeric tubular layer 70 can be provided with at least one longitudinal notch and/or cut to facilitate radial expansion of the sheath.

For example, FIG. 24 illustrates a longitudinal notch 74 in the inner polymeric layer 68 that can facilitate radial expansion of the sheath 66. The longitudinal notch 74 can separate or split open completely upon application of a radial force due to insertion of a delivery apparatus or prosthetic device. Similarly, FIG. 25 illustrates a longitudinal cut 76 in the inner polymeric layer 68 that can also facilitate radial expansion of the sheath 66. The outer polymeric tubular layer 70 can, additionally or alternatively, comprise one or more longitudinal cuts 76 or notches 74. Such cuts and/or notches, whether in the inner polymeric layer 68 or the outer polymeric tubular layer 70, can extend substantially through the entire thickness of the layer, or can extend only partially through the thickness of the layer. The cuts and/or notches can be positioned at or near the inner or outer surface, or both surfaces, of the inner and/or outer polymeric layers 68, 70.

FIG. 26 illustrates a perspective view of one example of an inner polymeric layer 68 with longitudinal notches 74 and a longitudinal cut 76. More or fewer notches 74 and/or cuts 76 can be provided. For clarity, the outer polymeric tubular layer 70 is not shown in FIG. 26. As shown in FIG. 26, longitudinal notches 74 and/or cuts 76 can extend only along a portion of the length of sheath 66. In alternative examples, one or more notches 74 and/or cuts 76 can extend substantially along the entire length of the sheath 66. Additionally, notches 74 and/or cuts 76 can be positioned randomly or patterned.

One particular example of a sheath 66 comprises a sheath having a notch or cut in the outer polymeric tubular layer 70 or the inner polymeric layer 68 that extends longitudinally along approximately 75% of the length of the sheath 66. If such a notch or cut extends only partially through the associated layer, it can have a relatively low tear force, such as a tear force of about 0.5 lbs., so that the notch splits open relatively easily during use.

The inner polymeric layer 68 and the outer polymeric tubular layer 70 can optionally be adhered together or otherwise physically associated with one another. The amount of adhesion between the inner polymeric layer 68 and the outer polymeric tubular layer 70 can be variable over the surfaces of the layers. For example, little to no adhesion can be present at areas around or near any notches and/or cuts present in the layers, so as not to hinder radial expansion of the sheath 66. Adhesion between the layers can be created by, for example, thermal bonding and/or coatings. Examples of a sheath 66 can be formed from an extruded tube, which can serve as the inner polymeric layer 68. The inner polymeric layer 68 can be surface treated, such as by plasma etching, chemical etching or other suitable methods of surface treatment. By treating the surface of the inner polymeric layer 68, the outer surface of the inner polymeric layer 68 can have areas with altered surface angles that can provide better adhesion between the inner polymeric layer 68 and the outer polymeric tubular layer 70. The treated inner polymeric layer can be dip coated in, for example, a polyurethane solution to form the outer polymeric tubular layer 70. In some configurations, the polyurethane may not adhere well to untreated surface areas of the inner polymeric layer 68. Thus, by surface treating only surface areas of the inner polymeric layer 68 that are spaced away from the areas of expansion (e.g. the portion of the inner polymeric layer 68 near notches 74 and/or cuts 76), the outer polymeric tubular layer 70 can be adhered to some areas of the inner polymeric layer 68, while other areas of the inner polymeric layer 68 remain free to slide relative to the outer polymeric tubular layer 70, thus allowing for expansion of the diameter of the sheath 66. Thus, areas around or near any notches 74 and/or cuts 76 can experience little to no adhesion between the layers, while other areas of the inner and outer polymeric layers 68, 70 can be adhesively secured or otherwise physically associated with each other.

As with previously disclosed examples, the examples illustrated in FIGS. 24-26 can be applied to sheaths having a wide variety of inner and outer diameters. Applications can utilize a sheath of the present disclosure with an inner diameter of the inner polymeric layer 68 that is expandable to an expanded diameter of from about 3 Fr to about 26 Fr. The expanded diameter can vary slightly along the length of the sheath 66. For example, the expanded outer diameter at the proximal end of the sheath 66 can range from about 3 Fr to about 28 Fr, while the expanded outer diameter at the distal end of the sheath 66 can range from about 3 Fr to about 25 Fr. Examples of a sheath 66 can expand to an expanded outer diameter that is from about 10% greater than the original unexpanded outer diameter to about 100% greater than the original unexpanded outer diameter.

In some examples, the outer diameter of the sheath 66 gradually decreases from the proximal end of the sheath 66 to the distal end of the sheath 66. For example, in one example, the outer diameter can gradually decrease from about 26 Fr at the proximal end to about 18 Fr at the distal end. The diameter of the sheath 66 can transition gradually across substantially the entire length of the sheath 66. In other examples, the transition or reduction of the diameter of the sheath 66 can occur only along a portion of the length of the sheath 66. For example, the transition can occur along a length from the proximal end to the distal end, where the length can range from about 0.5 inches to about the entire length of sheath 66.

Suitable materials for the inner polymeric layer 68 can have a high elastic strength and include materials discussed in connection with other examples, especially Teflon (PTFE), polyethylene (e.g. high density polyethylene), fluoropolymers, or combinations thereof. In some examples, the inner polymeric layer 68 preferably has a low coefficient of friction, such as a coefficient of friction of from about 0.01 to about 0.5. Some preferred examples of a sheath 66 comprise an inner polymeric layer 68 having a coefficient of friction of about 0.1 or less.

Likewise, suitable materials for the outer polymeric tubular layer 70 include materials discussed in connection with other examples, and other thermoplastic elastomers and/or highly elastic materials.

The Shore hardness of the outer polymeric tubular layer 70 can be varied for different applications and examples. Some examples include an outer polymeric layer with a Shore hardness of from about 25 A to about 80 A, or from about 20D to about 40D. One particular example comprises a readily available polyurethane with a Shore hardness of 72 A. Another particular example comprises a polyethylene inner polymeric layer dipped in polyurethane or silicone to create the outer polymeric layer.

The sheath 66 can also include a radiopaque filler or marker as described above. In some examples, a distinct radiopaque marker or band can be applied to some portion of the sheath 66. For example, a radiopaque marker can be coupled to the inner polymeric layer 68, the outer polymeric tubular layer 70, and/or can be positioned in between the inner and outer polymeric layers 68, 70.

Figures 27A, 28:
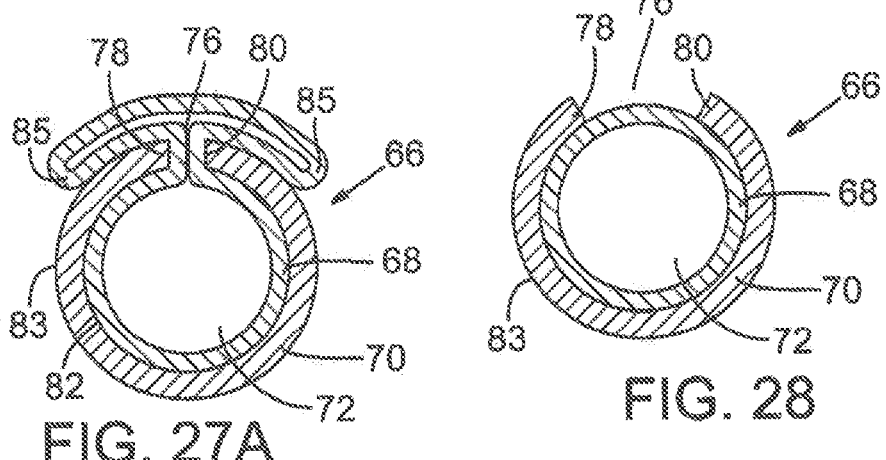
FIG. 27A illustrates a section view of one example of a sheath, wherein the outer tubular layer contains a longitudinal cut, and the inner layer extends into the gap created by the cut in the outer tubular layer, in an unexpanded configuration.
FIG. 28 shows a section view of the sheath of FIG. 27A in an expanded configuration.

FIGS. 27A-27E and 28 illustrate section views of various examples of unexpanded (FIGS. 27A-27E) and expanded (FIG. 28) sheaths 66 according to the present disclosure. The sheath 66 includes a split outer polymeric tubular layer 70 having a longitudinal cut 76 through the thickness of the outer polymeric tubular layer 70 such that the outer polymeric tubular layer 70 comprises a first portion 78 and a second portion 80 separable from one another along the cut 76. An expandable inner polymeric layer 68 is associated with an inner surface 82 of the outer polymeric tubular layer 70, and, in the unexpanded configuration shown in FIG. 27A, a portion of the inner polymeric layer 68 extends through a gap created by the cut 76 and can be compressed between the first and second portions 78, 80 of the outer polymeric tubular layer 70. Upon expansion of the sheath 66, as shown in FIG. 28, first and second portions 78, 80 of the outer polymeric tubular layer 70 have separated from one another, and the inner polymeric layer 68 is expanded to a substantially cylindrical tube. In some examples, two or more longitudinal cuts 76 may be provided through the thickness of the outer polymeric tubular layer 70. In such examples, a portion of the inner polymeric layer 68 may extend through each of the longitudinal cuts 76 provided in the outer polymeric tubular layer 70.

Preferably, the inner polymeric layer 68 comprises one or more materials that are elastic and amenable to folding and/or pleating. For example, FIG. 27A illustrates an inner polymeric layer 68 with folded regions 85. As seen in FIGS. 27A-27E, the sheath 66 can be provided with one or more folded regions 85. Such folded regions 85 can be provided along a radial direction and substantially conform to the circumference of the outer polymeric tubular layer 70. At least a portion of the folded regions 85 can be positioned adjacent the outer surface 83 of the outer polymeric tubular layer 70. Additionally, as shown in FIGS. 27B and 27E, at least a portion of the folded region or regions 85 can be overlapped by an outer covering, such as outer polymeric covering 81. The outer polymeric covering 81 can be adjacent at least a portion of the outer surface 83 of the outer polymeric tubular layer 70. The outer polymeric covering 81 serves to at least partially contain the folded regions 85 of the inner polymeric layer 68, and can also prevent the folded regions 85 from separating from the outer polymeric tubular layer 70 when, for example, the sheath 66 undergoes bending. In some examples, the outer polymeric covering 81 can be at least partially adhered to the outer surface 83 of the outer polymeric tubular layer 70. The outer polymeric covering 81 can also increase the stiffness and/or durability of the sheath 66. Additionally, as shown in FIGS. 27B and 27E, the outer polymeric covering 81 may not entirely overlap the circumference of the sheath 66. For example, the outer polymeric covering 81 may be provided with first and second ends, where the ends do not contact one another. In these examples, only a portion of the folded region 85 of the inner polymeric layer 68 is overlapped by the outer polymeric covering 81.

In examples having a plurality of folded regions 85, the regions can be equally displaced from each other around the circumference of the outer polymeric tubular layer 70. Alternatively, the folded regions can be off-center, different sizes, and/or randomly spaced apart from each other. While portions of the inner polymeric layer 68 and the outer polymeric tubular layer 70 can be adhered or otherwise coupled to one another, the folded regions 85 preferably are not adhered or coupled to the outer tubular layer 70. For example, adhesion between the inner polymeric layer 68 and the outer polymeric tubular layer 70 can be highest in areas of minimal expansion.

One particular example of the sheath illustrated in FIGS. 27A-28 comprises a polyethylene (e.g. high density polyethylene) outer polymeric tubular layer 70 and a PTFE inner polymeric layer 68. However, other materials are suitable for each layer, as described above. Generally, suitable materials for use with the outer polymeric tubular layer 70 include materials having a high stiffness or modulus of strength that can support expansion and contraction of the inner polymeric layer 68.

In some examples, the outer polymeric tubular layer 70 comprises the same material or combination of materials along the entire length of the outer polymeric tubular layer 70. In alternative examples, the material composition can change along the length of the outer polymeric tubular layer 70. For example, the outer polymeric tubular layer can be provided with one or more segments, where the composition changes from segment to segment. In one particular example, the Durometer rating of the composition changes along the length of the outer polymeric tubular layer 70 such that segments near the proximal end comprise a stiffer material or combination of materials, while segments near the distal end comprise a softer material or combination of materials. This can allow for a sheath 66 having a relatively stiff proximal end at the point of introducing a delivery apparatus, while still having a relatively soft distal tip at the point of entry into the patient's vessel.

As with other disclosed examples, the examples of sheath 66 shown in FIGS. 27A-28 can be provided in a wide range of sizes and dimensions. For example, the sheath 66 can be provided with an unexpanded inner diameter of from about 3 Fr to about 26 Fr. In some examples, the sheath 66 has an unexpanded inner diameter of from about 15 Fr to about 16 Fr. In some examples, the unexpanded inner diameter of the sheath 66 can range from about 3 Fr to about 26 Fr at or near the distal end of sheath 66, while the unexpanded inner diameter of the sheath 66 can range from about 3 Fr to about 28 Fr at or near the proximal end of sheath 66. For example, in one unexpanded example, the sheath 66 can transition from an unexpanded inner diameter of about 16 Fr at or near the distal end of the sheath 66 to an unexpanded inner diameter of about 26 Fr at or near the proximal end of the sheath 66.

The sheath 66 can be provided with an unexpanded outer diameter of from about 3 Fr to about 30 Fr, and, in some examples has an unexpanded outer diameter of from about 18 Fr to about 19 Fr. In some examples, the unexpanded outer diameter of the sheath 66 can range from about 3 Fr to about 28 Fr at or near the distal end of sheath 66, while the unexpanded outer diameter of the sheath 66 can range from about 3 Fr to about 30 Fr at or near the proximal end of sheath 66. For example, in one unexpanded example, the sheath 66 can transition from an unexpanded outer diameter of about 18 Fr at or near the distal end of the sheath 66 to an unexpanded outer diameter of about 28 Fr at or near the proximal end of the sheath 66.

The thickness of the inner polymeric layer 68 can vary, but in some preferred examples is from about 0.002 inches to about 0.015 inches. In some examples, expansion of the sheath 66 can result in expansion of the unexpanded outer diameter of from about 10% or less to about 430% or more.

As with other illustrated and described examples, the examples shown in FIGS. 27A-28 can be provided with a radiopaque filler and/or a radiopaque tip marker as described above. The sheath 66 can be provided with a radiopaque tip marker provided at or near the distal tip of the sheath 66. Such a radiopaque tip marker can comprise materials such as those suitable for the radiopaque filler, platinum, iridium, platinum/iridium alloys, stainless steel, other biocompatible metals, or combinations thereof.

Figure 51:
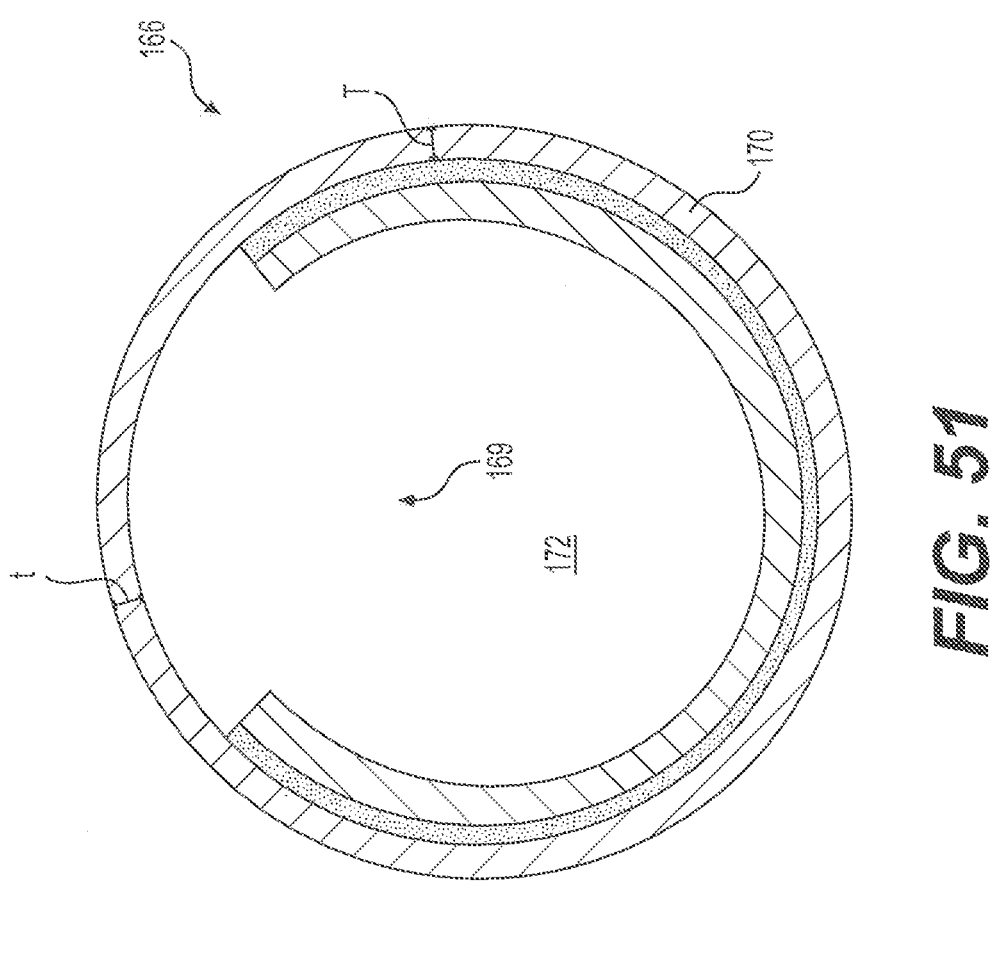
FIG. 51 is a section view of the sheath of FIG. 50 in an expanded configuration.
Figure 50:
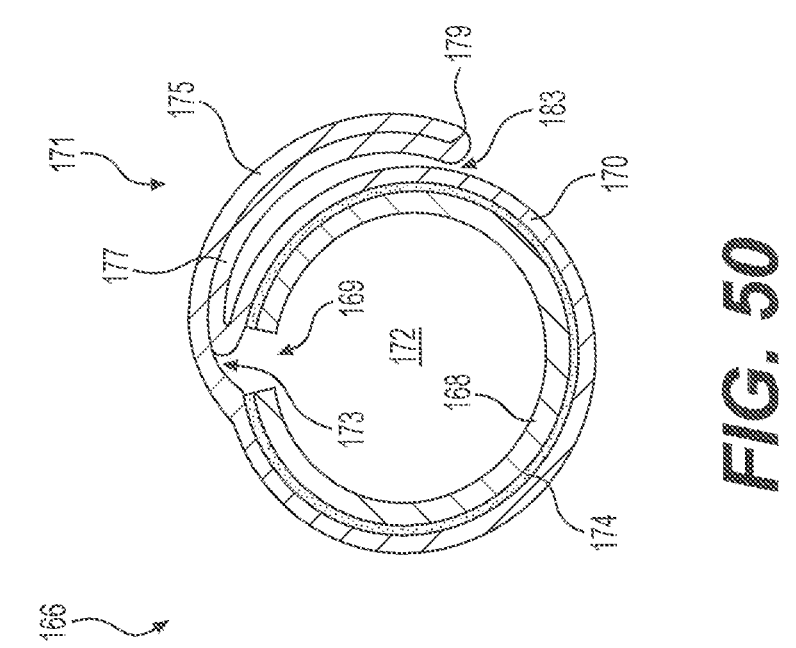
FIG. 50 is a section view of an example sheath in an unexpanded configuration.

FIGS. 50 and 51 show cross sectional views of an expandable sheath 166 having an inner tubular layer 168 with a longitudinal slit 169. In some examples, the longitudinal slit 169 extends the entire length of the inner tubular layer 168. An outer tubular layer 170 envelops the inner tubular layer 168 and includes a longitudinally extending, folded flap 171. In some examples, the folded flap 171 extends the entire length of the outer tubular layer 170. The folded flap 171 overlies a portion of the outer surface 183 of the outer tubular layer 170 when the sheath is in an unexpanded state (FIG. 50). When a prosthetic device is moved through an inner lumen 172 of the sheath 166, it applies an outwardly directed radial force on the inner tubular layer 168 that widens the longitudinal slit 169 and unfolds the folded flap 171. FIG. 51 shows the sheath 166 in the unexpanded state, with the longitudinal slit 169 widened and the outer tubular layer 170 unfolded.

The folded flap 171 of the outer tubular layer 170 has a base 173. The base 173 can be positioned radially outwardly from the longitudinal slit 169. In some examples, the base 173 is centered over the longitudinal slit 169. The folded flap 171 further includes a longitudinally extending overlying portion 175 extending from the base 173 to a longitudinally extending crease 179 at the edge of the flap 171. The longitudinally extending overlying portion 175 overlies a longitudinally extending underlying portion 177, and is separated from the underlying portion 177 by the crease 179. Underlying portion 177 contacts the outer surface 183 of the outer tubular layer 170 when the sheath is in an unexpanded state, as shown in FIG. 50.

Some examples of sheath 166 can include multiple longitudinally extending folded flaps that overlie portions of the outer surface 183 of the outer tubular layer 170, positioned at various locations around the circumference of sheath 166. For example, 2, 3, 4, 5, 6, 7, 8, 9, or 10 longitudinally extending folded flaps can be positioned around the circumference. In some examples, these multiple folded flaps are equally spaced around the circumference of the sheath 166.

The folded flap 171 extends circumferentially around a portion of the sheath 166. In some examples, the longitudinally extending flap 171 extends around about 20% to about 40% of the outer circumference of the outer tubular layer 170 when the sheath 166 is unexpanded (including about 20%, about 21%, about 22%, about 23%, about 24%, about 25%, about 26%, about 2272%, about 28%, about 29%, about 30%, about 31%, about 32%, about 33%, about 34%, about 35%, about 36%, about 37%, about 38%, about 39%, and about 40% of the outer circumference of the outer tubular layer 170). In one example, for a sheath having a 14F (4.7 millimeter) unexpanded outer diameter, the folded flap extends around 85 to 120 degrees, or about 23%-35%, of the outer circumference (resulting in inner lumen having an expanded diameter of about 7.6 millimeters to about 8.4 millimeters, which can be used with a valve having a 6.4 millimeter crimped outer diameter and a 26 millimeter expanded outer diameter).

In FIG. 51, the wall thickness of flap 171 is labeled t and the wall thickness of other parts of the outer tubular layer 170 are labeled T. In some examples, a portion of the flap 171 (such as, for example, the underlying portion 177 or the overlying portion 175) can have a wall thickness t that is thinner than a wall thickness (T) of other portions of the outer tubular layer. This variation in wall thickness promotes even column strength around the circumference of the sheath 166, which reduces kinking and minimizing the total outer diameter of the sheath. The wall thickness variation can also facilitate the folding process. In some examples, the entire flap 171 has a wall thickness t that is thinner than a wall thickness T of the remainder of the outer tubular layer. In one example, the wall thickness of t can be about from about 0.003 inches to about 0.007 inches, while the wall thickness of T can be from about 0.008 inches to about 0.012 inches. In other examples, such as the one shown in FIG. 51, the wall thickness t of flap 171 is about equal to the wall thickness T of the remainder of the outer tubular layer 170.

The outer tubular layer 170 is formed of a material having a low coefficient of friction, a high tensile modulus, and a high ultimate tensile strength in order to improve the push force transmission through the length of sheath 166 while reducing kinking. Good push force transmission means that the force applied by the practitioner to advance the sheath is predictable, responsive, and consistent along the length of the sheath. However, an excessively high tensile modulus may limit the ability of the longitudinally extending flap 171 to open, which could hamper push force transmission. A desirable range for the tensile modulus of the outer tubular layer 170 is from about 300 MPa to about 2,000 MPa (including about 300 MPa, about 400 MPa, about 500 MPa, about 600 MPa, about 700 MPa, about 800 MPa, about 900 MPa, about 1000 MPa, about 1100 MPa, about 1200 MPa, about 1300 MPa, about 1400 MPa, about 1500 MPa, about 1600 MPa, about 1700 MPa, about 1800 MPa, about 1900 MPa, and about 2000 MPa). In some examples, the tensile modulus may preferably be at least 700 MPa. High axial and radial stiffnesses enable the sheath to be easily inserted and to resist collapse within the body.

The ultimate tensile strength of the outer tubular layer 170 can be at least 50 MPa. A high ultimate tensile strength helps to prevent the material from tearing while the prosthetic device is advancing through the sheath.

Exemplary materials for formation of the outer tubular layer 170 of the examples shown in FIGS. 50 and 51 include high density polyethylene (HDPE), polyamide, co-polyamide, polyether block amide (PEBAX), or a blend of polyamide. Materials having shape memory properties are advantageous because the outer tubular layer 170 can be given a bias toward the folded state (for example, by heat setting). This facilitates refolding of the outer tubular layer 170 after passage of a prosthetic device. PEBAX is an exemplary shape memory material that may be heat set toward the folded state.

In some examples, the outer surface 183 of the outer tubular layer 170 can include a hydrophilic coating. In some examples, a bond can be created between the underlying portion 177 of the folded flap 171 and the outer surface 183 of the outer tubular layer 170. The bond can be a thermal bond (with portions of the contacting layers melted together), or it can be a separate layer of adhesive.

As discussed above, the inner tubular layer 168 of the examples shown in FIGS. 50 and 51 include a longitudinal slit 169. The inner tubular layer 168 includes a first longitudinally extending end 178 and a second longitudinally extending end 180, the first and second longitudinally extending ends 178, 180 defining the longitudinal slit 169.

The inner tubular layer 168 forms a low friction barrier between a passing prosthetic device and the higher friction outer tubular layer 170. The inner tubular layer 168 extends around at least 80% (or at least 85%, or at least 90%, or at least 95%) of the circumference of the inner lumen 172 when the sheath 166 is in an unexpanded state. This high degree of coverage limits contact between the passing prosthetic device and the higher friction outer tubular layer 170. In some examples, the coefficient of friction per ASTM D1894 of the inner tubular layer 168 (static or dynamic) is 0.30 or less. In other examples, the coefficient of friction is 0.25 or less.

In some examples, the low-friction inner tubular layer 168 includes, or is formed of, a material having a tensile modulus of at least about 300 MPa (and up to about 1400 MPa) to provide good push force transmission while providing kink resistance. This material could be, for example, high density polyethylene or a fluoropolymer. Exemplary fluoropolymers include polytetrafluoroethylene, ethylene fluorinated ethylene propylene, or perfluoro alkoxy.

A tie layer 174 can be positioned between the two layers, thereby adhering the inner tubular layer 168 to the outer tubular layer 170. The tie layer 174 can be formed of polyurethane or functionalized polyolefin, in some examples. In some examples, the contacting surface of the inner tubular layer 168 can be etched to improve bonding to the tie layer. For example, an inner tubular layer 168 that includes, or is formed of, a fluoropolymer might be etched on its outer surface to improve thermal bonding to the tie layer 174.

Figure 52:
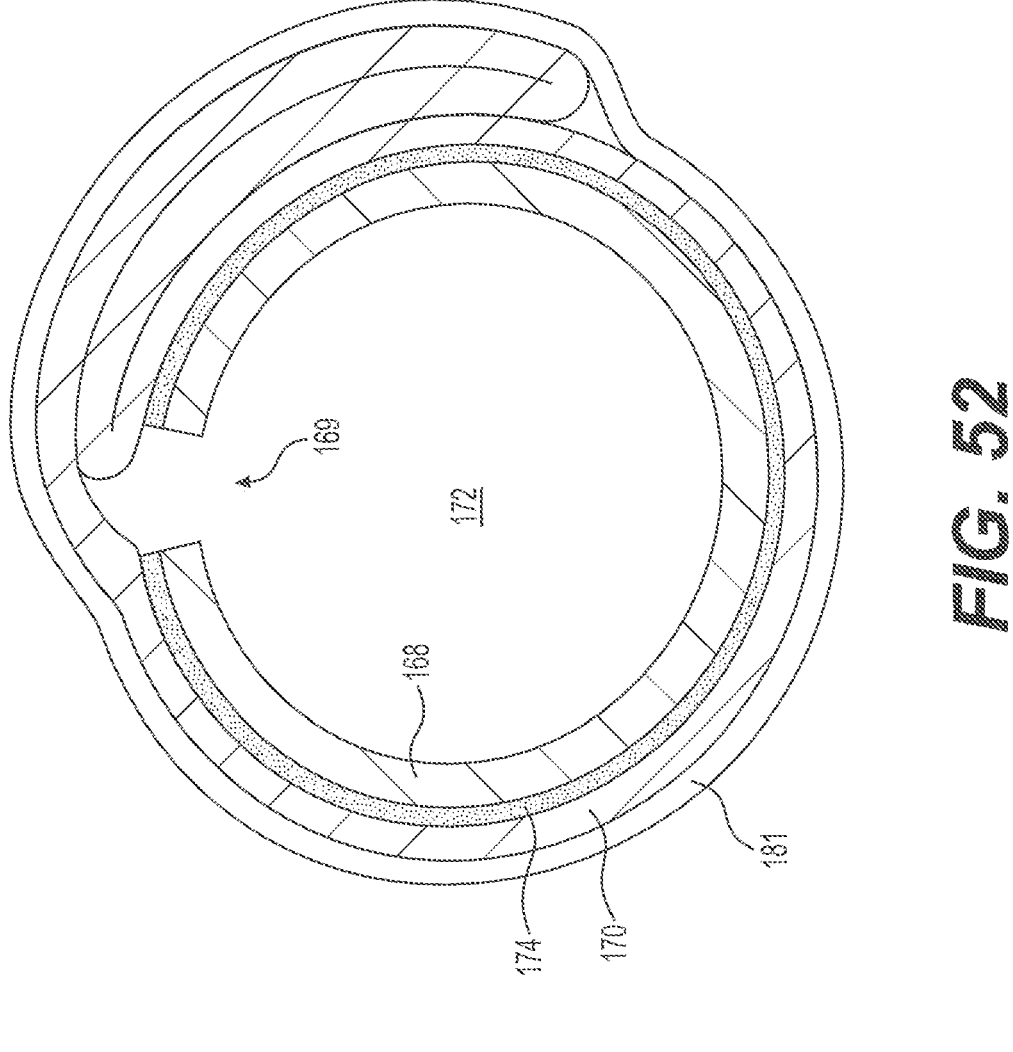
FIG. 52 is a section view of the sheath of FIG. 50 including an outer jacket.

Some examples of the sheath 166 shown in FIGS. 50 and 51 can also include an outer jacket 181, as shown in FIG. 52. The outer jacket 181 is elastomeric (having a relatively low tensile modulus compared to the inner and outer tubular layers 168, 170). As mentioned above, in some examples, the outer tubular layer 170 can be include, or can be formed of, a shape memory material (for example, a heat set polymer such as PEBAX) that facilitates refolding of the outer tubular layer 170 after expansion. In some examples, the sheath 166 can include an elastomeric outer jacket 181 that extends over and envelops the outer tubular layer 170. The outer jacket 181 and the shape memory feature can be used alone, or in conjunction with each other, to facilitate refolding (i.e., the elastomeric outer jacket 181 can extend over an outer tubular layer 170 that comprises a shape memory material). The refolding of the outer tubular layer 170 can preferably return the sheath 166 back to its original
outer diameter, or to a value close to the original outer
diameter (for example, to within about 10%, about 20%,
about 30%, about 40%, or about 50% of the original outer
diameter). The elastomeric outer jacket 181 can include, or
can be formed completely of, materials such as low durom-
eter polyurethane (for example, less than Shore 85 A),
styrene elastomer (for example, less than Shore 85 A), latex,
or low durometer PEBAX (for example, less than Shore
35D).

Methods of using the sheath of FIGS. 50-52 include first
inserting an expandable sheath 166 into the vasculature of a
subject and advancing the prosthetic device through an inner
lumen 172 of the expandable sheath 166. The prosthetic
device applies an outwardly directed radial force to the inner
tubular layer 168 of the expandable sheath 166. In some
examples, the outwardly directed radial force is transmitted
through the inner tubular layer 168, the tie layer 174, and the
outer tubular layer 170. The outwardly directed radial force
widens a longitudinal slit 169 in the inner tubular layer 168.
The widening of the longitudinal slit 169 travels the full
length of the expandable sheath, in some examples.

The outwardly directed radial force further unfolds the
longitudinally extending flap 171 of the outer tubular layer
170 to expand the expandable sheath. The unfolding of the
flap 171 can include sliding a longitudinally extending
overlying portion 175 circumferentially against a longitudi-
nally extending underlying portion 177 of flap 171. The
underlying portion 177 can slide circumferentially against
an outer surface 183 of the outer tubular layer 170. In some
examples, the unfolding of the longitudinally extending flap
171 occurs at a position radially outward from the longitu-
dinal slit 169 of the inner tubular layer 168. The unfolding
of the flap 171 can extend the full length of the expandable
sheath 166, in some examples.

The longitudinal slit 169 of the inner tubular layer 168
narrows once the outwardly directed radial force has ceased
(i.e., once the prosthetic device has passed by). The slit 169
may narrow back to its original width, or to a value close to
the original width (for example, to a value within 10% of the
original width). The narrowing can occur along the entire
length of the sheath 166. The prosthetic device is then
delivered to the procedure site.

The longitudinally extending flap 171 at least partially
refolds once the prosthetic device ceases to apply the
outwardly directed radial force (i.e., once it has passed by).
In some examples, the longitudinally extending flap 171
refolds itself due to a shape memory bias toward the folded
state. In some examples, an inwardly directed radial force is
applied to the outer surface 183 of the outer tubular layer
170 to refold the longitudinally extending flap 171 (for
example, by elastomeric outer jacket 181).

An example method of making the sheath is as follows.
These steps are not meant to be limiting. The steps given can
be reordered as needed. Other steps can be added, or in other
examples, some steps may not be necessary. Sizes are
approximate. 1) Start with a PTFE inner layer of about 0.200
inch inner diameter (ID), wall thickness about 0.004 inches,
2) load PTFE inner layer on to a tapering mandrel from
about 0.200 inches to about 0.187 inches, 3) stretch on to an
0.187 inch outer diameter (OD) mandrel section under heat,
4) flare proximal end of 0.200 inch ID PTFE to 0.340 inches
ID under heat, 5) load tie layer such as Tecoflex 80A having
about 0.200 inch ID and 0.004 inch wall thickness over the
PTFE inner layer along the body section (optionally the tie
layer can be applied after expanding the inner layer with air
pressure), 6) adhere tie layer to inner layer, for example, by covering it with FEP (fluorinated ethylene propylene) heat
shrink tubing and applying heat, 7) remove FEP thermal
shrink tubing if it was used, 8) create a longitudinal slit along
the body section of the assembly, 9) load the subassembly
having a slit on to a 0.187 inch OD mandrel, 10) load outer
layer over the body, 11) fold outer layer, 12) heat set the fold,
for example, by inserting the subassembly with a fold inside
a heat shrink tubing and placing the assembly into the oven,
13) remove the shrink tubing if it was used, 14) remove
sheath from the mandrel. In some examples, an outer
elastomeric jacket is added over the heat set outer layer prior
to removal from the mandrel.

FIGS. 29A-29D show section views of other possible
configurations of a sheath 66 for introducing a prosthetic
device into a patient's vasculature. The sheath 66 comprises
a polymeric tubular layer 84 having an inner surface 86 and
an outer surface 88. The thickness of the polymeric tubular
layer 84 extends from the inner surface 86 to the outer
surface 88. As shown in FIGS. 29B-29D, the polymeric
tubular layer 84 can be formed with at least a first angular
portion 90 of reduced thickness adjacent the inner surface 86
and a second angular portion 92 of reduced thickness
adjacent the outer surface 88, with the second portion 92 at
least partially overlapping the first portion 90. FIG. 29A
illustrates a similar configuration, where a second portion 92
at least partially overlaps a first portion 90 in a partial coil
configuration. In the example of FIG. 29A, the second
portion 92 and the first portion 90 can have the same
thickness.

In preferred examples, the first and second portions 90, 92
are not adhered to one another. In some examples, and best
seen in FIG. 29A, there can be a small gap 94 between the
first and second portions 90, 92 that can give the sheath 66
the appearance of having two interior lumens 72, 94. FIGS.
29A-29D illustrate the sheath 66 in unexpanded configura-
tions. Preferably, upon expansion of the sheath 66, the ends
of the first and second portions 90, 92 abut or are in close
proximity to each other to reduce or eliminate any gap
between them.

Figure 33:
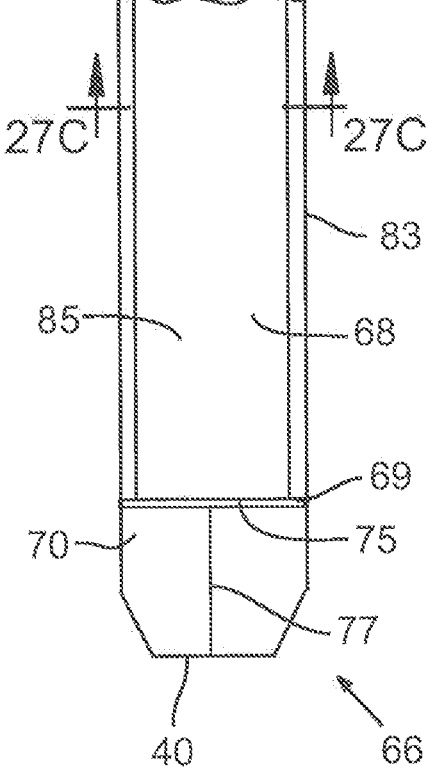
FIG. 33 illustrates a plan view of one example of a sheath having a partial slit or score line.

In some examples, a sheath 66 can comprise a partial slit
or score line along at least a portion of its length. For
example, as shown in FIG. 33, a sheath 66 can comprise an
outer polymeric tubular layer 70 over an inner polymeric
layer 68. The inner polymeric layer can extend through a cut
in the outer polymeric tubular layer 70, to form a folded
region 85 on the outer surface of the outer polymeric tubular
layer 70, such as also shown in FIG. 27C. The folded region
85 of the inner layer, in some examples, terminates before
the outer polymeric tubular layer 70 (i.e., the outer poly-
meric tubular layer 70 is longer than the inner layer). As
shown in FIG. 33, in these examples, the sheath 66 can
comprise a partial slit or score line 77 that can extend from
the termination (distal end) 75 of the folded region 85 to the
distal end 40 of the sheath 66. In some examples, score line
77 can facilitate expansion of the sheath 66.

Figure 34:
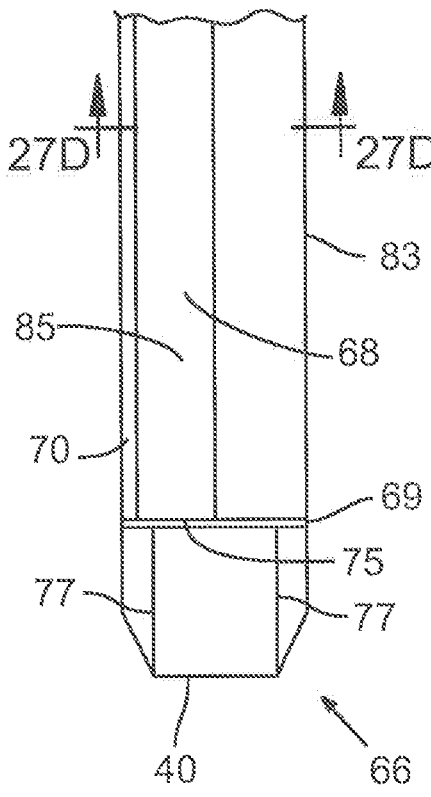
FIG. 34 illustrates a plan view of another example of a sheath having a partial slit or score line.

Score line 77 can be substantially centrally located with
respect to the folded region 85. In alternative examples,
score line 77 can be positioned in other locations relative to
the folded region 85. Also, sheath 66 can comprise one or
more score lines 77. For example, as shown in FIG. 34, one
or more score lines 77 can be peripherally located with
respect to the folded region 85. The one or more score lines
77 can be positioned anywhere around the circumference of
the outer polymeric tubular layer 70. In examples compris-
ing a radiopaque marker 69 as seen in FIG. 33, a score line 77 can extend from, for example, the distal end of the radiopaque marker 69 substantially to the distal end 40 of the sheath 66.

Figures 35, 36:
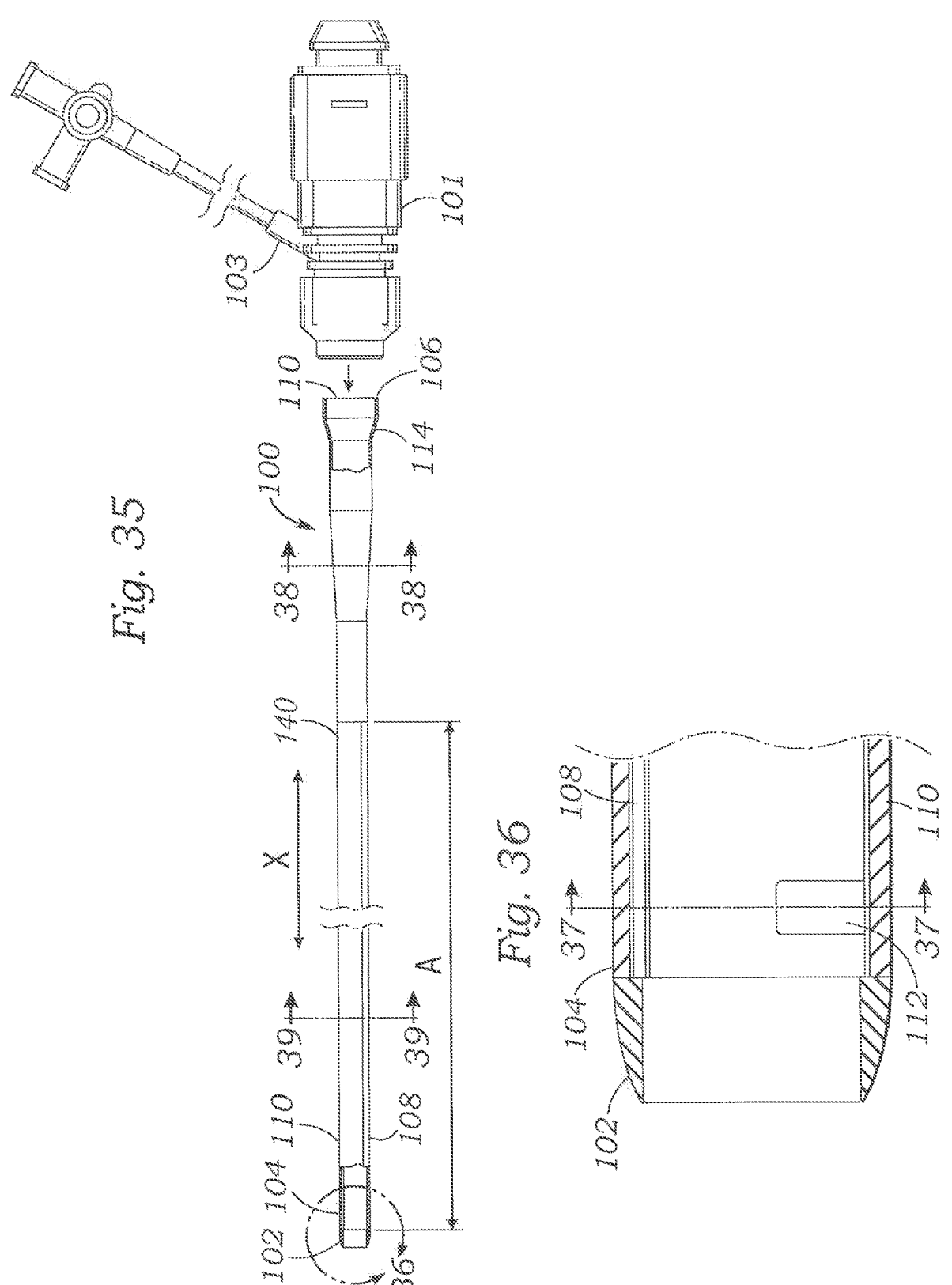
FIG. 35 is an elevation view of an expandable sheath according to the present disclosure and a representative housing.
FIG. 36 is an enlarged cutaway view of the distal end of the sheath of FIG. 35.

FIGS. 35 and 36 illustrate an expandable sheath 100 according to the present disclosure, which can be used with a delivery apparatus for delivering a prosthetic device, such as a tissue heart valve into a patient. In general, the delivery apparatus can include a steerable guide catheter (also referred to as a flex catheter), a balloon catheter extending through the guide catheter, and a nose catheter extending through the balloon catheter (e.g., as depicted in FIG. 1). The guide catheter, the balloon catheter, and the nose catheter can be adapted to slide longitudinally relative to each other to facilitate delivery and positioning of the valve at an implantation site in a patient's body. However, it should be noted that the sheath 100 can be used with any type of elongated delivery apparatus used for implanting balloon-expandable prosthetic valves, self-expanding prosthetic valves, and other prosthetic devices. Generally, sheath 100 can be inserted into a vessel (e.g., the femoral or iliac arteries) by passing through the skin of patient, such that a soft tip portion 102 at the distal end 104 of the sheath 100 is inserted into the vessel. The sheath 100 can also include a proximal flared end portion 114 to facilitate mating with an introducer housing 101 and catheters mentioned above (e.g., the proximal flared end portion 114 can provide a compression fit over the housing tip and/or the proximal flared end portion 114 can be secured to the housing 101 via a nut or other fastening device or by bonding the proximal end of the sheath to the housing). The introducer housing 101 can house one or more valves that form a seal around the outer surface of the delivery apparatus once inserted through the housing, as known in the art. The delivery apparatus can be inserted into and through the sheath 100, allowing the prosthetic device to be advanced through the patient's vasculature and implanted within the patient.

Sheath 100 can include a plurality of layers. For example, sheath 100 can include an inner layer 108 and an outer layer 110 disposed around the inner layer 108. The inner layer 108 can define a lumen through which a delivery apparatus can travel into a patient's vessel in order to deliver, remove, repair, and/or replace a prosthetic device, moving in a direction along the longitudinal axis X. As the prosthetic device passes through the sheath 100, the sheath locally expands from a first, resting diameter to a second, expanded diameter to accommodate the prosthetic device. After the prosthetic device passes through a particular location of the sheath 100, each successive expanded portion or segment of the sheath 100 at least partially returns to the smaller, resting diameter. In this manner, the sheath 100 can be considered self-expanding, in that it does not require use of a balloon, dilator, and/or obturator to expand.

The inner and outer layers 108, 110 can comprise any suitable materials. Suitable materials for the inner layer 108 include polytetrafluoroethylene (PTFE), ethylene tetrafluoroethylene (ETFE), nylon, polyethylene, polyether block amide (e.g., Pebax), and/or combinations thereof. In one specific example the inner layer 108 can comprise a lubricious, low-friction, or hydrophilic material, such as PTFE. Such low coefficient of friction materials can facilitate passage of the prosthetic device through the lumen defined by the inner layer 108. In some examples, the inner layer 108 can have a coefficient of friction of less than about 0.1. Some examples of a sheath 100 can include a lubricious liner on the inner surface of the inner layer 108. Examples of suitable lubricious liners include materials that can further reduce the coefficient of friction of the inner layer 108, such as PTFE, polyethylene, polyvinylidene fluoride, and combinations thereof. Suitable materials for a lubricious liner also include other materials desirably having a coefficient of friction of about 0.1 or less.

Suitable materials for the outer layer 110 include nylon, polyethylene, Pebax, HDPE, polyurethanes (e.g., Tecoflex™), and other medical grade materials. In one example, the outer layer 110 can comprise high density polyethylene (HDPE) and Tecoflex™ (or other polyurethane material) extruded as a composite. In some examples, the Tecoflex™ can act as an adhesive between the inner layer 108 and the outer layer 110 and may only be present along a portion of the inner surface of the outer layer 110. Other suitable materials for the inner and outer layers are also disclosed in U.S. Patent Application Publication No. 2010/0094392, which is incorporated herein by reference.

Additionally, some examples of a sheath 100 can include an exterior hydrophilic coating on the outer surface of the outer layer 110. Such a hydrophilic coating can facilitate insertion of the sheath 100 into a patient's vessel. Examples of suitable hydrophilic coatings include the Harmony™ Advanced Lubricity Coatings and other Advanced Hydrophilic Coatings available from SurModics, Inc., Eden Prairie, MN. DSM medical coatings (available from Koninklijke DSM N.V, Heerlen, the Netherlands), as well as other hydrophilic coatings (e.g., PTFE, polyethylene, polyvinylidine fluoride), are also suitable for use with the sheath 100.

Best seen in FIG. 36, the soft tip portion 102 can comprise, in some examples, low density polyethylene (LDPE) and can be configured to minimize trauma or damage to the patient's vessels as the sheath is navigated through the vasculature. For example, in some examples, the soft tip portion 102 can be slightly tapered to facilitate passage through the vessels. The soft tip portion 102 can be secured to the distal end 104 of the sheath 100, such as by thermally bonding the soft tip portion 102 to the inner and outer layers of the sheath 100. Such a soft tip portion 102 can be provided with a lower hardness than the other portions of the sheath 100. In some examples, the soft tip portion 102 can have a Shore hardness from about 25 D to about 40 D. The tip portion 102 is configured to be radially expandable to allow a prosthetic device to pass through the distal opening of the sheath 100. For example, the tip portion 102 can be formed with a weakened portion, such as an axially extending score line or perforated line that is configured to split and allow the tip portion to expand radially when the prosthetic device passes through the tip portion (such as shown in the examples of FIGS. 33 and 34).

Figure 37:
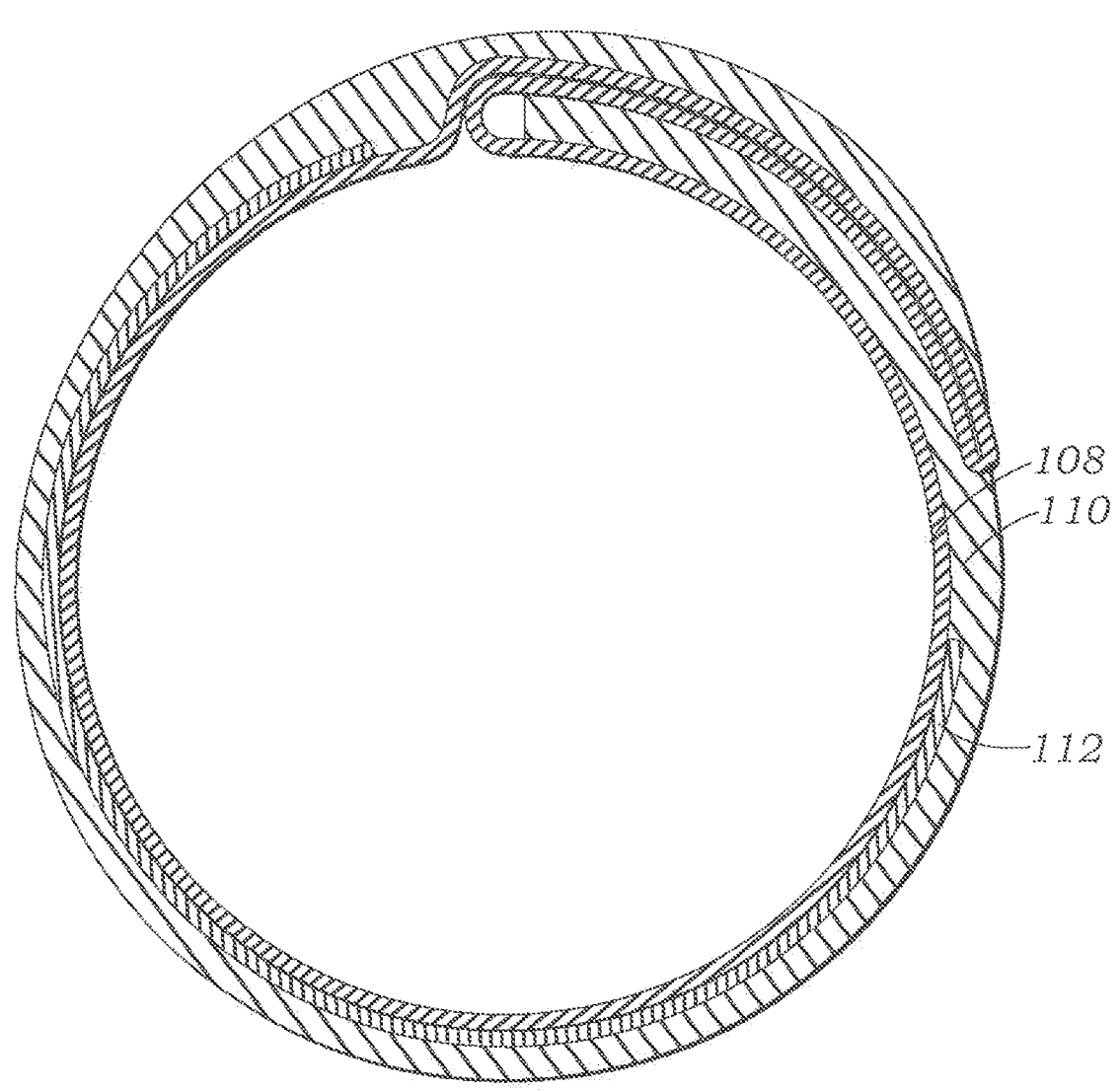
FIG. 37 is a section view of the distal end of the sheath of FIG. 35, taken along line 37-37 in FIG. 36.

FIG. 37 shows a cross-section view of the sheath 100 taken near the distal end 104 of the sheath 100. As shown in FIGS. 36 and 37, the sheath 100 can include at least one radiopaque filler or marker, such as a discontinuous, or C-shaped, band positioned near the distal end 104 of the sheath 100. The marker 112 can be associated with the inner and/or outer layers 108, 110 of the sheath 100. For example, as shown in FIG. 37, the marker 112 can be positioned between the inner layer 108 and the outer layer 110. In alternative examples, the marker 112 can be associated with the outer surface of the outer layer 110. In some examples, the marker 112 can be embedded or blended within the inner or outer layers 108, 110.

The C-shaped band/marker 112 can serve as a radiopaque marker or filler, to enable visibility of the sheath 100 under fluoroscopy during use within a patient. The C-shaped band/marker 112 can comprise any suitable radiopaque material, such as barium sulfite, bismuth trioxide, titanium dioxide, bismuth subcarbonate, platinum, iridium, and combinations thereof. In one specific example, the C-shaped band can comprise 90% platinum and 10% iridium. In other examples, the marker 112 need not be a C-shaped band. Other shapes, designs, and configurations are possible. For example, in some examples, the marker 112 can extend around the entire circumference of the sheath 100. In other examples, the marker 112 can comprise a plurality of small markers spaced around the sheath 100.

Figure 38:
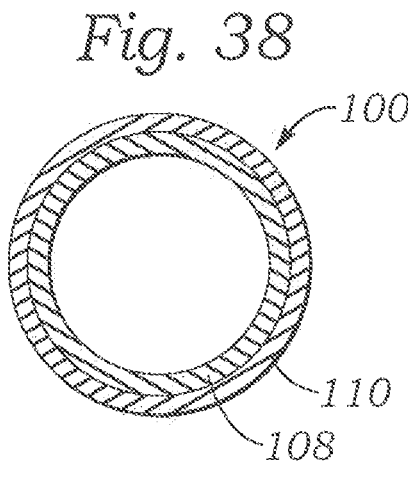
FIG. 38 is a section view of a proximal section of the sheath of FIG. 35, taken along line 38-38 in FIG. 35.
Figure 39:
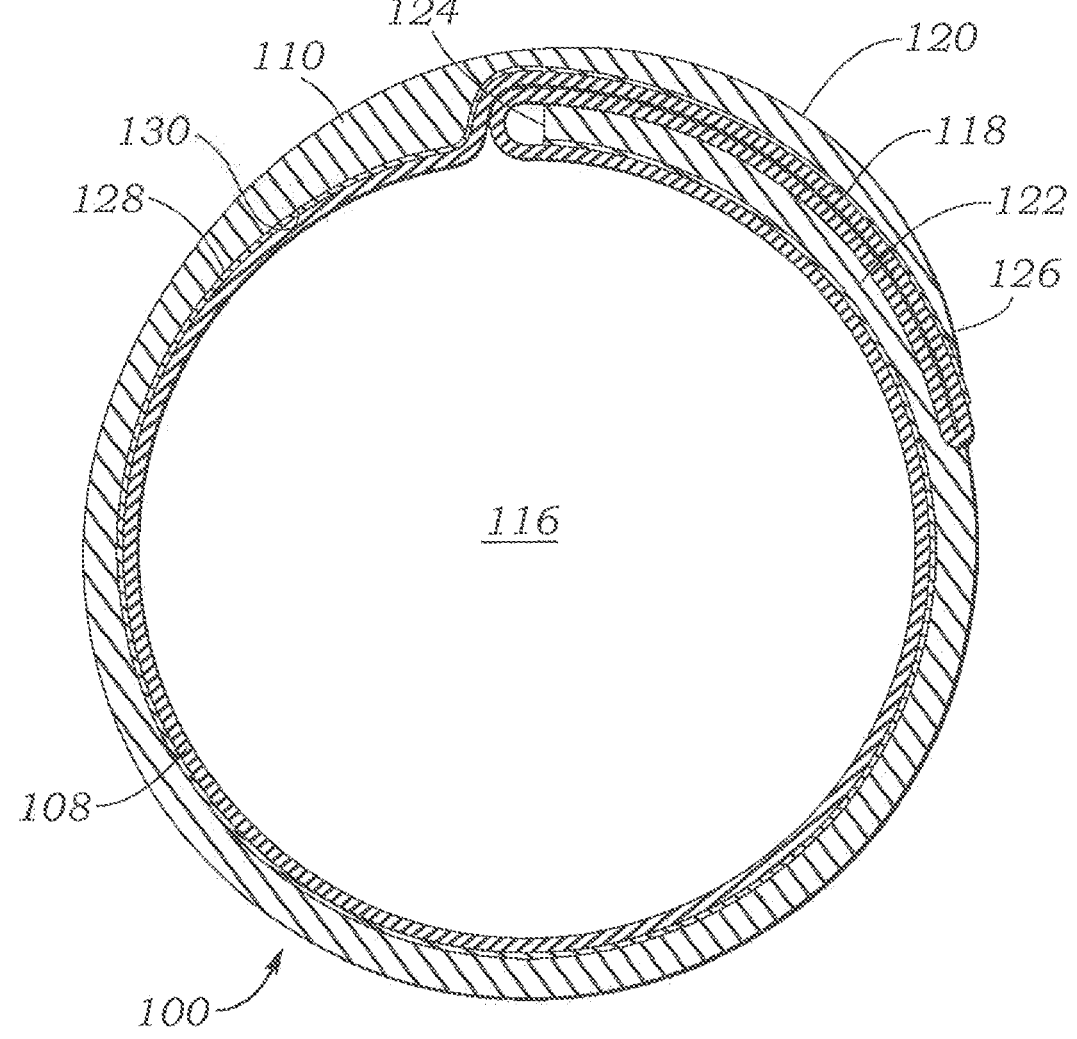
FIG. 39 is a section view of the sheath of FIG. 35 in a rest (unexpanded) configuration, taken along line 39-39 in FIG. 35.

FIGS. 38 and 39 show additional cross sections taken at different points along the sheath 100. FIG. 38 shows a cross-section of a segment of the sheath near the proximal end 106 of the sheath 100, as indicated by line 38-38 in FIG. 35. The sheath 100 at this location can include inner layer 108 and outer layer 110. At this location, near the proximal end of the sheath, the layers 108, 110 can be substantially tubular, without any slits or folded portions in the layers. By contrast, the layers 108, 110 at different locations along the sheath 100 (e.g., at the point indicated by line 39-39 in FIG. 35) can have a different configuration.

As shown in FIG. 39, the inner layer 108 can be arranged to form a substantially cylindrical lumen 116 therethrough. Inner layer 108 can include one or more folded portions 118. In the example shown in FIG. 39, inner layer 108 is arranged to have one folded portion 118 that can be positioned on either side of the inner layer 108. The folded portion 118 includes a first fold (e.g., a longitudinally extending fold line) and a second fold and an overlapping portion extending circumferentially therebetween (when the sheath is in an unexpanded configuration). As illustrated in FIG. 39, the folded portion 118 comprises an overlap in a radial direction of at least two thicknesses of the inner layer 108. Inner layer 108 can be continuous, in that there are no breaks, slits, or perforations in inner layer 108. Outer layer 110 can be arranged in an overlapping fashion such that an overlapping portion 120 overlaps at least a part of the folded portion 118 of the inner layer 108. As shown in FIG. 39, the overlapping portion 120 also overlaps an underlying portion 122 of the outer layer 110. The underlying portion 122 can be positioned to underlie both the overlapping portion 120 of the outer layer 110, as well as the folded portion 118 of the inner layer 108. Thus, the outer layer 110 can be discontinuous, in that it includes a slit or a cut in order to form the overlapping and underlying portions 120, 122. In other words, a first edge 124 of the outer layer 110 is spaced apart from a second edge 126 of the outer layer 110 so as not to form a continuous layer.

As shown in FIG. 39, the sheath 100 can also include a thin layer of bonding or adhesive material, also referred to as a tie layer and/or adhesive layer, positioned between the inner and outer layers 108, 110. In one example, the adhesive layer 128 can comprise a polyurethane material such as Tecoflex™ or etched PTFE tubing. The adhesive layer 128 can be positioned on an inner surface 130 of at least a portion of the outer layer 110 so as to provide adhesion between selected portions of the inner and outer layers 108, 110. For example, the outer layer 110 may only include an adhesive layer 128 around the portion of the inner surface 130 that faces the lumen-forming portion of the inner layer 108. In other words, the adhesive layer 128 can be positioned so that it does not contact the folded portion 118 of the inner layer 108 in some examples. In other examples, the adhesive layer 128 can be positioned in different configurations as desired for the particular application. For example, as shown in FIG. 39, the adhesive layer 128 can be positioned along the entire inner surface 130 of the outer layer 110. In an alternative example, the adhesive layer can be applied to the outer surface of the inner layer 108 instead of the inner surface of the outer layer. The adhesive layer 128 can be applied to all or selected portions on the inner layer 108; for example, the adhesive layer 128 can be formed only on the portion of the inner layer that faces the lumen-forming portion of the outer layer and not on the folded portion. The configuration of FIG. 39 allows for radial expansion of the sheath 100 as an outwardly directed radial force is applied from within (e.g., by passing a medical device such as a prosthetic heart valve through the lumen 116). As radial force is applied, the folded portion 118 can at least partially separate, straighten, and/or unfold, and/or the overlapping portion 120 and the underlying portion 122 of the outer layer 110 can slide circumferentially with respect to one another, thereby allowing the diameter of lumen 116 to enlarge.

Figure 40:
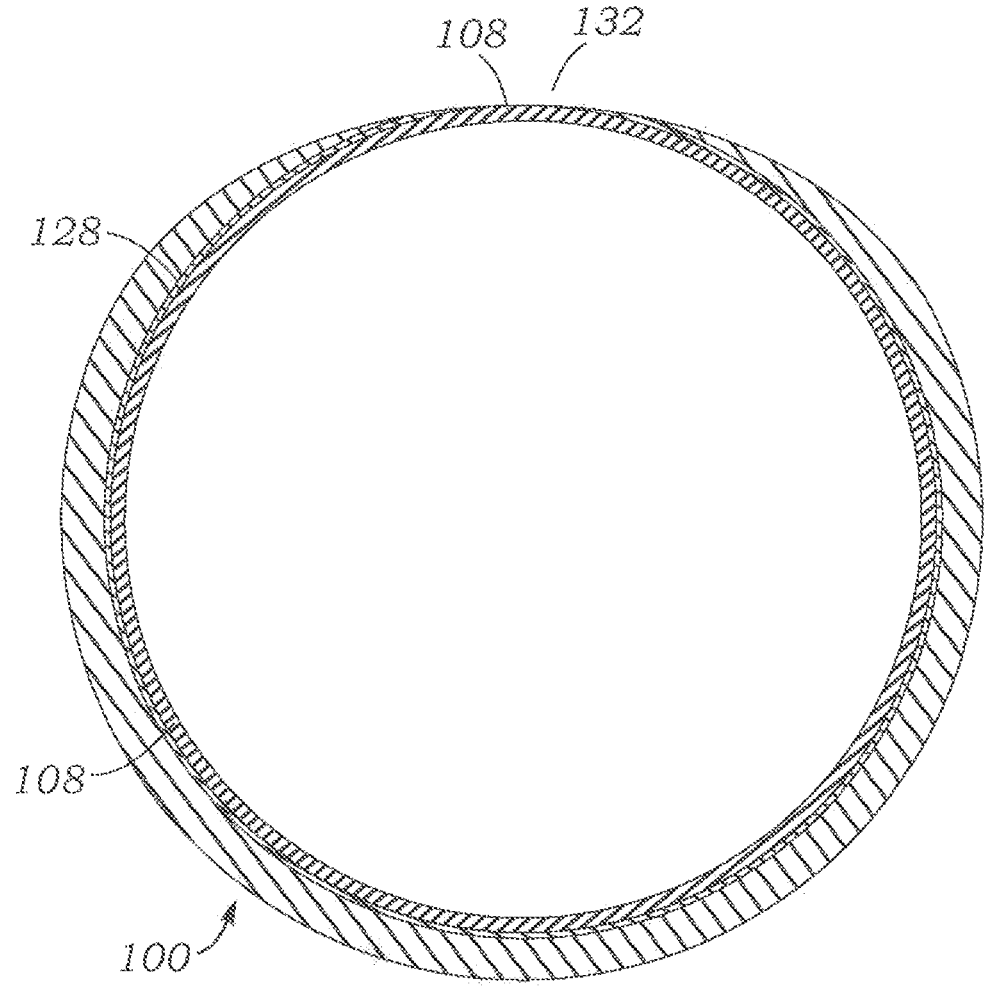
FIG. 40 is the section view of the sheath of FIG. 39, in an expanded configuration.

In this manner, the sheath 100 is configured to expand from a resting configuration (FIG. 39) to an expanded configuration shown in FIG. 40. In the expanded configuration, as shown in FIG. 40, an annular gap 132 can form between the longitudinal edges of the overlapping portion 120 and the underlying portion 122 of the outer layer 110. As the sheath 100 expands at a particular location (i.e., locally expands at the location of the passing prosthetic device), the overlapping portion 120 of the outer layer 110 can move circumferentially with respect to the underlying portion 122 as the folded portion 118 of the inner layer 108 unfolds. This movement can be facilitated by the use of a low-friction material for inner layer 108, such as PTFE. Further, the folded portion 118 can at least partially separate and/or unfold to accommodate a medical device having a diameter larger than that of lumen 116 in the resting configuration. As shown in FIG. 40, in some examples, the folded portion of the inner layer 108 can completely unfold, so that the inner layer 108 forms a cylindrical tube at the location of the expanded configuration.

The sheath 100 can be configured such that it locally expands at a particular location corresponding to the location of the medical device along the length of the lumen 116, and then locally contracts once the medical device has passed that particular location. Thus, a bulge may be visible, traveling longitudinally along the length of the sheath as a medical device is introduced through the sheath, representing continuous local expansion and contraction as the device travels the length of the sheath 100. In some examples, each segment of the sheath 100 can locally contract after removal of any radial outward force such that it regains the original resting diameter of lumen 116. In some examples, each segment of the sheath 100 can locally contract after removal of any radial outward force such that it at least partially returns to the original resting diameter of lumen 116.

The layers 108, 110 of sheath 100 can be configured as shown in FIG. 39 along at least a portion of the length of the sheath 100. In some examples, the layers 108, 110 can be configured as shown in FIG. 39 along the length A (FIG. 35) extending from a location adjacent the soft tip portion 102 to a location closer to the proximal end 106 of the sheath 100. In this matter, the sheath is expandable and contractable only along a portion of the length of the sheath corresponding to length A (which typically corresponds to the section of the sheath inserted into the narrowest section of the patient's vasculature).

Figure 54:
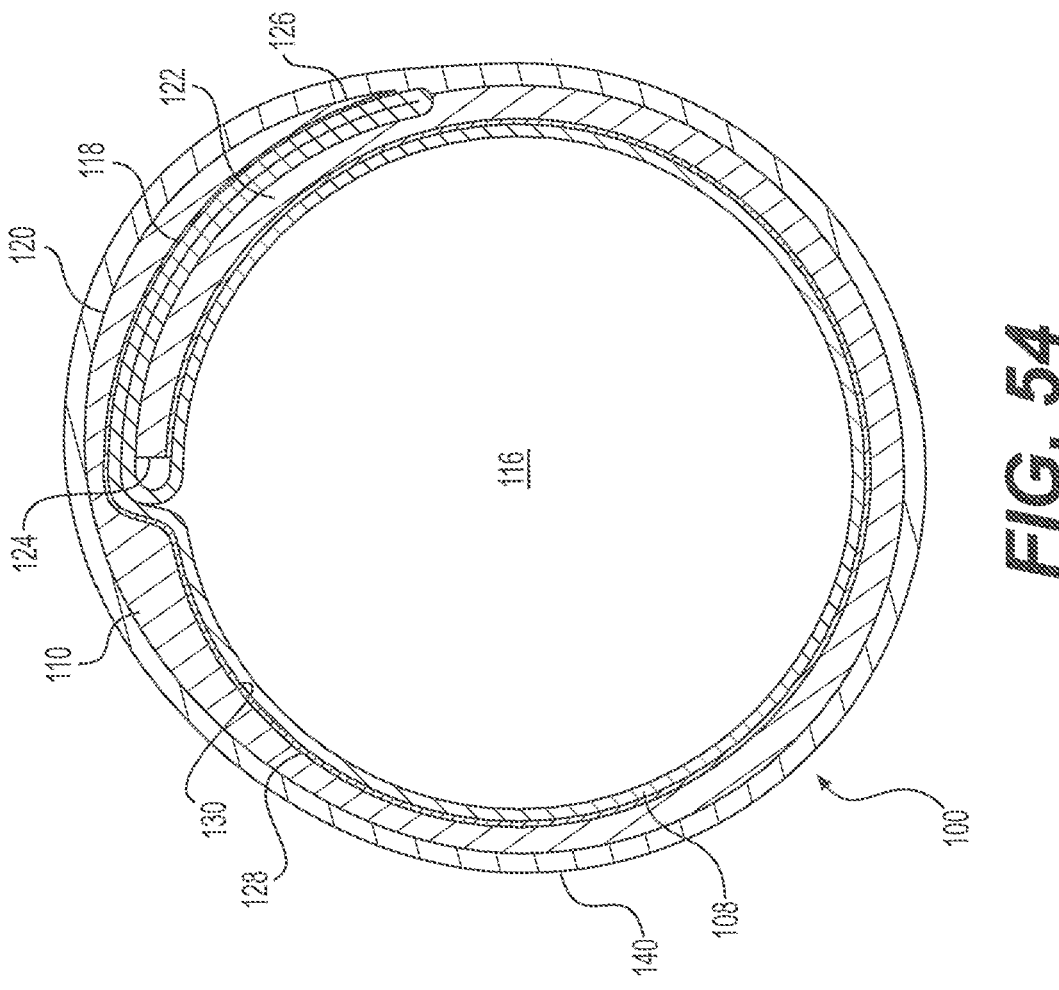
FIG. 54 is a section view of the sheath of FIG. 53 in a rest (unexpanded) configuration, taken along line 39-39 in FIG. 35.
Figure 53:
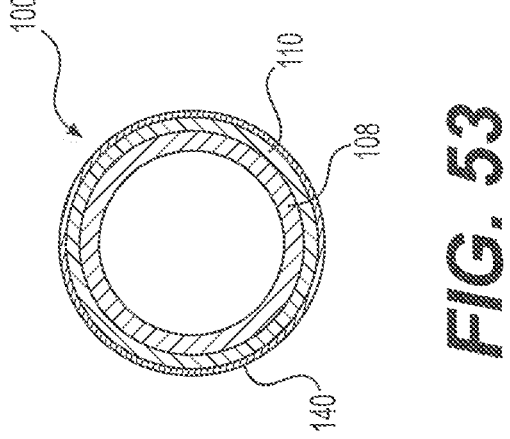
FIG. 53 is a section view of the sheath of FIG. 35 in a rest (unexpanded) configuration including an outer jacket, taken along line 39-39 in FIG. 35.

In some aspects, the sheath 100 (e.g., sheath 100 of FIG. 35) can include an outer jacket 140 extending over the outer layer 110. FIGS. 53 and 54 show additional cross sections taken at different points along the sheath 100 showing the outer jacket 140. Similar to FIG. 38, FIG. 53 shows a cross-section of a segment of the sheath near the proximal end 106 of the sheath 100, as indicated by line 38-38 in FIG.

35. The sheath 100 at this location can include inner layer 108, outer layer 110, adhesive layer 128, and an outer jacket 140. At this location, near the proximal end of the sheath, the layers 108, 110 and outer jacket 140 can be substantially tubular, without any slits or folded portions in the layers. By contrast, the layers 108, 110 at different locations along the sheath 100 (e.g., at the point indicated by line 39-39 in FIG. 35) can have a different configuration, while the outer jacket 140 maintains a substantially tubular shape, without slits or folds.

Figure 55:
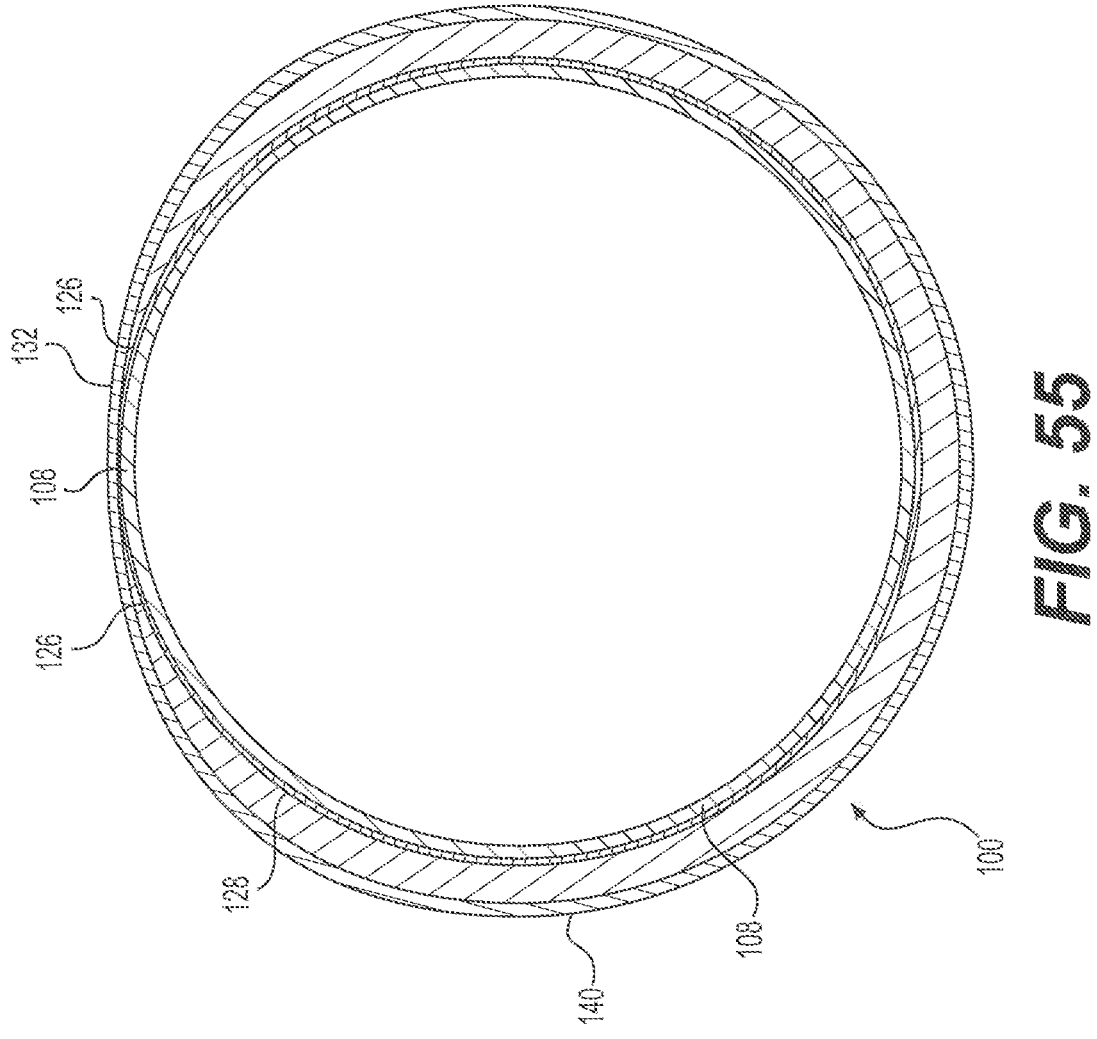
FIG. 55 is a section view of the sheath of FIG. 54, in an expanded configuration.

As shown in FIG. 54, and described above with respect to FIG. 39, the inner layer 108 can be arranged to form a substantially cylindrical lumen 116 extending therethrough. The inner layer 108 can include one or more folded portions 118. The outer layer 110 can be arranged in an overlapping fashion such that an overlapping portion 120 overlaps at least a part of the folded portion 118 of the inner layer 108 as well as the underlying portion 122 (positioned to underlie the folded portion 118 of the inner layer 108) when the sheath is unexpanded. The sheath 100 is configured to locally expand from an unexpanded configuration in which the lumen 116 has a first diameter to an expanded configuration in which the lumen 116 has a second diameter larger than the first diameter. The sheath 100 expands in response to an outwardly directed radial force exerted by a medical device against the inner layer 108 as it passes through the lumen 116. During expansion, the first fold/folded edge moves closer to the second fold/folded edge to shorten the folded portion 118. As shown in FIG. 55, in some examples, the folded portion 118 of the inner layer 108 can completely unfold, so that the inner layer 108 forms a cylindrical tube at the location of the expanded configuration. When the sheath is expanded, a portion of the inner layer 108 extends through the opening/gap provided in the outer layer 110, where the opening is formed by the longitudinally extending edge of the overlapping portion 120 and a longitudinally extending edge of the underlying portion 122. As the prosthetic device passes, the sheath 100 then locally contracts at least partially back to the unexpanded configuration.

As described above, the sheath 100 includes an inner layer 108. The inner layer 108 can be surface treated, such as by plasma etching, chemical etching or other suitable methods of surface treatment. By treating the surface of the inner layer 108, the outer surface of the inner layer 108 can have areas with altered surface angles that can provide better adhesion between the inner layer 108 and the outer layer 110. As described above, the inner layer 108 can comprise polytetrafluoroethylene (PTFE), polyimide, polyetheretherketone (PEEK), polyurethane, nylon, polyethylene, polyamide, or combinations thereof. In an example sheath 100, the inner layer 108 is composed of an etched PTFE material. It is contemplated that the inner layer 108 can have a fully etched outer surface or a partially etched outer surface. When partially etched, the unetched portions of the outer surface of the inner layer 108 can extend longitudinally along a length of the inner layer 108 and/or circumferentially around the circumference of the inner layer 108. For example, desired unetched location on the inner layer 108 can be masked or otherwise covered during the etching process to prevent etching at that location. It is also contemplated that the entire outer surface of the inner layer 108 can be etched and the etching removed at the desired locations of unetched surface.

In an example sheath 100, unetched portions are provided along those surfaces of the inner layer 108 that come into contact with the outer surface of the outer layer 110. That is, those portions of the inner layer 108 excluding the adhesive layer 128 would not include etching. For example, it is contemplated that etching is not included between the inner surface of the folded portion 118 of the inner layer 108 and the underlying portion 122 of the outer layer 110. By excluding etching on the portions where the inner layer 108 and the outer surface of the outer layer 110 are in direct contact helps to facilitate release of the inner surface of the folded portion 118 and the outer layer 110 during expansion of the sheath 100.

The wall thickness of the inner layer can vary, but in some examples the wall thickness of the inner layer 108 ranges between about 0.002 inches and about 0.006 inches (including about 0.002 inches, about 0.003 inches, about 0.004 inches, about 0.005 inches, about 0.006 inches). In other examples the wall thickness of the inner layer ranges between about 0.003 includes and about 0.005 inches. In a further example, the wall thickness of the inner layer 108 ranges between about 0.0035 inches and about 0.0045 inches (including about 0.0035 inches, about 0.0040 inches, about 0.0045 inches).

As described above, the sheath 100 includes an outer layer 110 exerting a radially inward force on the inner layer 108. In general, the outer layer 110 can comprise a polymeric material. As described above, the outer layer 110 can be comprised of PTFE, polyimide, PEEK, polyurethane, nylon, polyethylene, polypropylene, polyamide, polyether block amides, polyether block ester copolymer, thermoset silicone, latex, poly-isoprene rubbers, high density polyethylene (HDPE), Tecoflex™, or combinations thereof. In an exemplary example, the inner layer 108 can comprise PTFE and the outer layer 110 can comprise a combination of HDPE and Tecoflex™. The outer layer 110 can have a wall thickness ranging between about 0.007 inches and about 0.013 inches (including 0.007 inches, about 0.008 inches, about 0.009 inches, about 0.010 inches, about 0.011 inches, about 0.012 inches, about 0.013 inches). In another example, the outer layer 110 can have a wall thickness ranging between about 0.008 inches and about 0.012 inches. In another example, the outer layer 110 can have a wall thickness ranging between about 0.009 inches and about 0.011 inches.

As described above, in some aspects, the sheath 100 includes an outer jacket 140 that extends over and envelopes the outer layer 110. While the outer layer 110 can be discontinuous, in that it includes a slit or a cut in order to form the overlapping and underlying portions 120, 122 as described above, the outer jacket 140 can include a continuous outer layer covering the inner and outer layers 108, 110.

The outer jacket 140 can be constructed from an elastomeric material such as a soft polymer material having good elasticity, while also being abrasion and tear resistance. Generally, the outer jacket 140 has a relatively low tensile modules compared to the inner and outer layers 108, 110. Example materials for the outer jacket 140 include, for example, a thermoplastic polyurethane such as Neusoft and Tecoflex™ 80 A B20. In some examples, the outer jacket 140 comprises an elastomer (e.g., an elastic polymer) with shore hardness (durometer) in the ranging between about 10 and about 95 Shore A. The outer jacket 140 can comprise an elastomer with an elongation at break of ranging between about 40% and about 800% (including about 40%, about 50%, about 60%, about 70%, about 80%, about 90%, about 100%, about 150%, about 200%, about 250%, about 300%, about 350%, about 400%, about 450%, about 500%, about 550%, about 600%, about 650%, about 700%, about 800%). The outer jacket 140 can comprises an elastomer with a wall thickness ranging between about 0.003 inches and about 0.015 inches (including about 0.003 inches, about 0.004 inches, about 0.005 inches, about 0.006 inches, about 0.007 inches, about 0.008 inches, about 0.009 inches, about 0.010 inches, about 0.011 inches, about 0.012 inches, about 0.013 inches, about 0.014 inches, about 0.015 inches). The wall thickness is measured radially between the inner surface of the outer jacket 140 and the outer surface of the outer jacket 140.

In some examples, the outer jacket 140 comprises a single material or combination of materials having a constant thickness along the entire length of the outer jacket 140. In alternative examples, the material composition and/or wall thickness can change along the length of the outer jacket 140. For example, the outer jacket 140 can be provided with one or more segments, where the composition and/or thickness changes from segment to segment. In an example, the Durometer rating of the composition changes along the length of the outer jacket 140 such that segments near the proximal end comprise a stiffer material or combination of materials, while segments near the distal end comprise a softer material or combination of materials. Similarly, the wall thickness of the outer jacket 140 the wall thickness of the outer jacket 140 in segments near the proximal end can be thicker/greater than the wall thickness of the outer jacket 140 near the distal end.

Figure 61:
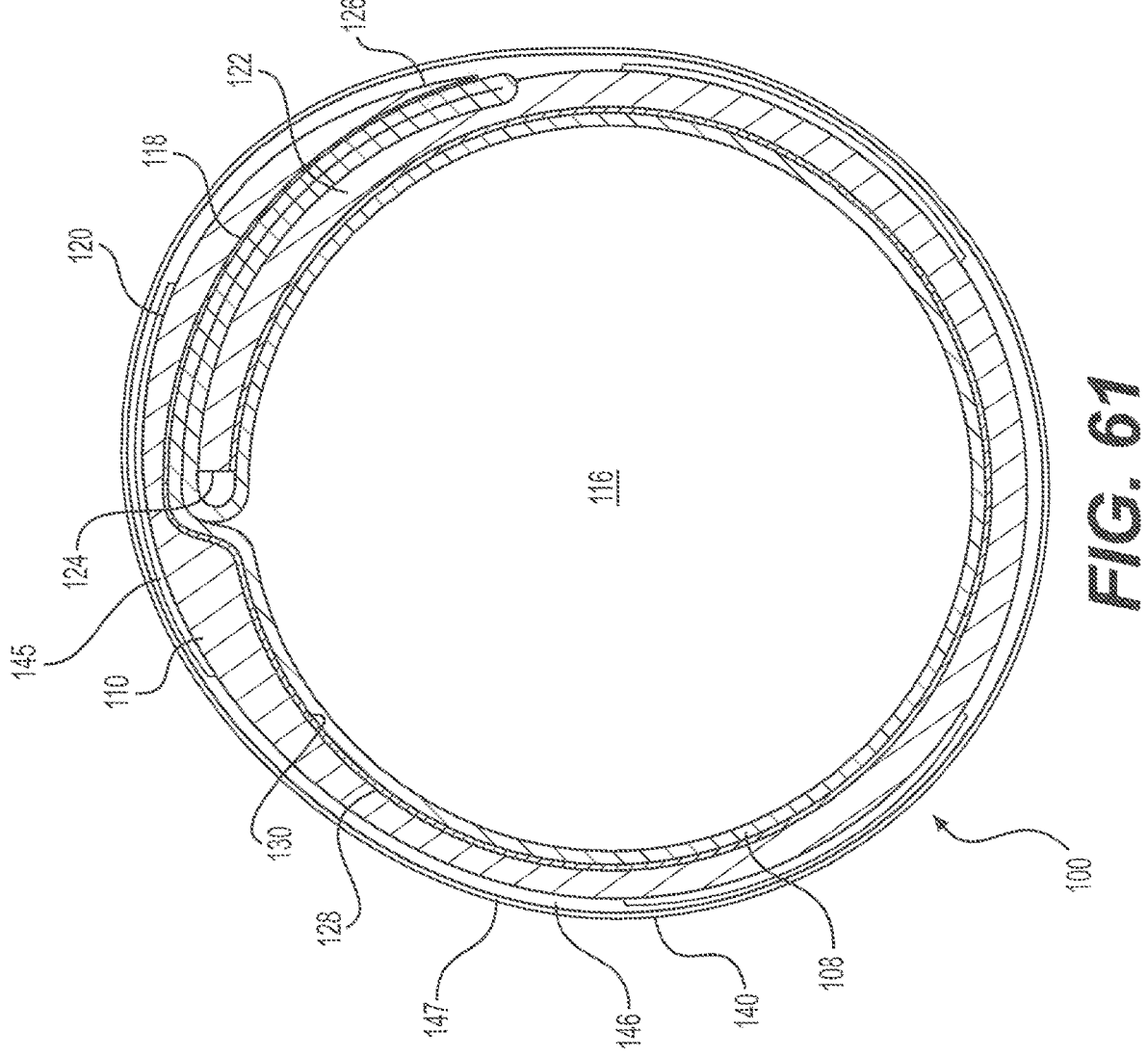
FIG. 61 is a section view of the sheath of FIG. 63 in a rest (unexpanded) configuration, taken along line 39-39 in FIG. 35.

As illustrated in FIG. 61, and described in more detail below with respect to FIGS. 62-65, the outer jacket 140 include one or more axial reinforcing members 145 that extend longitudinally along all or a portion of the outer jacket 140. The reinforcing member 145 provide stiffness and prevent axial bunching of the outer jacket 140 during insertion into the patient's vasculature while not sacrificing the low radial expansion force of the outer jacket 140.

As illustrated in FIG. 35, the sheath 100 can include a tapered segment adjacent the flared end portion 114 at the proximal end of the sheath 100. Referred to as a strain relief section, the tapered segment and the flared end portion 114 help ease the transition between the smaller diameter portion of the sheath 100 and the housing 101. The thickness and/or composition of the outer jacket 140 can be adjusted to increase the Durometer and/or stiffness along the strain relief section. Because this portion of the sheath 100 is usually outside of the patient's body during procedure, providing the outer jacket 140 with an increased Durometer and/or stiffness along the strain relief section helps to withstand the blood pressure that would otherwise cause the outer jacket 140 to "balloon up" with body fluid/blood. As a result, it allows for a sheath 100 having a relatively stiff proximal end at the point of introducing a delivery apparatus, while still having a relatively soft distal tip at the point of entry into the patient's vessel.

The outer jacket 140 can be bonded to the outer layer 110 to prevent the outer jacket 140 from sliding over the outer layer 110 and "bunching up" in response to the friction forces applied by the surrounding tissue during insertion of the sheath 100 into the patient's vasculature. For example, the outer jacket 140 can be bonded at the proximal end and/or distal end of the outer layer 110. At the proximal and distal ends, the outer jacket 140 can be bonded to the outer layer 110 around the full circumference of the outer layer. At the distal end of the sheath 100, the outer jacket 140 can alternatively be bonded to the inner layer 108. For example, the outer jacket 140 can be bonded to the distal end surface of the inner layer 108.

Figure 57:
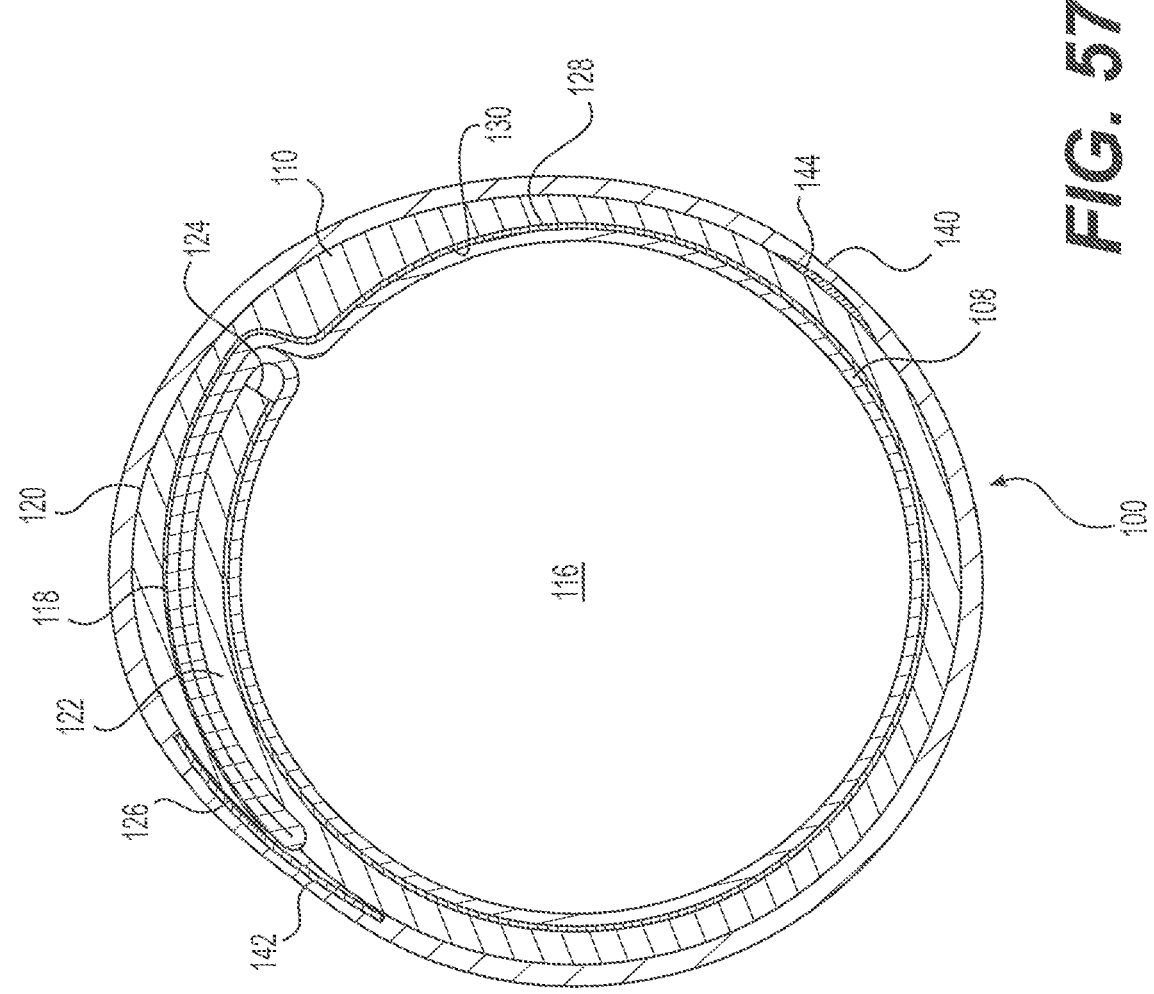
FIG. 57 is a section view of the sheath of FIG. 54 in a rest (unexpanded) configuration including a lubricant and a bonding strip.
Figures 58, 59:
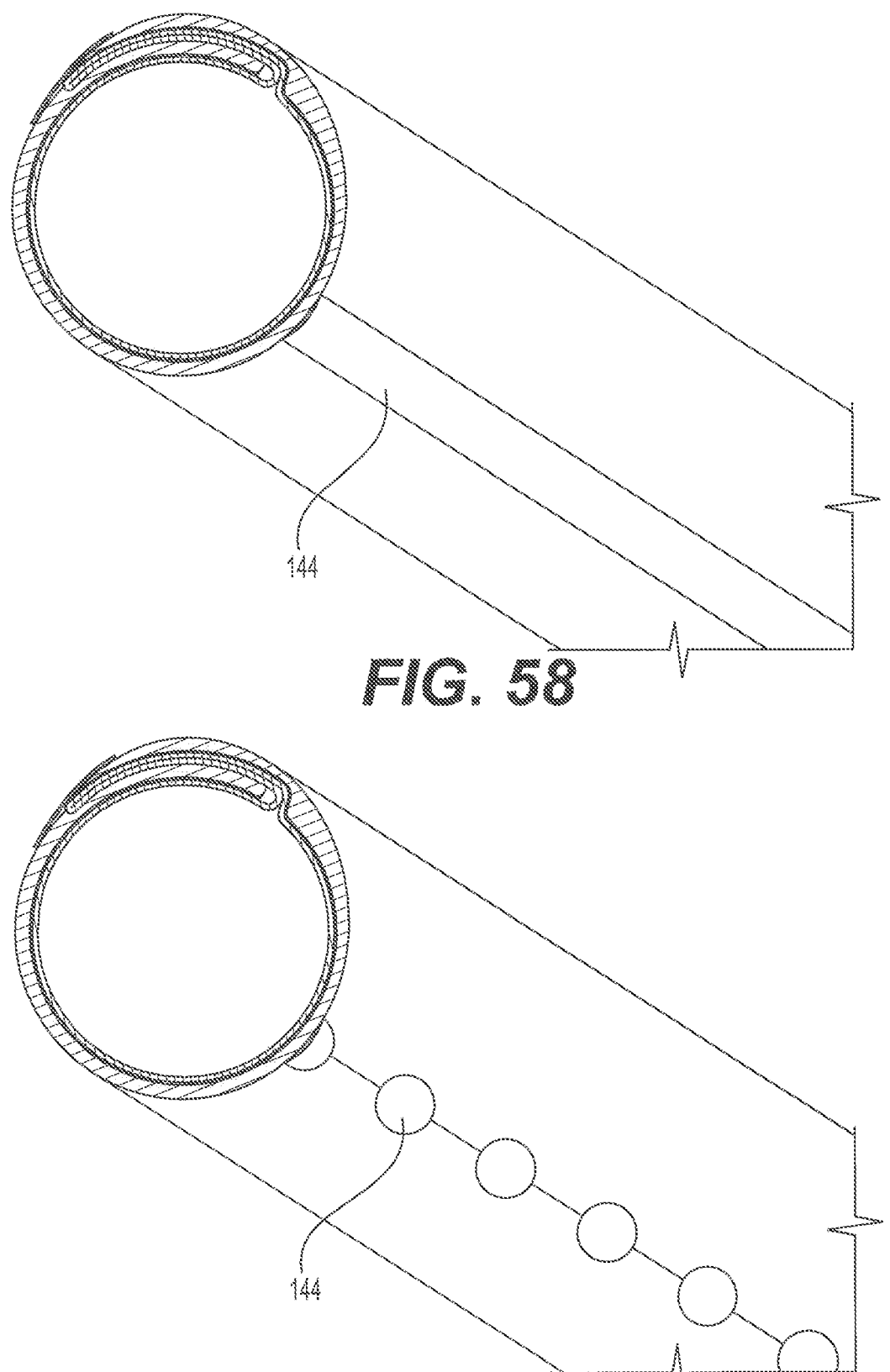
FIG. 58 is a bottom perspective view of the sheath of FIG. 57.
FIG. 59 is a bottom perspective view of the sheath of FIG. 57.

As illustrated in FIG. 57, the outer jacket 140 can be bonded 144 to the outer layer 110 at a circumferential location opposite the folded portion 118 of the inner layer 108. As provided in FIGS. 58-59, the bond 144 can be spot bonds or linear bond lines extending along all or a portion of the outer layer 110. As provided in FIG. 57, the bond 144 line/spot will also have a width, extending circumferentially around the outer layer 110. For example, the bond line can cover about 5° to about 90° of the circumference of the outer layer 110 (including about 5°, about 10°, about 15°, about 20°, about 25°, about 30°, about 35°, about 40°, about 45°, about 50°, about 55°, about 60°, about 65°, about 70°, about 75°, about 80°, about 85°, about 90°).

The outer jacket 140 can be bonded to the outer layer 110 and/or inner layer 108 using any mechanical and/or chemical (e.g., adhesive) fastener known in the art. In an example sheath 100, the outer jacket 140 and the outer layer 110 and/or inner layer 108 may have similar melting temperatures. Accordingly, an example bonding method includes a thermally bonded coupling between the outer jacket 140 the outer layer 110 and/or inner layer 108. For example, the bond between the outer jacket 140 and the outer layer 110 can be achieved by laser welding and/or a heat compression (e.g. using a heat compression jaw), allowing the location of the bond line to be closely controlled.

As shown in FIG. 54, and described above with respect to FIG. 39, and adhesive layer 128 (e.g., a tie layer) is provided between the inner layer 108 and the outer layer 110 to at least partially adhere the inner layer 108 to the outer layer 110. That is, the adhesive layer 128 is selectively provided/located between the inner layer 108 and the outer layer 110 to bond the inner and outer layers 108, 110 at the selected locations of the adhesive layer 128.

As illustrated in FIG. 54 (and FIG. 39) the adhesive layer 128 is provided on the outer surface of the inner layer 108 and/or the inner surface 130 of the outer layer 110. For example, the adhesive layer 128 can be provided partially or entirely around the outer surface of the inner layer 108. Additionally, or alternatively, the adhesive layer 128 can be provided partially and/or entirely around the inner surface 130 of the outer layer 110. As illustrated in FIG. 54, the adhesive layer 128 extends between the outer layer 110 and the overlapping folded portion 118 of the inner layer 108. That is, the adhesive layer 128 extends between the outer surface of the folded portion 118 of the inner layer 108 and the corresponding inner surface of the overlapping portion 120 of the outer layer 110. As illustrated in FIG. 54, the adhesive layer 128 does not extend between an inner surface of the overlapping folded portion 118 of the inner layer 108 and a corresponding surface of the underlying portion 122 of the outer surface of the outer layer 110. Excluding the adhesive layer 128 on the portion of the sheath between the inner surface of the folded portion 118 and the underlying portion 122, facilitates expansion of the sheath and prevents undesirable bonding/sticking between the inner and outer layers 108, 110 at this location.

The adhesive layer 128 can comprise a material having a Shore A hardness (durometer) less than about 90 A. For example, the adhesive layer 128 can comprise a thermoplastic polyurethane such as an aliphatic polyether-based thermoplastic polyurethane (TPU). An example TPU includes Tecoflex™ 80 A. The adhesive layer 128 can also be composed of an aromatic polyether or polyesters based thermoplastic polyurethane such as, for example, Pellethane™ 80 A. The adhesive layer can also be composed of a polyolefin or polyamide including, for example, a polyolefin (PE, PP, or EVA) modified with maleic anhydride such as an Orevac™ resin.

The thickness (wall thickness) of the adhesive layer 128 can vary, but in some examples the wall thickness of the adhesive layer ranges between about 0.002 inches and about 0.005 inches (including about 0.002 inches, about 0.003 inches, about 0.004 inches, about 0.005 inches). In other examples the wall thickness of the adhesive layer 128 ranges between about 0.0025 and about 0.0040 (including about 0.0025 inches, about 0.0030 inches, about 0.0035 inches, about 0.0040 inches). In a further example, the wall thickness of the adhesive layer 128 ranges between about 0.0025 inches and about 0.0035 inches (including about 0.0025 inches, about 0.0030 inches, about 0.0035 inches).

In some examples, the sheath 100 can include a lubricant to reduce friction and facilitate expansion/contraction between the outer layer 110 and the outer jacket 140. The lubricant 142 allows the outer layer 110 and inner layer 108 to unroll easily under the outer jacket 140, ensuring that the hemostasis and atraumatic benefits achieved by the addition of an outer jacket 140 does not comprise the push force performance of the sheath 100. That is, the lubricant 142 reduced the push force necessary to move the prosthetic device through the central lumen 116 of the inner layer 108 during delivery of the prosthetic device and the corresponding local expansion of the sheath 100.

Figure 56:
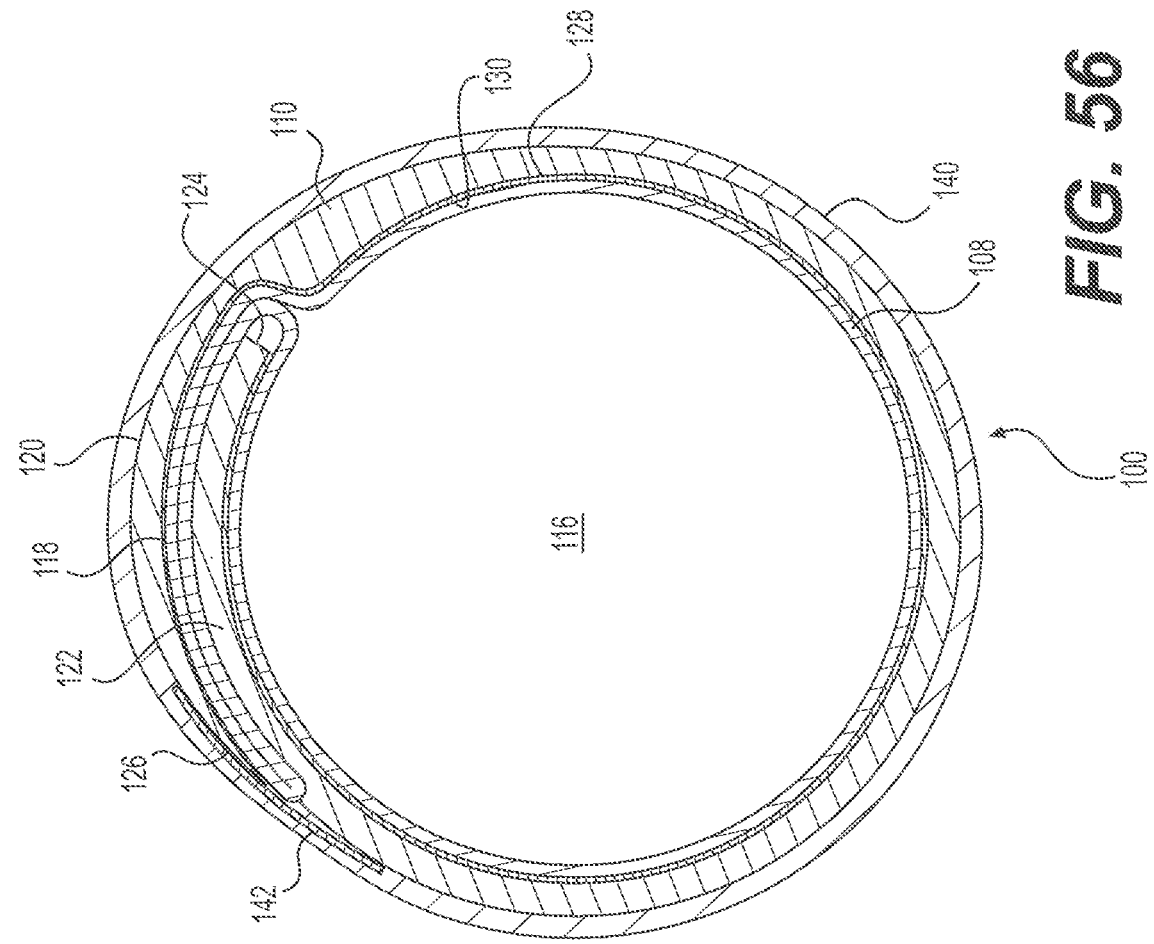
FIG. 56 is a section view of the sheath of FIG. 54 in a rest (unexpanded) configuration including a lubricant between the outer layer and the outer jacket.

As illustrated in FIG. 56, the lubricant 142 can be selectively applied along an outer surface of the outer layer 110 proximate the longitudinally extending edge 126 of the overlapping portion 120. In some examples, a portion of the folded portion 118 of the inner layer 108 extends beyond the longitudinally extending edge 126 of the overlapping portion 120 and along an outer surface of the outer layer 110. In this example, the lubricant 142 is also provided along the protruding portion the folded portion 118 of the inner layer 108 extending along the outer surface of the outer layer 110 (beyond the edge 126). In this location, the lubricant 142 also reduces friction between the outer jacket 140 and the inner layer 108 during expansion of the sheath 100. As illustrated in FIG. 56, the lubricant 142 extends around the circumference of the outer layer 110 beyond the protruding portion the folded portion 118.

The lubricant is applied as a band (or spot) that extends both circumferentially and longitudinally along the outer layer 110 (and protruding portion of the inner layer 108). In an example sheath 100, the lubricant 142 is applied as a band that extend both circumferentially around the outer layer 110 and longitudinally along a length of the outer layer 110. To prevent migration, the lubricant 142 can be composed of a heat curable material, e.g., a material curable at room temperature. As a result, the material can be applied to a desired location along the outer layer 110 and does not migrate during assembly and/or use of the sheath 100. The lubricant 142 can be composed of a medical grade lubricant, such as silicone. Example lubricants include medical grade curable silicone lubricants including a platinum catalyzed thermal curing silicone lubricant such as NuSil™ MED10-6670 (heat curable), a PTFE lubricant such as Duraglide™ (curable at room temperature) and/or CHRISTO-LUBE™.

Figure 60:
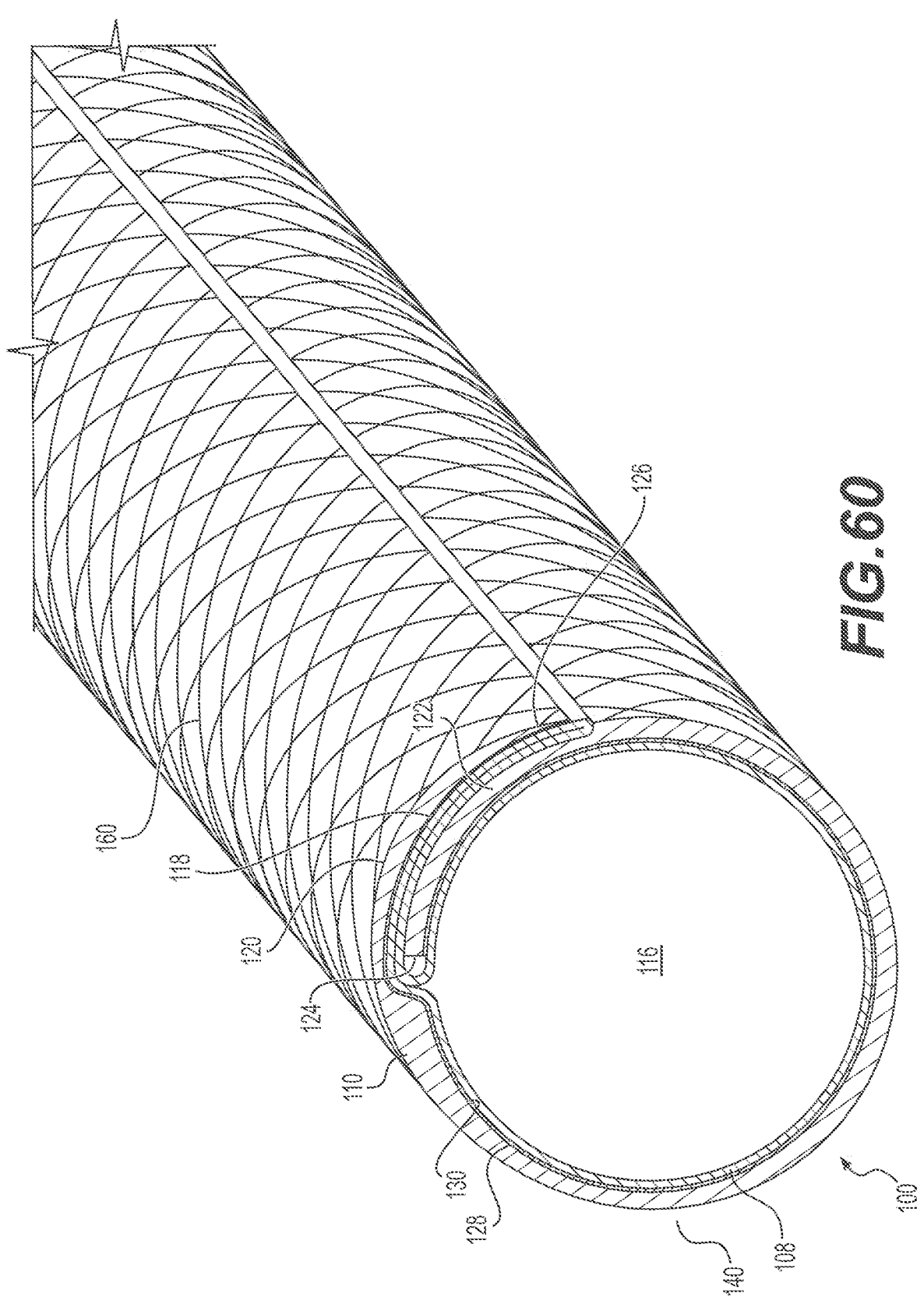
FIG. 60 is a top perspective view of the sheath of FIG. 54.

FIG. 60 illustrates an additional example of the sheath 100 of FIG. 35. In this example, the sheath 100 can include a coiled wire 160, or coiled wire mesh, along a length of the sheath 100. The coiled wire 160 provides uniform bending of the sheath and prevents kinking. The coiled wire 160 can be embedded in the outer layer 110. For example, the coiled wire 160 can be co-extruded with the outer layer 110. Alternatively, the coiled wire 160 can be provided between the outer layer and the adhesive layer 128. In another example, the coiled wire 160 is embedded, at least partially, within both the outer layer 110 and the adhesive layer 128.

For example, the coiled wire 160 can be provided on an outer surface of the adhesive layer 128 and the outer layer 110 is reflowed over.

As illustrated in FIG. 60, the coiled wire 160 defines a helical-shaped path around the longitudinal axis of the sheath 100. The example coiled wire 160, includes overlapping helical-shaped path around the longitudinal axis of the sheath 100, resulting in a continuous diamond-shaped pattern along the length of the sheath.

The coiled wire 160 can be comprised of a metal or a polymer wire. For example, the coiled wire 160 can be composed PET, PEEK, stainless steel, and/or nitinol. The coiled wire 160 can be comprised of a flat wire, a round wire, or a combination thereof. The individual wires of the coiled wire 160 can have a diameter/thickness ranging between about 0.002 inches and about 0.008 inches (including about 0.002 inches, about 0.003 inches, about 0.004 inches, about 0.005 inches, about 0.006 inches, about 0.007 inches, about 0.008 inches). In another example, the individual wires of the coiled wire 160 can have a diameter/thickness ranging between about 0.004 inches and about 0.007 inches. In a further example, the individual wires of the coiled wire 160 can have a diameter/thickness of about 0.006 inches. The pitch/distance between adjacent coils of the coiled wire 160 can correspond to the diameter/thickness of the coiled wire. For example, where the diameter/thickness a single coil of the coiled wire is about 0.006 inches, the spacing/pitch between the wire and the next adjacent coiled wire is about 0.006 inches.

Methods of using the sheath of FIGS. 53-60 include first inserting the expandable sheath 100 into the vasculature of a subject and advancing a prosthetic device through the inner lumen 116 of the inner layer 108/sheath 100. The prosthetic device applies an outwardly directing radial force on the inner layer 108 of the expandable sheath 100. In some examples, the outwardly directed radial force is transmitted through the inner layer 108, the adhesive layer 128 and the outer layer 110. The lumen 116 of the sheath 100 expands at the axial location of the prosthetic device due to the outwardly directed radial force exerted by a prosthetic device against an inner surface of the lumen during advancement. During expansion of the lumen 116 the first fold (folded edge) of the folded portion 118 is moved circumferentially closer to the second fold (folded edge), shortening the overlapping portion of the folded portion 118 that extends circumferentially between the first and second folds, thereby increasing the circumference of the lumen 116.

As the sheath 100 expands at a particular location (i.e., locally expands at the location of the passing prosthetic device), the overlapping portion 120 of the outer layer 110 can move circumferentially with respect to the underlying portion 122 as the folded portion 118 of the inner layer 108 least partially separate and/or unfold, causing the elongate gap(s) 132 provided in the outer layer 110 to widen/expand. The sheath thereby expands to accommodate a medical device having a diameter larger than that of lumen 116 in the resting (unexpanded) configuration. As shown in FIG. 55, in some examples, the folded portion of the inner layer 108 can completely unfold, so that the inner layer 108 forms a cylindrical tube at the location of the expanded configuration. As illustrated in FIGS. 54 and 55, the elongate gap 132 is generally aligned with the longitudinal axis of the lumen 116 such that during expansion, the unfolded portion of the inner layer 108 expands into the gap 132.

In an unexpanded configuration, the sheath 100 can have outer diameter less than about 0.030 inches (including less than about 0.029 inches, less than about 0.028 inches, less than about 0.027 inches, less than about 0.026 inches, less than about 0.025 inches, less than about 0.024 inches). Preferably, the unexpanded sheath has an outer diameter ranging between about 0.024 inches and about 0.026 inches. In a fully expanded configuration, the sheath 100 can have an inner diameter greater than 0.040 inches. Preferably, the expanded sheath 100 has an inner diameter ranging between 0.046 inches and 0.054 inches (including about 0.046 inches, about 0.047 inches, about 0.048 inches, about 0.049 inches, about 0.050 inches, about 0.051 inches, about 0.052 inches, about 0.053 inches, about 0.054 inches)

As described above, the inner and outer layers 108, 110 can be bonded together using an adhesive layer 128. The adhesive layer 128 prevents movement, both longitudinal and radial between the inner and outer layers 108, 110. As a result, expansion of the sheath 100 can be limited to only those regions excluding the adhesive layer 128. For example, as illustrated in FIG. 54, because the adhesive layer 128 is not provided between the inner surface of the folded portion 118 and the underlying portion 122 of the outer layer, expansion of the sheath results in the inner surface of the folded portion extending into the gap 132 created between the first and second edges 124, 126 of the expanded outer layer 110.

Once the prosthetic device as passed through the lumen 116 (or a particular location along the lumen), the lumen 116 of the sheath can at least partially contracts back to an unexpanded configuration. The outer layer 110 can exert an inwardly directed radial force on the inner layer 108 urging it back to its original folded configuration. Similarly, if a coiled wire 160 was included, the coiled wire can exert an inwardly directed radial force on the outer layer 110 and the inner layer 108 urging them back towards an unexpanded configuration. Likewise, if an outer jacket 140 is included, the outer jacket 140 can exert an inwardly directed radial force on the outer layer 110 and the inner layer 108 urging them back to an unexpanded configuration.

The prosthetic device can be delivered through the distal end of the sheath 100 to the delivery site within the patient. The prosthetic device can include a self-expanding heart valve or a stent-mounted heart valve. The heart valve can be extended through the distal end of the elongate lumen 116 at the delivery site. Once outside the lumen 116, the heart valve can be expanded and the sheath 100 removed from the treatment site.

An example method of making the sheath is as follows. These steps are not meant to be limiting. The steps given can be reordered as needed. Other steps can be added, or in other examples, some steps may not be necessary. A continuous inner layer 108 defining a lumen therethrough is provided. The inner layer 108 is formed to include first fold and a second fold and an overlapping folded portion 118 extending circumferentially between the first and second folds. The overlapping folded portion 118 is formed to include overlap in a radial direction of at least two thicknesses of the inner layer 108. The inner layer 108 can be extruded including the folded portion 118. Alternatively, the folded portion 118 can be formed after the inner layer 108 is extruded (e.g., formed on a cylindrical tubular structure).

A discontinuous outer layer 110 is provided (at least partially) around the inner layer 108. The outer layer 110 is formed to include an overlapping portion 120 and an underlying portion 122 such that at least a portion of the folded portion 118 of the inner layer 108 is positioned between the overlapping portion 122 and the underlying portion 120. In some examples, the inner layer 108 and the outer layer 110 are coextruded. In alternative examples, the inner layer 108 and the outer layer 110 are separately formed and joined together.

An adhesive layer 128 is provided between the inner layer 108 and the outer layer 110 for bonding (at least partially) the inner layer 108 to the outer layer 110. The adhesive layer 128 can applied to and bond the inner and outer layers 108, 110 axially along a length of the sheath, e.g., along a portion of the entire length of the sheath or along the entire length of the sheath. In an example, the adhesive layer 128 is coextruded with the outer layer 110. In a further example, the adhesive layer 128 is coextruded with the inner layer 108. In an alternate example method, the adhesive layer 128 can be applied to the outer surface of the inner layer 108 and/or an inner surface of the outer layer 110.

After the adhesive layer 128 is applied to the desired locations along the inner and/or outer layer 110, the outer layer 110 is applied over the inner layer 108. The outer layer 110 can then be bonded to the inner layer 108 by heat curing the adhesive layer 128. The adhesive layer 128 can comprise a material curable at a temperature above room temperature, in which case a heat treatment may be applied to the assembled inner layer 108/outer layer 110. The adhesive layer 128 may also be composed of a material that cures at room temperature. Accordingly, after application of the adhesive layer 128 and assembly of the outer layer 110 over the inner layer 108 (at a temperature below room temperature), the temperature of the combined layers may be increased to room temperature.

As illustrated in FIG. 56, the lubricant 142 can be selectively applied to a desired location along a length of outer layer 110 and/or outer jacket 140. As described above, the lubricant 142 can be provided on an outer surface of the outer layer 110 proximate a longitudinally extending edge 126 of the overlapping portion 120, on any portion of the folded portion 118 extending/protruding beyond edge 126, and/or on any portion of the outer surface of the outer layer 110 adjacent the protruding portion of the folded portion 118. The lubricant 142 can be applied as a band extending around a portion of the circumference of the outer layer, the band of lubricant 142 also extending longitudinally along a length of the outer layer 110. After the lubricant 142 is selectively applied to the outer surface of the outer layer 110, the outer jacket 140 can be applied over the outer layer 110. As outlined above, the lubricant 142 can comprise a heat curable material, in which case a heat treatment can be applied to the outer layer 110/outer jacket 140. The lubricant 142 may also be composed of a material that cures at room temperature. Accordingly, after application of the lubricant 142 (at a temperature below room temperature), the temperature of the outer layer 110 (separately or in combination with the outer jacket 140) can be increased to room temperature.

The outer jacket 140 can then be applied over/around the outer layer 110 and bonded to the outer layer 110 at at least one of the proximal and distal ends of the outer layer 110. The outer jacket 140 can also be bonded to the outer layer 110 along a length of the outer layer 110. The outer jacket 140 can be bonded to the outer layer 110 via a heat treatment process, e.g., a reflow process where the outer layer 110 and the outer jacket are headed to a temperature high enough such that the outer layer 110 and the outer jacket 140 are at least partially melted and are then fused together are the heat is removed and the assembly cools. The entire sheath 100 assembly may be reflowed to reduce the overall outer diameter and regain/ensure a circular shape in cross-section.

As described above, select portions of the outer surface of the inner layer 108 can include a surface treatment such as surface etching. In an example method, surface treatment of the inner layer 108 would occur before application of the outer layer 110. It is contemplated that it may be desirable to exclude etching from those surfaces of the inner layer 108 that come into contact with the outer surface of the outer layer 110. For example, etching may not be included between the inner surface of the folded portion 118 of the inner layer 108 and the underlying portion 122 of the outer layer 110. By excluding etching on the portions where the inner layer 108 and the outer surface of the outer layer 110 are in direct contact helps to facilitate release of the inner surface of the folded portion 118 and the outer layer 110 during expansion of the sheath 100.

In some instances, it may be necessary to release ("break") any undesirable bonding that occurs between the outer layer 110 and the inner layer 108. This bonding can occur due to the etching on the outer surface of the inner layer 108 that allows it to stick directly to the outer layer 110 (with/without the adhesive layer 128). Undesirable bonding can also occur if the outer layer 110 can flows on top the folded inner layer 108 and "grabs" it during the reflow process.

However, when the inner layer 108 is unetched along those locations excluding the adhesive layer 128, e.g., those portions adjacent the underlying portion of the outer layer 110, undesirable bonding between the outer layer 110 and the inner layer 108 at this location is limited. Therefore, it may not be necessary to precondition the sheath to release undesirable bonding between the inner layer 108 and the outer layer 110 because the bonding has not occurred (or is less likely to occur).

Nonetheless, undesirable bonding between the inner layer 108 and the underlying portion 122 of the outer layer 110 can be released, while maintaining desirable bonding at the proximal and distal ends of the sheath 100. For example, a mandrel can be passed at least partially through the lumen 116 of the inner layer 108, expanding the inner layer 108 and the outer layer 110, and breaking/releasing any undesirable bonding between the inner layer 108 and the underlying portion 122 of the outer layer 110.

FIGS. 41-49 illustrate additional examples and variations on the general sheath 100 described above. It is to be understood that the variations (e.g., materials and alternate configurations) described above with reference to FIGS. 35-40 can also apply to the examples shown in FIGS. 41-49. Furthermore, the variations described below with reference to FIGS. 41-49 can also be applied to the sheath described in FIGS. 35-40.

Figures 41, 42, 43:
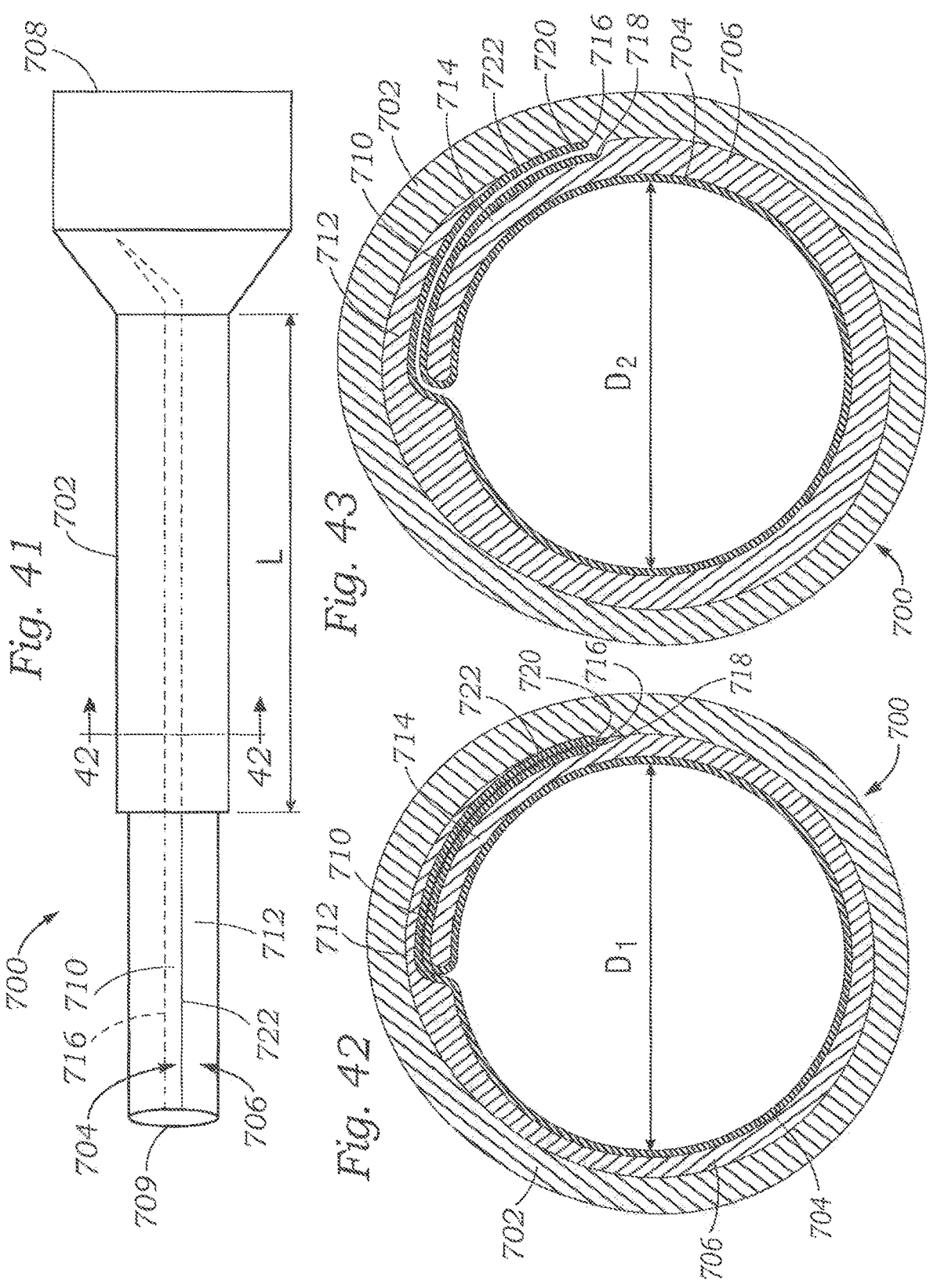
FIG. 41 shows an elevation view of an expandable sheath having an elastic outer cover, according to another example.
FIG. 42 illustrates a section view of the sheath of FIG. 41, taken along line 42-42 in FIG. 41.
FIG. 43 illustrates the section view of the sheath shown in FIG. 42, in an expanded configuration.

FIGS. 41-43 illustrate a sheath 700 that additionally includes a strain relief cover, also referred to as an elastic outer cover, or an elastic cover 702 positioned around at least a part of an inner layer 704 and outer layer 706. As shown in FIG. 41, the elastic cover 702 can extend for a length L along at least a portion of the main body of the sheath 700. In some examples, the elastic cover 702 can extend from the proximal end 708 of the sheath 700 and towards the distal end 709 of the sheath. In some examples, the elastic cover 702 extends only part way down the length of the sheath 700. In alternate examples, the elastic cover 702 can extend to a point adjacent the distal end 709, or can extend all the way to the distal end 709 of sheath 700. Furthermore, the outer elastic cover 702 need not extend all the way to the proximal end 708 of the sheath 700. In some examples, the outer elastic cover 702 may extend only part way towards the proximal end 708. In some examples, the longitudinal length L of the elastic cover 702 can range from about 10 cm to the entire length of the sheath 700.

As shown in FIGS. 42 and 43, the elastic cover 702 can be a continuous tubular layer, without slits or other discontinuities. The elastic cover 702 can be positioned to surround the entire circumference of outer layer 706, and can extend longitudinally along any portion of the length of the sheath 700. The outer elastic cover 702 can comprise any pliable, elastic material(s) that expand and contract, preferably with a high expansion ratio. Preferably, the materials used can include low durometer polymers with high elasticity, such as Pebax, polyurethane, silicone, and/or polyisoprene. Materials for the outer elastic cover 702 can be selected such that it does not impede expansion of the sheath 700. In fact, the outer elastic cover 702 can stretch and expand as the sheath 700 expands, such as by movement of the folded or scored inner liner with respect to itself.

The outer elastic cover 702 can, in some examples, provide hemostasis (e.g., prevent blood loss during implantation of the prosthetic device). For example, the outer elastic cover 702 can be sized or configured to form a seal with the patient's artery when inserted, such that blood is substantially prevented from flowing between the outer elastic cover 702 and the vessel wall. The outer elastic cover 702 can be inserted such that it passes the arteriotomy. For example, in examples where the outer elastic cover 702 does not extend all the way to the distal end 709 of the sheath 700, the elastic cover 702 can extend distally far enough such that when the sheath 700 is fully inserted into the patient, at least part of the elastic outer cover extends through the ateriotomoy site.

The elastic outer cover can have a thickness ranging from, for example, about 0.001" to about 0.010." In some examples, the outer cover can have a thickness of from about 0.003" to about 0.006." The elastic outer over can be configured to expand as the sheath expands, as shown in the expanded configuration in FIG. 43.

FIG. 42 shows a cross-section of the sheath 700 in a resting configuration having an inner diameter $D_1$. FIG. 43 shows a cross-section of the sheath 700 in an expanded configuration, having an inner diameter $D_2$, where $D_2$ is greater than $D_1$. Similar to the example of FIGS. 35-40, the sheath 700 can include an inner layer 704 having a folded portion 710, and an outer layer 706 having an overlapping portion 712 and an underlying portion 714. The overlapping portion 712 overlaps at least a portion of the folded portion 710 of the inner layer, and the underlying portion 714 underlies at least a portion of the folded portion 710. As shown in FIGS. 42-43, in some examples, the overlapping portion 712 does not overlap the entire folded portion 710 of the inner layer 704, and thus a portion of the folded portion 710 can be directly adjacent to the outer elastic cover 702 in locations where the elastic cover 702 is present. In locations where the elastic cover 702 is not present, part of the folded portion 710 may be visible from the outside of the sheath 700, as seen in FIG. 41. In these examples, the sheath 700 can include a longitudinal seam 722 where the overlapping portion 712 terminates at the folded portion 710. In use, the sheath can be positioned such that the seam 722 is posterior to the point of the sheath that is 180 degrees from the seam 722 (e.g., facing downward in the view of FIG. 41). The seam 722 can also be seen in FIG. 41, which shows that the seam 722 need not extend the entire length of the sheath. In some examples, the proximal end portion of the sheath includes two layers without a folded portion (e.g., similar to FIG. 38) while the distal end portion of the sheath includes two layers with a folded portion (e.g., similar to FIG. 39). In some examples, the seam 722 can end at a transition point between portions of the sheath having a folded inner layer and portions of the sheath not having a folded inner layer.

In some examples, the folded portion 710 can include a weakened portion, such as a longitudinal perforation, score line, and/or slit 716 along at least a portion of the length of the inner layer 704. The slit 716 can allow for two adjacent ends 718, 720 of the folded portion 710 to move relative to one another as the sheath 700 expands to the expanded configuration shown in FIG. 43. As a device having an outer diameter device larger than the initial resting inner diameter of the sheath 700 is inserted through the sheath 700, the device can cause local expansion of the sheath 700 and cause the sheath 700 to expand at the partial score or split line location (e.g., along slit 716). The weakened portion/slit 716 can extend longitudinally along any portion of the expandable sheath 700.

Figures 44, 45:
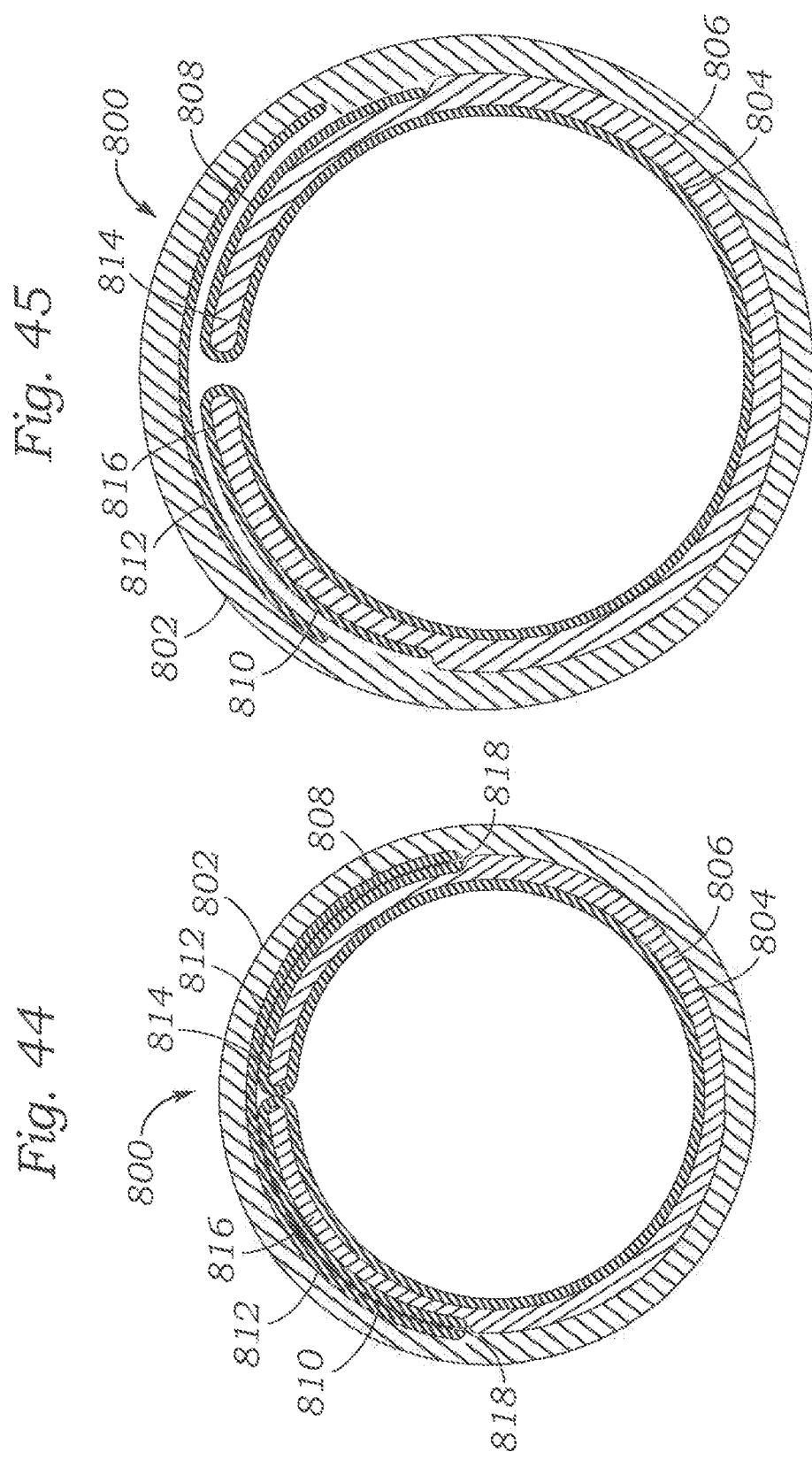
FIG. 44 illustrates a section view of another example of an expandable sheath.
FIG. 45 shows an expanded configuration of the sheath of FIG. 44.

FIGS. 44 and 45 show another example of an expandable sheath 800 having an initial diameter in a resting configuration (FIG. 44) and a larger expanded diameter in an expanded configuration (FIG. 45). The sheath 800 can include an elastic outer cover 802, an inner layer 804, and an outer layer 806. Inner layer 804 can include first and second folded portions 808, 810. The folded portions 808, 810 can be arranged such that they fold away from one another in opposite directions around the circumference of the sheath 800. For example, folded portion 808 can be folded to the right in the view of FIG. 44 and folded portion 810 can be folded to the left such that they do not overlap one another, but share a common segment 812 which is part of both folded portions 808, 810. In contrast to previous examples, the outer layer 806 does not include an overlapping portion in this example, but rather has first and second underlying portions 814, 816, which underlie the first and second folded portions 808, 810, respectively. The inner layer 804 can extend through a gap between the ends of the adjacent underlying portions 814, 816 (e.g., between a first end and a second end of discontinuous outer layer 806).

Each folded portion 808, 810 can include a weakened portion 818, such as a slit, score line, and/or perforation. Weakened portion 818 can allow the expandable sheath 800 to expand easily without a high radial force. As the sheath 800 expands, segment 812 along the top of the folded portions 808, 810 of inner layer 804 can be configured to split apart from the rest of the folded portions 808, 810 and the first and second underlying portions 814, 816 can move away from one another so as to create an enlarged lumen within the inner layer 804. Weakened portions 818 can allow for the segment 812 to easily split apart from the inner layer 804 as the sheath 800 expands.

FIGS. 46-47 show another example of an expandable sheath 900. Sheath 900 can be provided with an inner layer 902 and an elastic cover 904 surrounding the inner layer 902. While not shown, sheath 900 can additionally include an intermediate layer positioned between the inner layer 902 and the elastic cover 904. If present, the intermediate layer can closely follow the contour of the inner layer 902.

Inner layer 902 can be shaped to include one or more folded portions 906 arranged to form a generally horseshoe-shaped lumen 908 that extends longitudinally through sheath 900 along the inner surface of the inner layer 902. The folded portions 906 can be arranged to form an area 910 positioned with the lumen 908 and radially inward from the elastic cover 904. In some examples, the area 910 can include one or more voids (e.g., smaller lumens or openings extending through area 910). In some examples, the area 910 can be filled with material (e.g., HDPE) reflowed from an intermediate layer while the sheath is being made. In some examples, the area 910 can be filled with material reflowed from the elastic cover 904 during the sheath manufacturing process.

The inner layer 902 can include one or more weakened portions 912, such as score lines, perforations, or slits. The weakened portions 912 can be configured to split apart, separate, or widen as the sheath expands from its initial resting configuration (FIG. 46) to an expanded configuration (FIG. 47) in the presence of a radial force. As the sheath 900 expands, material from the area 910 can cover any gaps 914 formed at the weakened portions 912, thereby keeping the lumen 908 substantially sealed.

Figures 48, 49:
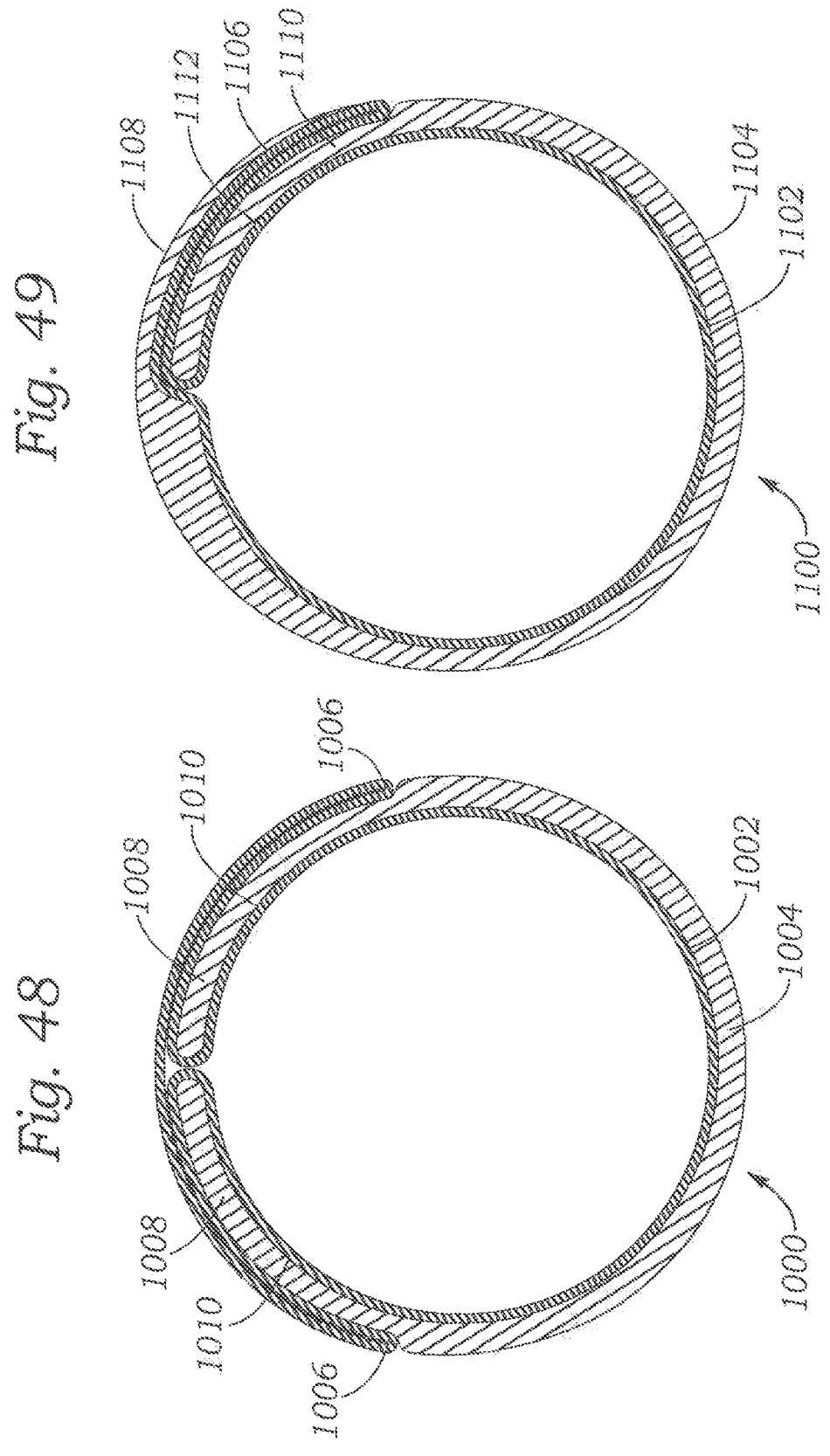
FIG. 48 illustrates a section view of another example of an expandable sheath according to the present disclosure.
FIG. 49 illustrates a section view of another example of an expandable sheath.

FIG. 48 shows another example of an expandable sheath 1000 having an inner layer 1002 and a discontinuous outer layer 1004. Sheath 1000 is similar to the sheath 800 of FIG. 44, except that sheath 1000 is shown without an elastic outer cover and further, the inner layer 1002 is continuous, without weakened portions at the folds 1006. As shown in FIG. 48, the inner layer 1002 can be configured to have one or more folds 1006 (e.g., two folds positioned on the outer surface of the outer layer 1004), with portions 1008 of the outer layer 1004 extending between the folds 1006 and the outer surface 1010 of the inner layer 1002 underlying the folds 1006.

FIG. 49 shows yet another example of an expandable sheath 1100 having an inner layer 1102 and an outer layer 1104. The sheath 1100 is similar to the sheath 100 shown in FIG. 39 in that the inner layer 1102 can be continuous with a folded portion 1106, and the outer layer 1104 can be discontinuous with an overlapping portion 1108 overlapping at least a part of the folded portion 1106 and an underlying portion 1110 underlying at least a part of the folded portion 1106. The underlying portion 1110 can thus be positioned between an outer surface 1112 of the lumen-forming portion of the inner layer 1102 and the folded portion 1106.

The inner layers 1002, 1102 of the sheaths 1000, 1100, respectively, of FIGS. 48-49 can be optimized to perform slightly differently than the inner layers of sheaths described above. For example, different materials can be used for the inner liner to increase durability and softness of the seam (although such materials can also be used with the other examples of expandable sheaths described above). For example, materials such as woven fabrics or braid filaments can be used. Such fabrics, filaments, or yarns can comprise, for example, PTFE, PET, PEEK, and/or nylon yarns or filaments. These materials can advantageously provide a soft and flexible layer that can be easily formed into the desired shapes or folded portions. Additionally, such materials can withstand high temperatures, as well as can possess high tensile strength and tear resistance. Nonetheless, these materials can also be elastic, experience minimal kinking, and provide soft distal edges for less traumatic insertion into a patient's vessels.

In further aspects, the outer jacket disclosed herein can comprise at least two polymer layers. In still further aspects, the outer jacket disclosed herein can comprise at least one intermediate reinforcement layer/member disposed between the first polymer layer and the second polymer layer of the outer jacket. In still further aspects, the at least one intermediate reinforcement layer/member is a polymer layer. FIGS. 62-65 illustrate an expandable outer jacket including longitudinally extending reinforcing members 145. The outer jacket 140 can be used with any of the expandable sheaths described herein. The reinforcing members 145 prevent axial bunching of the outer jacket 140 during insertion into the patient's vasculature while not sacrificing the low radial expansion force of the outer jacket 140. The reinforcing members 145 are typically constructed from a stiffer material (e.g., Pebax, polyurethane, nylon, flat wire) than the main body portion of the outer jacket 140. The resistance of the reinforcing members 145 to elongation and/or compression prevents bunching/crumpling of the outer jacket 140 during insertion, while still allowing the outer jacket 140 to radially expand.

Figures 62, 63:
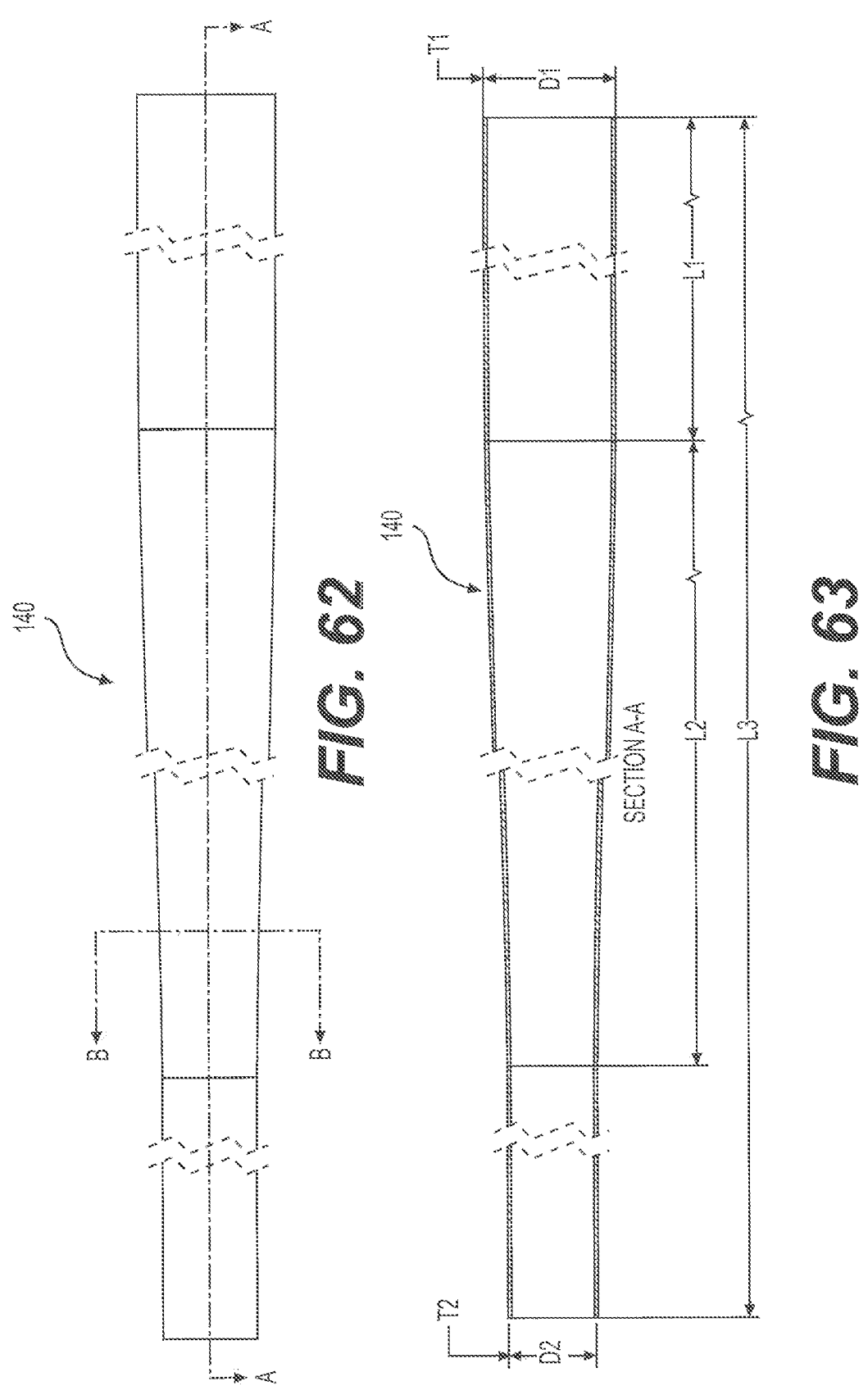
FIG. 62 is an elevation view of an expandable outer jacket according to another example.
FIG. 63 is a cross-section view of the expandable sheath of FIG. 64 taken along section line A-A of FIG. 62.

FIG. 62 is an elevation view of the outer jacket 140 showing a tapered segment adjacent the flared end portion at the proximal end of the sheath. FIG. 63 is a cross section view of the outer jacket 140 take along section A-A in FIG. 62. As described above, the tapered portion is referred to as a strain relief section and the tapered segment and the flared proximal end help ease the transition between the smaller diameter portion of the sheath 100 and the housing 101. The length of the proximal end (L1) can range from 1.600 inches to 2.400 inches. In some examples, the length of the proximal end is about 2.000 inches. The length of the tapered segment (L2) can range from 2.000 inches to 3.000 inches. In some examples, the length of the tapered segment (L2) is about 2.500 inches. The overall length of the outer jacket 140/sheath 100 (L3) can range from 17.600 inches to 26.400 inches. In some examples, the overall length of the of the outer 140/sheath 100 (L3) is about 22.000 inches.

As provided in FIG. 62, the diameter of the outer jacket 140 at the proximal end is greater than the diameter of the outer jacket 140 at the distal end. This allows the outer jacket 140 to be slid over the inner and outer layers 108, 110 without having to be expanded. For example, the diameter of the outer jacket 140 at the proximal end can range from 0.264 inches to 0.396 inches. In some examples, the diameter of the outer jacket 140 at the proximal end is about 0.330 inches. The diameter of the outer jacket 140 at the distal end can range from 0.176 inches to 0.264 inches. In some examples, the diameter of the outer jacket at the distal end is about 0.220 inches.

The wall thickness of the outer jacket 140 can range from 0.0040 inches to 0.0066 inches. In some examples, the thickness of the outer jacket 140 is about 0.0055 inches. The wall thickness of the outer jacket 140 can remain constant along the entire length of the outer jacket 140. However, in some examples, the thickness of the outer jacket 140 at the proximal end (T1) is greater than the thickness of the outer jacket 140 at the distal end (T2).

Figure 64:
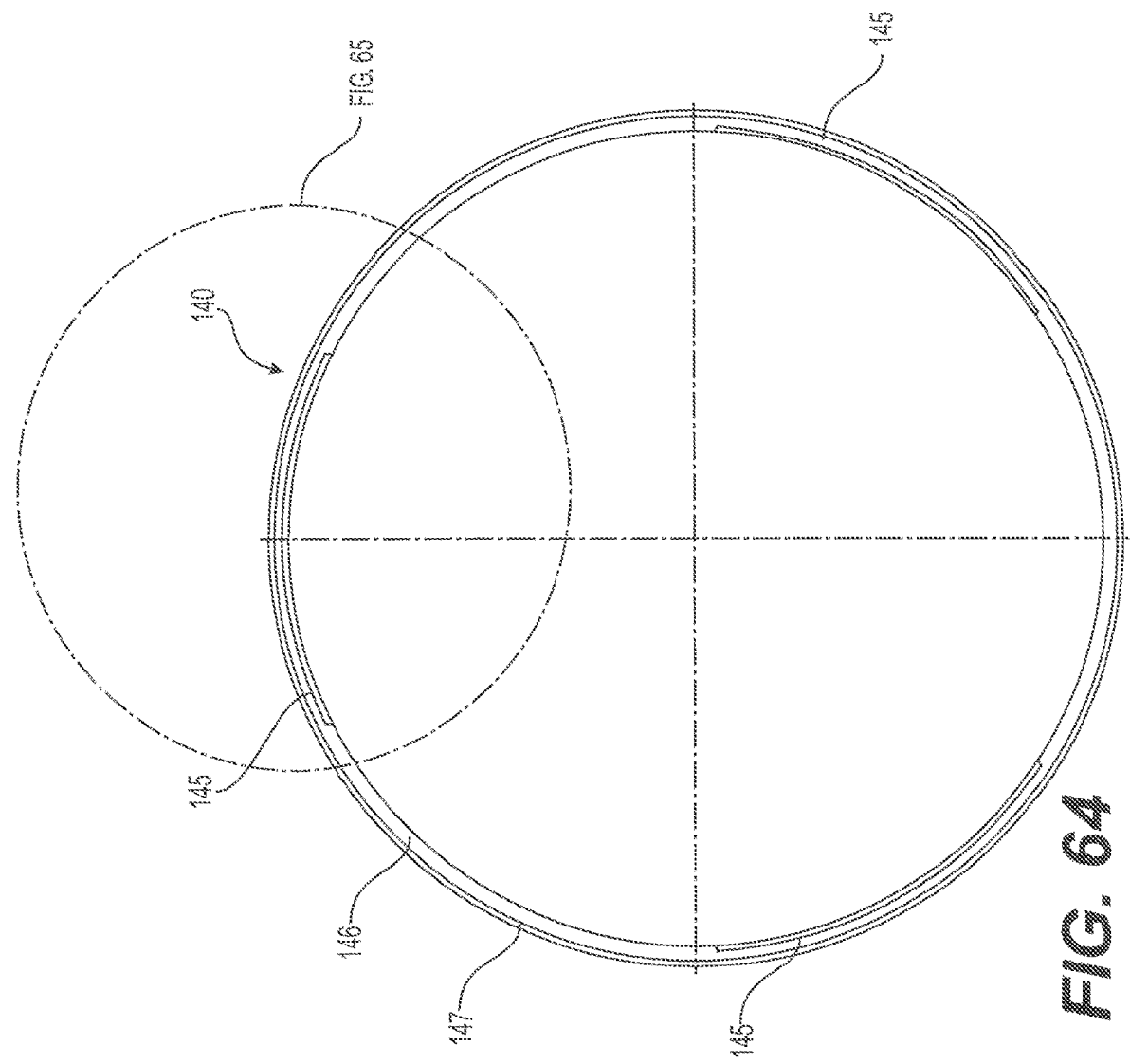
FIG. 64 is a section view of an expandable outer jacket in a rest (unexpanded) configuration, take along section lines B-B of FIG. 62.
Figure 66:
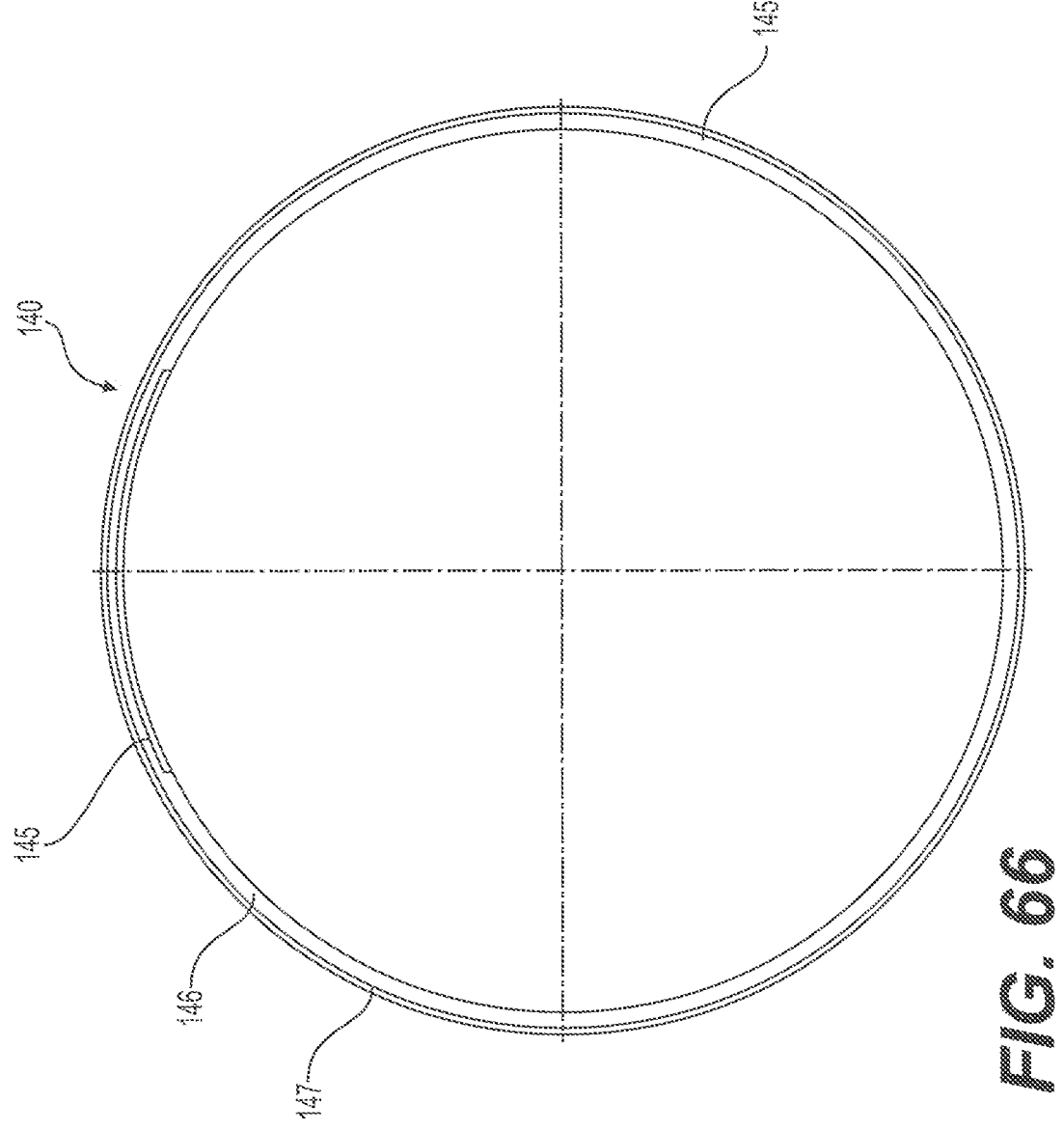
FIG. 66 is a section view of another example outer jacket in a rest (unexpanded) configuration including a single reinforcing member, taken along section lines B-B of FIG. 62.

In still further aspects, the outer jacket 140 can comprise two or more reinforcing members 145. In such aspects, the two or more reinforcing members 145 can be disposed, as individual strips, circumferentially between the inner and outer polymer layers at a predetermined distance from each other. FIG. 64 is a cross section view of the outer jacket 140 taken along section lines B-B in FIG. 62. As provided in FIG. 64, the outer jacket 140 includes three reinforcing members 145. In some examples, the outer jacket 140 includes only one reinforcing member 145 (FIG. 66). In other examples, the outer jacket includes up to eight reinforcing members 145. When more than one reinforcing member 145 is used, the reinforcing members are spaced evenly around the circumference of the outer jacket 140. As further illustrated in FIG. 64, the reinforcing member 145 can have a rectilinear shape (e.g., rectangular) in cross section. However, any other regular or irregular shape is contemplated.

In further aspects, the reinforcing member 145 has a finite width that is smaller than the circumference of the outer jacket 140. The total combined width (w) of the reinforcing members 145 can range from 10% to 50% of the circum-ference of the outer jacket 140. In still further aspects, the total combined width of the strips is about 10%, about 15%, about 20%, about 25%, about 30%, about 35%, about 40%, about 45%, or about 50% of the circumference of the elongated tube.

FIG. 65 includes a partial view of the outer jacket 140 of FIG. 64. As provided in FIG. 65, the circumferential width of the reinforcing members 145 can range from 0.025 inches to 0.100 inches. In some examples, the distal end of the outer jacket 140 has a diameter of 0.200 inches and the circum-ferential width of the reinforcing members 145 can range from 0.025 inches to 0.100 inches. In some exemplary and unlimiting aspects, the diameter of the outer jacket at the distal end is about 0.200", the reinforcing member(s) has a width between about 0.025" to about 0.100", including exemplary values of about 0.03", about 0.035", about 0.04", about 0.045", about 0.05", about 0.055", about 0.06", about 0.065", about 0.07", about 0.075", about 0.08", about 0.085", about 0.09", and about 0.095", about 0.10", about 0.105", about 0.110", about 0.115", about 0.120", about 0.125", about 0.130", about 0.135", about 0.140", and about 0.145". It is understood that the widths shown above are exemplary and if the distal outer diameter of the outer jacket has a size different from 0.200", the reinforcing member width can be adjusted in the same or a different ratio.

In still further aspects, the reinforcing member has a finite width that is smaller than the circumference of the elongated tube. In such aspects, the at least one reinforcing member 145 can be inserted as a strip between the first and the second polymer layers of the outer jacket 140. In some exemplary and unlimiting aspects, if the outer jacket has a distal outer diameter of about 0.200", the strip of the reinforcing member 145 can have a width between about 5% to about 50% of the circumference of the outer jacket. In still further aspects, the total combined width of the strips is about 5%, about 15%, about 20%, about 25%, about 30%, about 35%, about 40%, about 45%, or about 50% of the circumference of the outer jacket. It is understood that the widths shown above are exemplary and if the distal outer diameter of the elongated sheath has a size different from 0.200", the reinforcing member 145 width can be adjusted in the same or a different ratio.

In still further aspects, the outer jacket 140 can comprise two or more reinforcing members 145. In such aspects, the two or more reinforcing members 145 can be disposed, as individual strips, circumferentially spaced between the first and the second polymer layers at a predetermined distance from each other. In aspects, where the two or more rein-forcing member 145 are disposed between the first and the second polymer layers of the elongated tube, a total com-bined width of all the strips is about 5% to about 50% of the circumference of the outer jacket 140. In still further aspects, the total combined width of the reinforcing members 145 is about 5%, about 15%, about 20%, about 25%, about 30%, about 35%, about 40%, about 45%, or about 50% of the circumference of the outer jacket.

It is further understood that in the aspects, where the reinforcing member 145 is present as one or more strips disposed circumferentially along the length of the outer jacket 140, the width of the reinforcing member 145 can be the same along the length or it can vary along the length. In aspects, where the reinforcing member 145 width varies along the length of the outer jacket 140, such a reinforcing member 145 can have any of the disclosed above width values.

In still further aspects, at least one reinforcing member 145 is configured to provide an axial reinforcement to the outer jacket 140 and as a result to the sheath where the outer jacket 140 can be used. In such exemplary aspects, the at least one reinforcing member 145 can be disposed along the length of the outer jacket 140 or along a portion of the length of the outer jacket 140. In some aspects, the portion of the length of the outer jacket 140 where the at least reinforcing member 145 is disposed is positioned at the distal end and/or proximal end of the outer jacket 140. In yet other aspects, the reinforcing member 145 can also be positioned anywhere along the length of the outer jacket 140.

As described above, and as illustrated in FIG. 64, the outer jacket 140 includes a two layer construction, inner layer 146 and outer layer 147, where the outer layer provides abrasion resistance (for example, between the sheath and a calcific lesion) and better resistance to hydrophilic coating process, and the inner layer is a more lubricious material (for example, to prevent sticking of the outer jacket against the outer layer of the sheath during expansion) the and provides higher pressure resistance or ballooning resistance and hemostasis. In some aspects, the inner layer 146 (first polymer layer) forms the inner surface of the outer jacket 140 and the outer layer 147 (second polymer layer) forms the outer surface of the outer jacket, the reinforcing members 145 are disposed between the outer surface of the inner layer 146 and the inner surface of the outer layer 147.

In some examples, the inner layer 146 is composed of Pebax or polyurethane having Shore 25D to 35D. In some examples, the inner layer 146 includes a PTFE powder, an optional inorganic filler, and an optional tackiness reducing additive, to lower friction when outer layer 108 of the sheath expanding by sliding against the outer jacket 140. In some examples, the outer layer 147 of the outer jacket 140 is composed of polyurethane or polyurethane/Styrene Block Copolymer (SBC) having Shore A durometer lower than about 60, e.g., Neusoft 597-50 A having Shore A hardness of about 55 A. In certain examples, the inner layer 146 is constructed from Polyether Block Amide such as Pebax having Shore D durometer less than about 35.

In still further exemplary and unlimiting aspects, the inner layer 146 forms the inner surface of the outer jacket and comprises a first compound composition comprising from greater than 0 wt % to less than 100 wt % of a polymer comprising a polyether block amide, a polyurethane, or a combination thereof based on a total weight of the first compound composition; less than about 65% of an inorganic filler based on a total weight of the first compound composition; and up to about 20% of a solid lubricant filler based on a total weight of the first compound composition.

Any of the disclosed above inorganic fillers and solid lubricant fillers can be present in any amount as disclosed. For example, the inorganic filler can comprise bismuth oxychloride, barium sulfate, bismuth subcarbonate, calcium carbonate, aluminum trihydrate, barite, kaolin clay, limestone, or any combination thereof. In yet other aspects, the inorganic filler can be present in at least 10 wt %. In still further aspects, the inorganic filler can be present in an amount of less than about 50 wt % based on a total weight of the first compound composition.

In yet further aspects, the solid lubricant filler can comprise a PTFE filler.

The first compound can also comprise any of the disclosed above additives. For example, the compound can comprise at least one tackiness reducing compound in an amount from about 1 wt % to about 20 wt %.

In still further exemplary aspects, the polymer present in the first compound can have Shore D from about 20D to about 35D, including exemplary values of about 22D, about 25D, about 27D, about 30D, and about 32D.

In yet further aspects, a durometer of the polymer in the inner layer 146 (first polymer layer) composition at a proximal end of the outer jacket 140 can be different from a durometer of the polymer in the inner layer 146 (first polymer layer) composition at a distal end of the outer jacket 140.

In still further aspects, the polymer in the first compound can comprise PEBAX®. While in other aspects, the polymer in first compound can comprise polyurethane. In still further aspects, the first compound can also comprise polyamide.

In still further aspects, the outer layer 147 (second polymer layer) can comprise any of the disclosed above polymers. In some aspects, the outer layer 147 can comprise a second compound composition comprising from greater than 0 wt % to 100 wt % of a second polymer comprising polyether block amide, a polyurethane, or a composition thereof. In still further aspects, the outer layer 147 layer can comprise a polyamide. In yet in some other aspects, the second compound can also comprise any of the fillers or additives disclosed above. While in some aspects, the second compound does not comprise the solid lubricant fillers disclosed herein. While in still further aspects, the second compound can comprise a tackiness reducing additive described in this disclosure. In some aspects, the second polymer can be a polyurethane. In still further aspects, the polyurethane is a thermoplastic polyurethane. While in still further aspects, the second polymer can be a blend comprising a polyurethane with a styrene block copolymer. In still further aspects, the blend can further comprise additional polymers and copolymers. For example, ether-based polymers can be present in the blend. In some exemplary and unlimiting aspects, the second polymer can be chosen from commercially available polymers sold under trade name of Neusoft™. In still further aspects, the second polymer can have a Shore A durometer from about 20 A to about 75 A, including exemplary values of about 25 A, about 30 A, about 35 A, about 40 A, about 45 A, about 50 A, about 55 A, about 60 A, about 65 A, and about 70 A. In yet further aspects, the second polymer can have a Shore A durometer of less than 60 A. In some exemplary aspects, the second polymer can be Neusoft™ 597-50 A.

As provided in FIG. 65, the inner layer 146 is thicker than the outer layer 147. In general, the inner layer has a thickness ranging from 0.0010 inches to 0.0025 inches. In some examples, the inner layer has a thickness of about 0.00154 inches. The outer layer has a thickness ranging from 0.002 inches to 0.004 inches. In some examples, the outer layer has a thickness of about 0.003 inches.

In still further aspects, the thickness of the inner layer 146 (first polymer layer) can be from about 1 mil to about 5 mils, including exemplary values of about 1.1 mils, about 1.2 mils, about 1.3 mils, about 1.4 mils, about 1.5 mils, about 1.6 mils, about 1.7 mils, about 1.8 mils, about 1.9 mils, about 2.0 mils, 2.1 mils, about 2.2 mils, about 2.3 mils, about 2.4 mils, about 2.5 mils, about 2.6 mils, about 2.7 mils, about 2.8 mils, about 2.9 mils, about 3.0 mils, about 3.1 mils, about 3.2 mils, about 3.3 mils, about 3.4 mils, about 3.5 mils, about 3.6 mils, about 3.7 mils, about 3.8 mils, about 3.9 mils, about 4.1 mils, about 4.2 mils, about 4.3 mils, about 4.4 mils, about 4.5 mils, about 4.6 mils, about 4.7 mils, about 4.8 mils, and about 4.9 mils.

In still further aspects, the thickness of the outer layer 147 (second polymer layer) can be from about 1 mil to about 6 mils, including exemplary values of about 1.1 mils, about 1.2 mils, about 1.3 mils, about 1.4 mils, about 1.5 mils, about 1.6 mils, about 1.7 mils, about 1.8 mils, about 1.9 mils, about 2.0 mils, 2.1 mils, about 2.2 mils, about 2.3 mils, about 2.4 mils, about 2.5 mils, about 2.6 mils, about 2.7 mils, about 2.8 mils, about 2.9 mils, about 3.0 mils, about 3.1 mils, about 3.2 mils, about 3.3 mils, about 3.4 mils, about 3.5 mils, about 3.6 mils, about 3.7 mils, about 3.8 mils, about 3.9 mils, about 4.1 mils, about 4.2 mils, about 4.3 mils, about 4.4 mils, about 4.5 mils, about 4.6 mils, about 4.7 mils, about 4.8 mils, about 4.9 mils, about 5.1 mils, about 5.2 mils, about 5.3 mils, about 5.4 mils, about 5.5 mils, about 5.6 mils, about 5.7 mils, about 5.8 mils, and about 5.9 mils.

In still further aspects, the thickness of the reinforcement member 145 can be any where between about 1 mil to about 6 mils, including exemplary values of about 1.1 mils, about 1.2 mils, about 1.3 mils, about 1.4 mils, about 1.5 mils, about 1.6 mils, about 1.7 mils, about 1.8 mils, about 1.9 mils, about 2.0 mils, 2.1 mils, about 2.2 mils, about 2.3 mils, about 2.4 mils, about 2.5 mils, about 2.6 mils, about 2.7 mils, about 2.8 mils, about 2.9 mils, about 3.0 mils, about 3.1 mils, about 3.2 mils, about 3.3 mils, about 3.4 mils, about 3.5 mils, about 3.6 mils, about 3.7 mils, about 3.8 mils, about 3.9 mils, about 4.1 mils, about 4.2 mils, about 4.3 mils, about 4.4 mils, about 4.5 mils, about 4.6 mils, about 4.7 mils, about 4.8 mils, about 4.9 mils, about 5.1 mils, about 5.2 mils, about 5.3 mils, about 5.4 mils, about 5.5 mils, about 5.6 mils, about 5.7 mils, about 5.8 mils, and about 5.9 mils.

As provided in FIGS. 64 and 65, the reinforcing members 145 are at least partially embedded in the inner layer 146. In some examples, the thickness of the reinforcing member 145 is less than the thickness of the inner layer 146. For example, as illustrated in FIG. 65, the reinforcing members 145 have a thickness ranging from 0.0005 inches to 0.0015 inches. In some examples, the reinforcing members 145 have a thickness of about 0.001 inches. In an example configuration, the reinforcing members 145 have a thickness of 0.001 inches and the inner layer has a thickness of 0.00154 inches. In another example, not shown, the reinforcing member 145 has a thickness corresponding to the thickness of the inner layer 146. In a further example, the reinforcing member 145 has a thickness greater than the thickness of the inner layer 146. In some examples, the inner layer 146 and the reinforcing member 145 are co-extruded. Similarly, the inner layer 146, reinforcing member 145 and the outer layer 147 are co-extruded with the reinforcing member 145 positioned between the inner and outer layers 146, 147. In other examples, the inner layer 146 is provided over the reinforcing member 145 and the two components are bonded or fused together by at least one of heat or compression.

As described above, the reinforcing members 145 are constructed from a stiffer material than main body portion of the outer jacket 140 (inner layer 146, outer layer 147) and also a material having a low coefficient of friction (e.g., high density polyethylene). In some examples, the reinforcing members 145 are constructed from a polymer compatible to inner layer and outer layer including, for example, high durometer Pebax or polyurethane. The reinforcing member 145 can also be constructed from a material having a Shore D durometer ranging from 45D to 76D.

In some examples, the reinforcing members are constructed from a material excluding PTFE powder or inorganic filler, thereby providing axial compressive/tensile stiffness (from higher durometer material) and friction against axial bunching (without PTFE powder).

In certain examples, the outer layer 147 is constructed from NEUSOFT 597-50, the inner layer 146 is constructed from Pebax 25D including PTFE and BaSO4, and the reinforcing member 145 is constructed from Pebax 35D including PTFE and BaSO4. In further examples, the outer layer 147 is constructed from NEUSOFT 597-50, the inner layer 146 is constructed from Pebax 25D including PTFE and BaSO4, and the reinforcing member 145 is constructed from Pebax 4033. In another example, the outer layer 147 is constructed from NEUSOFT 597-50, the inner layer 146 is constructed from Pebax 25D including PTFE and BaSO4, and the reinforcing member 145 is constructed from Pebax 5533.

In some aspects, the reinforcing member 145 can comprise any of the polymers disclosed herein. In some aspects, the reinforcing member 145 can comprise the first compound disclosed above. Yet in other aspects, the reinforcing member 145 can comprise the second compound disclosed above. While in still further aspects, the reinforcing member 145 can comprise the first compound. Yet in still further aspects, the reinforcing member 145 can comprise any polymers that are known in the art and suitable for the desired application. In some aspects, the reinforcing member 145 can comprise polyether block amide, polyurethane, or a combination thereof. While in still further aspects, the reinforcing member 145 is a polyether block amide, for example PEBAX®. While in still further aspects, the reinforcing member 145 is a polyurethane. In such exemplary aspects, the reinforcing member 145 does not comprise a solid lubricant filler, such as a PTFE. In yet other aspects, the reinforcing member 145 does not comprise an inorganic filler. In still further aspects, the reinforcing member 145 can comprise a polymer comprising PEBAX® or polyurethane having a Shore D durometer between about 45 D to about 90D, including exemplary values of about 50D, about 55D, about 60D, about 65D, about 70D, about 72D, about 75D, about 80D, and about 85D.

In yet further aspects, the reinforcing member 145 can comprise a polyolefin, in still further aspects, the reinforcing member 145 can comprise a polyethylene, a polypropylene, a graft modified polyethylene or polypropylene. In yet further aspects, the reinforcing member 145 can comprise the grafted low-density polyethylene (LDPE), grafted medium density polyethylene, grafted ultra-low-density polyethylene (ULDPE) grafted high density polyethylene (HDPE), grafted heterogeneously branched linear low-density polyethylene (LLDPE), grafted homogeneously branched linear ethylene polymers and substantially linear ethylene polymers, grafted polypropylene, or ethylene vinyl acetate (EVA), or any combination thereof. In such exemplary aspects, a maleic anhydride or an acrylic acid can be used to graft the disclosed above polymers. In still further aspects, the at least one reinforcing member 145 can comprise a maleic anhydride or an acrylic acid grafted low density polyethylene. In yet further aspects, the at least reinforcing member 145 can comprise a maleic anhydride or an acrylic acid grafted polypropylene. In still further aspects, the reinforcing member 145 can comprise a maleic anhydride or an acrylic acid grafted ethylene vinyl acetate. In still further aspects, the reinforcing member 145 can comprise a maleic anhydride grafter polyolefin sold under a trademark of OREVAC®.

In some aspects, the reinforcing member 145 can bond the inner and outer layers 146, 147 and can also assist bonding of the elongated tubing as a whole to an inner member of the sheath. As an example, the reinforcing member 145 is constructed from a thermally bondable strip of tie layer material. Tie layer material is comprised of polyolefin backbone including, for example, LDPE, LLDPE, EVA, HDPE, PP or polyolefin copolymer with grafted functional group such as maleic anhydride or acrylic acid as described below.

Tie layer thermally bonds to the polyolefin-like HDPE inner layer 146 and is extruded as a strip in polyamide, co-polyamides, or polyurethane layer of the outer jacket 140. Possible tie layer material for thermally bondable tie layer includes OREVAC® Grafted Polyolefins available from Arkema. In some example, maleic anhydride grafted LLDPE (Linear Low Density Polyethylene) Orevac 18300M is used as a strip. In some examples, the thermally bondable strip is fused to inner layer 146 using heat and/or compression.

In still further aspects, the outer jacket 140 as disclosed herein comprising the reinforcement member can exhibit an expansion force of less than about 50 N, less than about 49N, less than about 48N, less than about 47N, less than about 46N, less than about 45N, less than about 44N, less than about 43N, less than about 42N, less than about 41N, or even less than about 40N.

In still further aspects, the outer jacket as disclosed herein that comprises the reinforcement member can exhibit a burst pressure greater than about 8 psi, greater than about 8.5 psi, greater than about 9 psi, greater than about 9.5 psi, greater than about 10 psi, greater than about 10.5 psi, greater than about 11 psi, greater than about 11.5 psi, about 12 psi, greater than about 12.5 psi, greater than about 13 psi, greater than about 13.5 psi, greater than about 14 psi, greater than about 14.5 psi, or greater than about 15 psi.

Various methods can be used to produce the sheaths discussed above and below, throughout the present disclosure. For example, a method of making the sheath shown in FIGS. 2A-2D can comprise providing a mandrel and applying an inner layer on the mandrel, such as by spray coating or dip coating the mandrel. An intermediate layer, such as a mesh structure, can then be mounted on the inner layer. An outer layer can be applied over the intermediate layer, such as by a second spray coating or dip coating step. Methods can comprise etching or surface treating at least a portion of the inner layer. Also, methods can comprise providing one or more notches and/or cuts in the inner layer and/or the outer layer. Cuts and/or notches can be provided by, for example, laser cutting or etching one or more layers.

In some examples of methods of making a sheath such as the sheaths illustrated in FIGS. 2A-2D, layers can be pre-formed and mounted on a mandrel, and then fused or thermally bonded together. For example, in one method, an inner layer is applied to a mandrel. An intermediate layer can be applied to the outer surface of the inner layer. An outer layer can be applied to the outer surface of the intermediate layer. Heat shrink tubing can be applied, and the assembly heated, such that the inner layer, the intermediate layer, and/or the outer layer are thermally bonded and compressed together under the heat shrink tubing.

Figure 30:
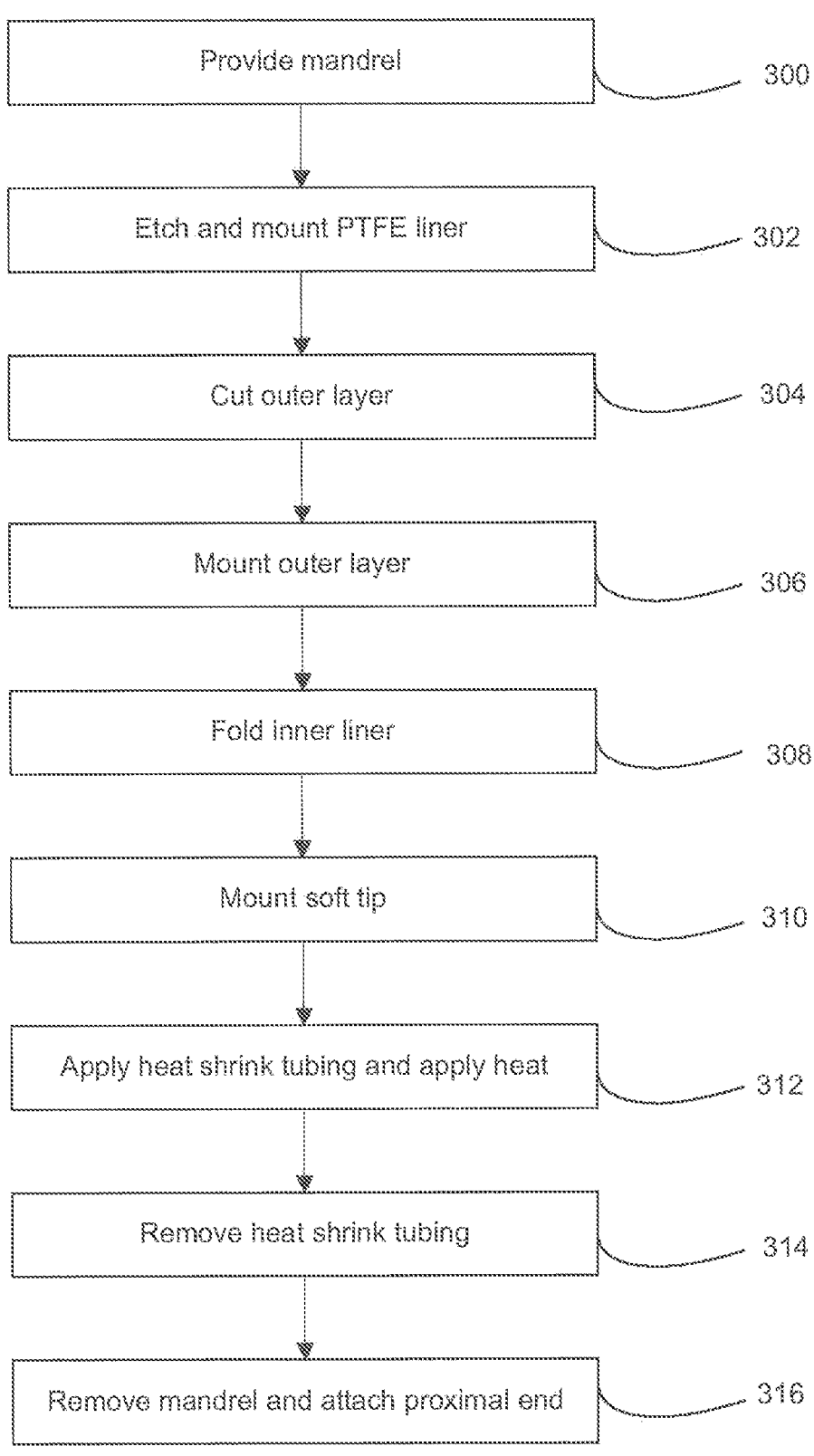
FIG. 30 illustrates a block diagram of one example of a method of making a sheath according to the present disclosure.
Figures 32A, 32B, 32C, 32D, 32E:
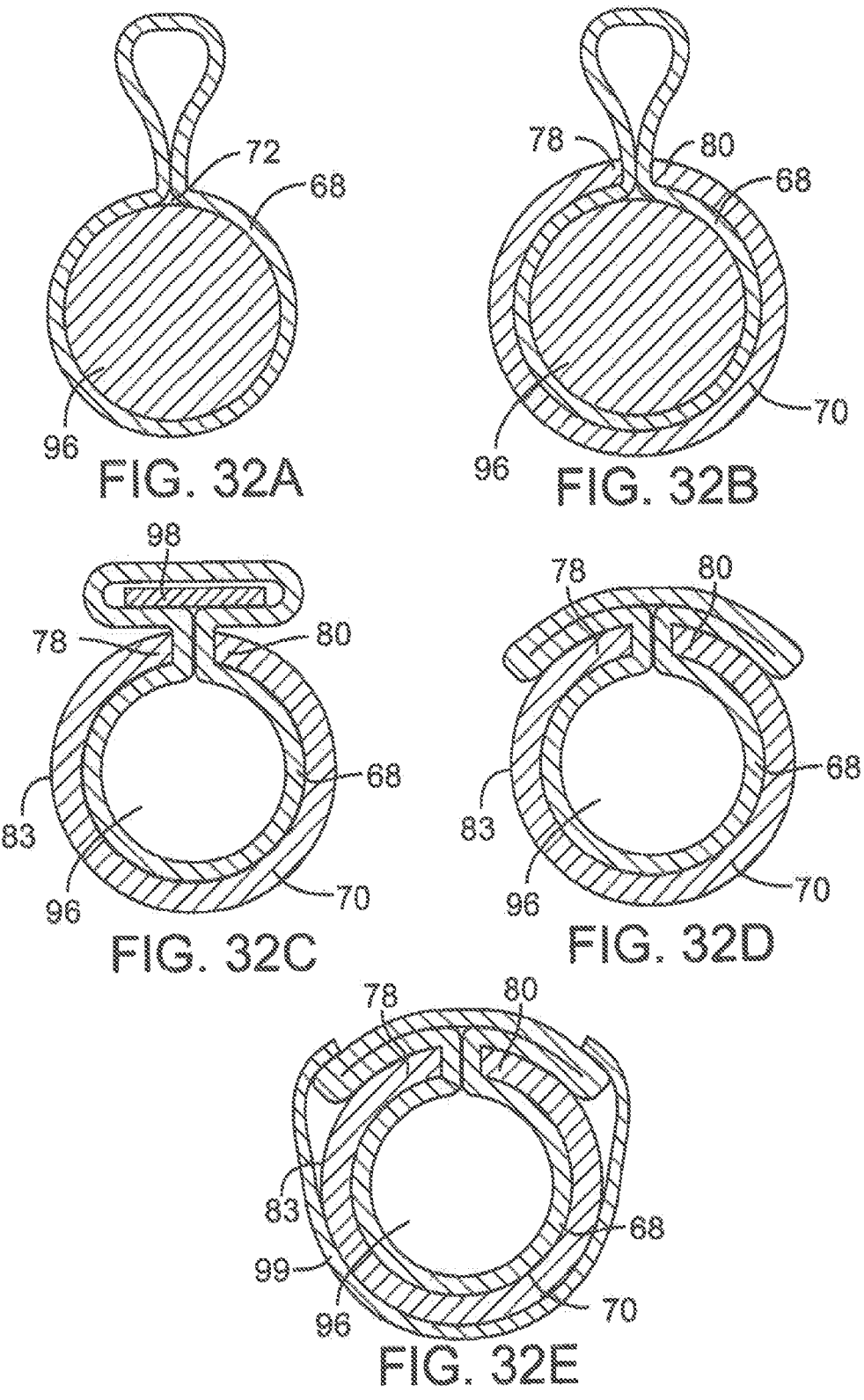

FIG. 30 illustrates a block diagram of one method of producing a sheath for use with a delivery apparatus in minimally invasive surgery. One or more mandrels can be provided (step 300). The mandrel can be provided with an exterior coating, such as a Teflon® coating, and the mandrel's diameter can be predetermined, based on the desired size of the resulting sheath. A liner that will become the inner polymeric layer of the sheath, such as a PTFE or high density polyethylene liner, can be mounted on the mandrel (step 302). The liner can be etched and/or surface treated prior to being mounted on the mandrel, according to conventional etching and surface treatment methods. FIG. 32A illustrates a section view of a sheath at steps 300 and 302 of FIG. 30. A coated mandrel 96 is inserted within the lumen 72 of the inner polymeric layer 68. The circumference of the inner polymeric layer 68 is larger than the circumference of the mandrel 96, such that an excess portion of the inner polymeric layer 68 can be gathered above the mandrel 96.

A layer of material that will become the outer polymeric tubular layer, such as a layer comprising polyurethane or polyolefin, can be cut or notched through all, substantially all, or a part of the thickness of the layer (step 304). Such a cut or notch can extend longitudinally along the length of the layer and can extend along substantially the entire length of the outer polymeric tubular layer. In alternative examples, the cut or notch can be provided along only a portion of the outer polymeric tubular layer. For example, the outer poly-meric tubular layer can be cut starting at the distal end of the outer polymeric tubular layer, with the cut ending before the proximal end of the outer polymeric tubular layer. In one example, the cut can end at a transition, where the outer diameter of the outer polymeric tubular layer increases or decreases. In one specific example, the cut or notch can extend longitudinally along about 75% of the length of the sheath.

The cut or notched outer polymeric tubular layer can be applied, positioned, adhered, mounted, thermally fused or bonded, dip coated, and/or otherwise coupled to the etched inner liner (step 306). FIG. 32B shows a section view of the sheath at step 306 of FIG. 30, with outer polymeric tubular layer 70 applied to the inner polymeric layer 68 such that a portion of the inner polymeric layer 68 extends between the cut formed between first and second portions 78, 80 of the outer polymeric tubular layer 70.

In alternative examples, the outer polymeric tubular layer can be notched or cut after being mounted on the inner liner/mandrel assembly. The outer polymeric tubular layer can optionally be provided with a hydrophilic coating and/or provided with additional layers, such as being dip coated with polyurethane. Some portion of the inner liner can protrude through the cut in the outer polymeric tubular layer after such outer polymeric tubular layer is mounted onto the inner liner/mandrel arrangement. Using, for example, a split tool, the protruding portion of the inner liner can be folded down onto the outer surface of the outer polymeric tubular layer (step 308). In some examples, the protruding portion of the inner liner is folded down along the entire length of the resulting sheath, while in other examples, the protruding portion of the inner liner is only present along a portion of the length of the sheath, or is only folded down along a portion of the length of the resulting sheath. FIG. 32C shows a section view of the sheath at step 308 of FIG. 30. A split tool 98 is used to fold the excess portion of inner polymeric layer 68 over a portion of the outer surface 83 of the outer polymeric tubular layer 70. FIG. 32D shows a section view of the sheath after completion of step 308 of FIG. 30. Split tool 98 has been removed, and folding of the excess portion of the inner polymeric layer 68 has been completed. FIG. 32E shows a section view of an outer covering, such as outer polymeric covering 99, that can be applied such that it overlaps a portion of the folded portion of inner polymeric layer 68. The outer polymeric covering 99 contacts at least a portion of the outer surface 83 of the outer polymeric tubular layer 70.

A soft, atraumatic tip can be provided at the distal end of the resulting sheath (step 310). Additional outer layers can also be applied, if desired. Then, a layer of heat shrink tubing, such as fluorinated ethylene propylene (FEP) heat shrink tubing, can be positioned over the entire assembly (step 312). An appropriate amount of heat is applied, thus shrinking the heat shrink tubing and compressing the layers of the sheath together, such that components of the sheath can be thermally bonded or fused together where desired.

Once the components of the sheath have been bonded together, the heat shrink tubing can be removed (step 314). Finally, the proximal end of the sheath can be adhered or otherwise attached to a housing of a catheter assembly, and the sheath can be removed from the mandrel (step 316).

Figure 31:
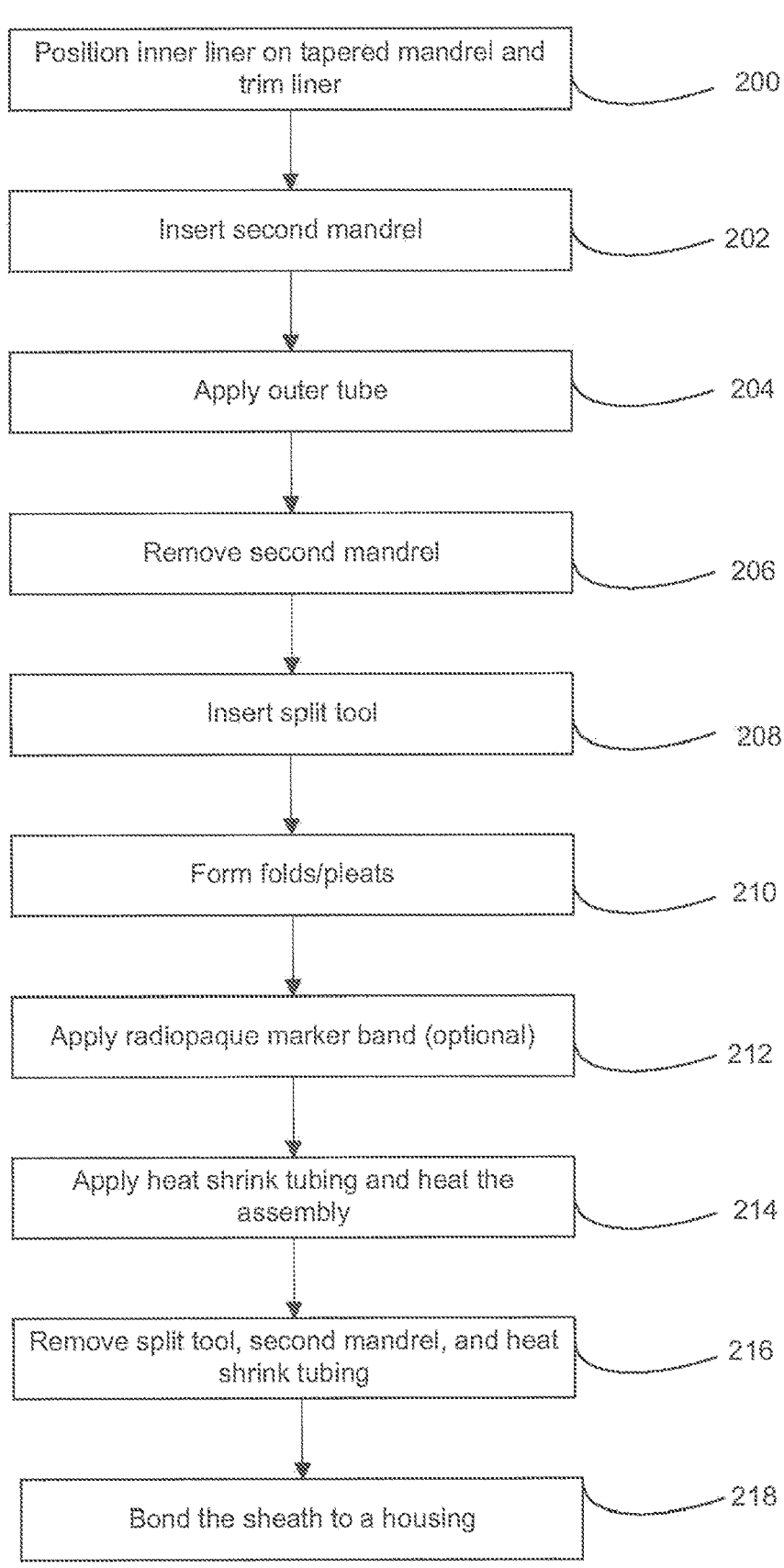
FIG. 31 illustrates a block diagram of another example of a method of making a sheath according to the present disclosure.

FIG. 31 illustrates a block diagram of an alternative example of a method of making a sheath. An inner liner, such as an etched PTFE tubing can be applied to a tapered mandrel, such as a 16 Fr tapered mandrel, and trimmed to an appropriate length (step 200). A second mandrel, such as a 0.070 inches diameter mandrel, can be inserted in the lumen of the inner liner such that the mandrels are arranged side by side in the inner liner (step 202). FIG. 32F shows a section view of a sheath at steps 200 and 202 of FIG. 31. An inner liner or inner polymeric layer 68 is applied on a first, tapered, mandrel 96. A second mandrel 97 is inserted into the lumen 72 of the inner polymeric layer 68 created by the excess portion of the inner polymeric layer 68, as described.

A notched or cut outer polymeric tubular layer, such as high density polyethylene tubing that has been notched or cut longitudinally, can be slid onto the tapered mandrel and a portion of the inner liner, starting at the distal end of the tapered mandrel (step 204). The second mandrel can then be removed (step 206). FIG. 32G illustrates a perspective view of the sheath at steps 204 and 206 of FIG. 31. A outer polymeric tubular layer 70 having a longitudinal cut is applied over the tapered mandrel 96 and inner polymeric layer 68. The outer tubular layer conforms to the portion of the inner polymeric layer around the tapered mandrel 96, and the portion of the inner polymeric layer 68 around the second mandrel 97 extends through the longitudinal cut in the outer polymeric tubular layer 70.

A split tool can be inserted into the portion of the lumen of the inner liner that was previously occupied by the second mandrel (step 208). The split tool can then be used to form folds and/or pleats in the excess portion of the inner liner which now extends through the longitudinal cut in the outer polymeric tubular layer (step 210). A radiopaque marker band can optionally be applied at the distal end of the sheath (step 212). Heat shrink tubing, such as FEP heat shrink tubing, can be applied over the entire sheath, and heat can be applied to compress the components of the sheath and bond or fuse them together (step 214). The split tool, heat shrink tubing, and second mandrel can then be removed (step 216). The sheath can then be utilized with a delivery apparatus, such as by bonding the proximal end of the sheath to a polycarbonate housing of a delivery apparatus or catheter assembly (step 218).

FIG. 32H illustrates an elevation view of the sheath at step 218 of FIG. 31. The sheath 66, made according to described methods and processes, can be attached or bonded to a housing 101, such as by bonding the proximal end of the sheath 66 to the polycarbonate housing 101.

In another example, disclosed expandable sheaths can be made using a reflowed mandrel process. A mandrel can be provided, with the size of the mandrel defining the inner diameter of the sheath lumen in its resting configuration. A tube of material, such as a PTFE tube that will become the sheath's inner liner, can be provided with an inner diameter greater than that of the mandrel (e.g., a 9 mm PTFE tube can be mounted on a 6 mm mandrel). The PTFE tube can be mounted on the mandrel and prepared into the final folded configuration by folding the excess material of the PTFE tube over to one or both sides. An HDPE tube that will serve as the outer layer can then be placed over the PTFE liner. The two layer assembly can then be thermally fused together. For example, a reflow process can be performed where the assembly is heated to a temperature high enough such that the inner and/or outer layers are at least partially melted and are then fused together as the heat is removed and the assembly cools.

An elastic cover can be placed over at least part of the fused layers (e.g., over a proximal section of the sheath) and held in place using a thermal process. In some examples, the same thermal process can bond the layers of the sheath and the elastic cover. In other examples, a first thermal process can be used to fuse the layers of the sheath, and a second thermal process can be used to secure the elastic cover to the sheath. In some examples, the elastic cover can be heat shrink tubing that is applied over the expandable sheath, and heated to a temperature high enough to cause the tubing to shrink around the sheath. In some examples, a distal soft tip can then be attached to the shaft of the expandable sheath.

In some examples, the outer layer can be co-extruded with an adhesive layer, such as a layer formed from Tecoflex™, such that the Tecoflex™ is positioned on an inner surface of the outer layer—in this manner the Tecoflex™ will be positioned between the inner and outer layers in the completed sheath. In these examples, an HDPE tube can be provided with a coating of Tecoflex™ on the inner surface. The HDPE tube can be slit along the length of the tube to open and flatten it, and then cut using a template in some examples. For example, for specific applications, portions of the outer layer can be cut and removed using a template. The cut HDPE can then be placed on the inner layer on the mandrel. In some examples, only a portion of the outer layer will have the adhesive Tecoflex™. In these examples, the sections without Tecoflex™ will only be partially fused to the inner layer. In some examples, the entire inner surface of the outer layer will have the Tecoflex™, and the inner surface of the outer layer can be positioned so that it contacts the inner layer on the mandrel. To position the inner and outer layers as shown in the sheath of FIG. 39, the folded portion of the inner layer can be lifted up, and an edge of the outer layer can be tucked beneath the fold.

Sheaths of the present disclosure can be used with various methods of introducing a prosthetic device into a patient's vasculature. One such method comprises positioning an expandable sheath in a patient's vessel, passing a device through the introducer sheath, which causes a portion of the sheath surrounding the device to expand and accommodate the profile of the device, and automatically retracting the expanded portion of the sheath to its original size after the device has passed through the expanded portion. In some methods, the expandable sheath can be sutured to the patient's skin at the insertion site so that once the sheath is inserted the proper distance within the patient's vasculature, it does not move once the implantable device starts to travel through the sheath.

Disclosed examples of an expandable sheath can be used with other delivery and minimally invasive surgical components, such as an introducer and loader. In one example, the expandable sheath can be flushed to purge any air within the sheath, using, for example, flush port 103 (FIG. 35). An introducer can be inserted into the expandable sheath and the introducer/sheath combination can be fully inserted into vasculature over a guiding device, such as a 0.35" guidewire. Preferably, the seam formed by the intersection of the folded portion of the inner layer and the overlapping portion of the outer layer can be positioned such it is oriented downward (posterior). Once the sheath and introducer are fully inserted into a patient's vasculature, in some examples, the expandable sheath can be sutured in place at the insertion site. In this manner, the expandable sheath can be substantially prevented from moving once positioned within the patient.

The introducer can then be removed and a medical device, such as a transcatheter heart valve can be inserted into the sheath, in some instances using a loader. Such methods can additionally comprise placing the tissue heart valve in a crimped state on the distal end portion of an elongated delivery apparatus, and inserting the elongated delivery device with the crimped valve into and through the expandable sheath. Next, the delivery apparatus can be advanced through the patient's vasculature to the treatment site, where the valve can be implanted.

Typically, the medical device has a greater outer diameter than the diameter of the sheath in its original configuration. The medical device can be advanced through the expandable sheath towards the implantation site, and the expandable sheath can locally expand to accommodate the medical device as the device passes through. The radial force exerted by the medical device can be sufficient to locally expand the sheath to an expanded diameter (e.g., the expanded configuration) just in the area where the medical device is currently located. Once the medical device passes a particular location of the sheath, the sheath can at least partially contract to the smaller diameter of its original configuration. The expandable sheath can thus be expanded without the use of inflatable balloons or other dilators. Once the medical device is implanted, the sheath and any sutures holding in place can be removed. In some examples, it is preferable to remove the sheath without rotating it.

EXEMPLARY ASPECTS

Example 1: An expandable sheath comprising; an inner tubular layer comprising a longitudinal slit and partially defining an inner lumen, an outer tubular layer enveloping the inner layer, the outer tubular layer comprising a longitudinally extending, folded flap that overlies a portion of an outer surface of the outer layer when the sheath is in an unexpanded state, a tie layer positioned between and adhering the inner tubular layer to the outer tubular layer, wherein an outwardly directed radial force from a prosthetic device moving through the inner lumen widens the longitudinal slit and unfolds the folded flap to allow expansion of the sheath.

Example 2: The sheath according to any example herein, particularly example 1, wherein a base of the folded flap is positioned radially outwardly from the longitudinal slit.

Example 3: The sheath according to any example herein, particularly examples 1 or 2, wherein the folded flap includes a longitudinally extending overlying portion separated from a longitudinally extending underlying portion by a longitudinally extending crease.

Example 4: The sheath according to any example herein, particularly example 3, wherein the underlying portion contacts an outer surface of the outer tubular layer when the sheath is in the unexpanded state.

Example 5: The sheath according to any example herein, particularly examples 3-4, wherein a base of the folded flap extends the length of the outer tubular layer, and wherein the overlying portion and the underlying portion extend between the base and the crease.

Example 6: The sheath according to any example herein, particularly examples 3-5, wherein the overlying portion, the underlying portion, or both have a wall thickness that is thinner than the remainder of the outer tubular layer.

Example 7: The sheath according to any example herein, particularly examples 1-6, wherein the longitudinally extending flap extends around about 20% to about 40% of an outer circumference of the outer tubular layer when the sheath is in an unexpanded state.

Example 8: The sheath according to any example herein, particularly examples 1-7, wherein the outer tubular layer is formed of a material having a tensile modulus of at least 300 MPa.

Example 9: The sheath according to any example herein, particularly example 8, wherein the outer tubular layer is formed of a material having a tensile modulus from 300 MPa to 2,000 MPa.

Example 10: The sheath according to any example herein, particularly examples 1-9, wherein the outer tubular layer is formed of a material having an ultimate tensile strength of at least 50 MPa.

Example 11: The sheath according to any example herein, particularly examples 1-10, wherein the outer tubular layer is formed of a shape memory material.

Example 12: The sheath according to any example herein, particularly examples 1-11, wherein the outer tubular layer is formed of a polyamide, co-polyamide, polyether block amide (PEBAX), or a blend of polyamide.

Example 13: The sheath according to any example herein, particularly examples 1-12, wherein the outer tubular layer further comprises at least one additional longitudinally extending, folded flap that overlies a portion of the outer surface of the outer layer when the sheath is in an unexpanded state.

Example 14: The sheath according to any example herein, particularly examples 1-13, wherein the outer surface of the outer tubular layer further comprises a hydrophilic coating.

Example 15: The sheath according to any example herein, particularly examples 1-14, wherein the longitudinal slit extends the full length of the inner tubular layer.

Example 16: The sheath according to any example herein, particularly examples 1-15, wherein the inner tubular layer comprises a first longitudinally extending end and a second longitudinally extending end, the first and second longitudinally extending ends defining the longitudinal slit.

Example 17: The sheath according to any example herein, particularly examples 1-16, wherein the inner tubular layer comprises a material with a static or dynamic coefficient of friction less than 0.3.

Example 18: The sheath according to any example herein, particularly examples 1-17, wherein the inner tubular layer extends around at least 80% of a circumference of the inner lumen when the sheath is in an unexpanded state.

Example 19: The sheath according to any example herein, particularly examples 1-18, wherein the inner tubular layer is formed of a material having a tensile modulus of at least 300 MPa.

Example 20: The sheath according to any example herein, particularly example 1-19, wherein the inner tubular layer comprises HDPE or a fluoropolymer.

Example 21: The sheath according to any example herein, particularly examples 1-20, wherein the tie layer comprises a polyurethane or functionalized polyolefin.

Example 22: The sheath according to any example herein, particularly examples 1-21 further comprising an elastomeric outer jacket enveloping the outer tubular layer.

Example 23: A method of delivering a prosthetic device to a procedure site, the method comprising: inserting an expandable sheath into the vasculature of a subject, advancing the prosthetic device through an inner lumen of the expandable sheath, the prosthetic device applying an outwardly directed radial force to an inner tubular layer of the expandable sheath, widening a longitudinal slit in the inner tubular layer via the outwardly directed radial force, unfolding a longitudinally extending flap of an outer tubular layer via the outwardly directed radial force, narrowing the longitudinal slit of the inner tubular layer once the outwardly directed radial force has ceased, and delivering the prosthetic device to a procedure site.

Example 24: The method according to any example herein, particularly example 23, wherein the unfolding of the flap occurs at a position radially outward from the longitudinal slit.

Example 25: The method according to any example herein, particularly examples 23 or 24, further comprising at least partially refolding the longitudinally extending flap once the advancing prosthetic device ceases to apply the outwardly directed radial force.

Example 26: The method according to any example herein, particularly examples 23-25, wherein the longitudinally extending flap is refolded by a shape memory bias of the outer tubular layer toward a folded state.

Example 27: The method according to any example herein, particularly examples 23-26, further comprising applying an inwardly directed radial force to an outer surface of the outer tubular layer to refold the longitudinally extending flap.

Example 28: The method according to any example herein, particularly example 27, wherein the inwardly directed radial force is applied by an elastomeric outer jacket.

Example 29: The method according to any example herein, particularly examples 23-28, further comprising transmitting the outwardly directed radial force from the inner tubular layer, through a tie layer, and to the outer tubular layer.

Example 30: The method according to any example herein, particularly examples 23-29, wherein the widening of the longitudinal slit and the subsequent narrowing of the longitudinal slit travels the full length of the expandable sheath.

Example 31: The method according to any example herein, particularly examples 23-30, wherein unfolding a longitudinally extending flap comprises sliding a longitudinally extending overlying portion circumferentially against a longitudinally extending underlying portion.

Example 32: The method according to any example herein, particularly example 31, wherein unfolding a longitudinally extending flap comprises sliding the longitudinally extending underlying portion circumferentially against an outer surface of the outer tubular layer.

Example 33: A method of making an expandable sheath, the method comprising: loading an inner layer onto a tapered mandrel; applying heat to inner layer; flaring a proximal section of inner layer under heat; applying a tie layer to a body section of the inner layer; cutting a longitudinal slit in the inner layer and tie layer; loading inner layer and tie layer with longitudinal slit onto a (second) mandrel; loading an outer layer over the tie layer; folding the outer layer to create a longitudinally extending flap; heat setting the folded outer layer; and removing the expandable sheath from mandrel.

Example 34: The method according to any example herein, particularly example 33, wherein the tie layer is applied after expanding the inner layer with air pressure.

Example 35: The method according to any example herein, particularly examples 33 or 34, further comprising adhering the tie layer to the inner layer using heat shrink tubing and removing the heat shrink tubing from the tie layer.

Example 36: The method according to any example herein, particularly example 35, further comprising removing the heat shrink tubing from the tie layer.

Example 37: The method according to any example herein, particularly examples 33-36, wherein heat setting the folded outer layer further comprises applying heat shrink tubing to the folded outer layer and removing the heat shrink tubing after heat setting the folded outer layer.

Example 38: The method according to any example herein, particularly example 37, further comprising removing the heat shrink tubing after heat setting the folded outer layer.

Example 39: A sheath for delivering a medical device, the sheath comprising: a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer; a discontinuous outer layer extending at least partially around the inner layer, the outer layer having an overlapping portion and an underlying portion, at least a portion of the folded portion of the inner layer is positioned between the overlapping portion and the underlying portion; an adhesive layer (e.g., tie layer) is provided between the inner layer and the outer layer and at least partially adhering the inner layer to the outer layer; and an outer jacket extending around the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the medical device passes through the lumen.

Example 40: The sheath according to any example herein, particularly example 39, wherein the outer jacket comprises an elastomeric material.

Example 41: The sheath according to any example herein, particularly examples 39 or 40, wherein the outer jacket comprises a thermoplastic polyurethane (e.g., Neusoft, and Tecoflex™ 80 A B20).

Example 42: The sheath according to any example herein, particularly examples 39-41, wherein the outer jacket comprises an elastomer (e.g., an elastic polymer) with shore hardness (durometer) in the ranging between about 10 and about 95 Shore A.

Example 43: The sheath according to any example herein, particularly examples 39-42, wherein the outer jacket comprises an elastomer with an elongation at break of ranging between about 40% and about 800%.

Example 44: The sheath according to any example herein, particularly examples 39-43, wherein the outer jacket comprises an elastomer with a wall thickness ranging between about 0.003 inches and about 0.015 inches.

Example 45: The sheath according to any example herein, particularly examples 39-44, wherein the wall thickness of the outer jacket varies along a length of the outer jacket.

Example 46: The sheath according to any example herein, particularly example 45, wherein the wall thickness of the outer jacket is greater along a length of the outer jacket adjacent the proximal end of the sheath.

Example 47: The sheath according to any example herein, particularly examples 45-46, wherein the sheath includes a tapered segment adjacent the proximal end of the sheath, wherein the thickness of the outer jacket is greater along the tapered segment.

Example 48: The sheath according to any example herein, particularly examples 39-47, wherein the outer jacket is bonded to the outer layer.

Example 49: The sheath according to any example herein, particularly examples 39-48, wherein the outer jacket is bonded to the outer layer at a proximal end of the outer layer.

Example 50: The sheath according to any example herein, particularly examples 39-49, wherein the outer jacket is bonded to the outer layer at a distal end of the outer layer.

Example 51: The sheath according to any example herein, particularly examples 39-50, wherein the outer jacket is bonded to the outer layer along a length of the outer layer between the proximal and distal ends of the outer layer.

Example 52: The sheath according to any example herein, particularly examples 39-50, wherein a distal end of the outer jacket is bonded to the inner layer.

Example 53: The sheath according to any example herein, particularly example 52, wherein the outer jacket is bonded to a distal end surface of the inner layer.

Example 54: The sheath according to any example herein, particularly examples 39-53, wherein the outer jacket is bonded to at least one of a proximal end of the outer layer, a distal end of the outer layer, and a distal end of the inner layer by a chemical and/or mechanical fastener.

Example 55: The sheath according to any example herein, particularly example 54, wherein the mechanical fastener includes thermally bonded coupling between the outer jacket and at least one of the outer layer and the inner layer.

Example 56: The sheath according to any example herein, particularly examples 39-54, wherein the outer jacket extends over an entire length of the outer layer.

Example 57: The sheath according to any example herein, particularly examples 39-56, wherein the first fold is configured to move closer to the second fold to shorten the folded portion at a local axial location during passage of the medical device through the lumen, and wherein shortening of the folded portion corresponds with a local expansion of the lumen.

Example 58: The sheath according to any example herein, particularly examples 39-57, wherein the inner layer extends through a longitudinally extending opening provided in the outer layer when the outer layer is expanded.

Example 59: The sheath according to any example herein, particularly example 58, wherein the longitudinally extending opening is provided between a longitudinally extending edge of the overlapping portion and a longitudinally extending edge of the underlying portion.

Example 60: The sheath according to any example herein, particularly examples 39-59, wherein the inner layer is composed of an etched PTFE.

Example 61: The sheath according to any example herein, particularly example 60, wherein the inner layer is composed of a fully etched PTFE.

Example 62: The sheath according to any example herein, particularly example 60, wherein the inner layer is composed of a partially etched PTFE.

Example 63: The sheath according to any example herein, particularly example 62, wherein unetched portions of an outer surface of the inner layer extend longitudinally along a length of the inner layer and/or circumferentially around a length of a circumference of the inner layer.

Example 64: The sheath according to any example herein, particularly examples 62-63, wherein unetched portions of the inner layer are provided along portions of the inner layer that contact an outer surface of the outer layer.

Example 65: The sheath according to any example herein, particularly examples 62-63, wherein unetched portions of the inner layer are provided along those locations excluding the tie layer, wherein the surface of the inner layer adjacent the underlying portion of the outer layer, when the sheath is not expanded, are unetched.

Example 66: The sheath according to any example herein, particularly examples 39-65, wherein the inner layer has a wall thickness ranging between about 0.002 inches and about 0.006 inches.

Example 67: The sheath according to any example herein, particularly examples 39-65, wherein the inner layer has a wall thickness ranging between about 0.003 inches and about 0.005 inches.

Example 68: The sheath according to any example herein, particularly examples 39-65, wherein the inner layer has a wall thickness ranging between about 0.0035 inches and about 0.0045 inches.

Example 69: The sheath according to any example herein, particularly examples 39-68, wherein the outer layer exerts a radially inward force on the inner layer.

Example 70: The sheath according to any example herein, particularly examples 39-68, wherein the outer layer is composed of at least one polymeric material.

Example 71: The sheath according to any example herein, particularly example 70, wherein the outer layer is composed of at least one of HDPE, nylon, and polypropylene.

Example 72: The sheath according to any example herein, particularly examples 39-71, wherein the outer layer has a wall thickness ranging between about 0.007 inches and about 0.013 inches.

Example 73: The sheath according to any example herein, particularly examples 39-71, wherein the outer layer has a wall thickness ranging between about 0.008 inches and about 0.012 inches.

Example 74: The sheath according to any example herein, particularly examples 39-71, wherein the outer layer has a wall thickness ranging between about 0.009 inches and about 0.011 inches.

Example 75: The sheath according to any example herein, particularly examples 39-74, wherein the tie layer extends at least partially around an outer surface of the inner layer.

Example 76: The sheath according to any example herein, particularly example 75, wherein the tie layer extends around an entirety of the outer surface of the inner layer.

Example 77: The sheath according to any example herein, particularly examples 39-74, wherein the tie layer extends at least partially around an inner surface of the outer layer.

Example 78: The sheath according to any example herein, particularly example 77, wherein the tie layer extends around an entirety of an inner surface of the outer layer.

Example 79: The sheath according to any example herein, particularly examples 39-78, wherein the tie layer extends between the outer layer and the overlapping folded portion of the inner layer.

Example 80: The sheath according to any example herein, particularly example 79, wherein the tie layer extends between an outer surface of the overlapping folded portion of the inner layer and a corresponding surface of the overlapping portion of the outer layer.

Example 81: The sheath according to any example herein, particularly examples 79-80, wherein the tie layer does not extend between an inner surface of the overlapping folded portion of the inner layer and a corresponding surface of the underlying portion of the outer surface of the outer layer.

Example 82: The sheath according to any example herein, particularly examples 39-81, wherein the tie layer adheres at least a portion of the inner layer to a corresponding portion of the outer layer.

Example 83: The sheath according to any example herein, particularly examples 39-82, wherein the tie layer comprises a material having a shore A hardness (durometer) less than 90 A.

Example 84: The sheath according to any example herein, particularly example 83, wherein the tie layer is composed thermoplastic polyurethane.

Example 85: The sheath according to any example herein, particularly example 84, wherein the tie layer is composed of an aliphatic polyether-based thermoplastic polyurethane (TPU).

Example 86: The sheath according to any example herein, particularly example 85, wherein the tie layer is composed of Tecoflex™ 80 A.

Example 87: The sheath according to any example herein, particularly example 84, wherein the tie layer is composed of an aromatic polyether or polyesters based thermoplastic polyurethane.

Example 88: The sheath according to any example herein, particularly example 87, wherein the tie layer is composed of Pellethane™ 80 A.

Example 89: The sheath according to any example herein, particularly examples 39-82, wherein the tie layer is composed of a polyolefin or polyamide.

Example 90: The sheath according to any example herein, particularly example 89, wherein the tie layer is composed of a polyolefin (PE, PP, or EVA) modified with maleic anhydride.

Example 91: The sheath according to any example herein, particularly example 90, wherein the tie layer is composed of an Orevac™ resin.

Example 92: The sheath according to any example herein, particularly examples 39-91, wherein the tie layer has a wall thickness ranging between about 0.002 inches and about 0.005 inches.

Example 93: The sheath according to any example herein, particularly examples 39-91, wherein the tie layer has a wall thickness ranging between about 0.0025 inches and about 0.0040 inches.

Example 94: The sheath according to any example herein, particularly examples 39-91, wherein the tie layer has a wall thickness ranging between about 0.0025 inches and about 0.0035 inches.

Example 95: A sheath for delivering a medical device, the sheath comprising: a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer; a discontinuous outer layer extending at least partially around the inner layer, the outer layer having an overlapping portion and an underlying portion, at least a portion of the folded portion of the inner layer is positioned between the overlapping portion and the underlying portion; a tie layer provided between the inner layer and the outer layer and at least partially adhering the inner layer to the outer layer; and an outer jacket extending around the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the prosthetic device passes through the lumen, wherein a lubricant is provided between the outer jacket and the outer layer.

Example 96: The sheath according to any example herein, particularly example 95, wherein the lubricant is provided on an outer surface of the outer layer proximate a longitudinally extending edge of the overlapping portion.

Example 97: The sheath according to any example herein, particularly examples 95-96, wherein at least a portion of the folded portion of the inner layer extends beyond the longitudinally extending edge of the overlapping portion and along an outer surface of the outer layer.

Example 98: The sheath according to any example herein, particularly example 97, wherein the lubricant is provided along the portion the folded portion of the inner layer extending along the outer surface of the outer layer.

Example 99: The sheath according to any example herein, particularly example 98, wherein the lubricant is provided along a portion of the outer surface of the outer layer adjacent the portion the folded portion of the inner layer extending along the outer surface of the outer layer.

Example 100: The sheath according to any example herein, particularly examples 95-99, wherein the lubricant reduces friction between the outer layer and the outer jacket during expansion of the sheath.

Example 101: The sheath according to any example herein, particularly examples 95-100, wherein the lubricant reduces friction between the inner layer and the outer jacket during expansion of the sheath.

Example 102: The sheath according to any example herein, particularly examples 95-101, wherein the lubricant is applied as a band around a portion of the circumference of the outer layer, the band of lubricant extending longitudinally along a length of the outer layer.

Example 103: The sheath according to any example herein, particularly examples 95-102, wherein the lubricant is composed of a curable material.

Example 104: The sheath according to any example herein, particularly example 103, wherein the lubricant is curable at room temperature.

Example 105: The sheath according to any example herein, particularly examples 95-104, wherein the lubricant is composed of a medical grade silicone.

Example 106: The sheath according to any example herein, particularly examples 95-105, wherein the lubricant is composed of at least one of Med10-6670, Duraglide™ and/or Christo-Lube™.

Example 107: A method of delivering a prosthetic device to a procedure site, the method comprising; introducing an expandable sheath into the vasculature of a subject, advancing the prosthetic device through an inner lumen of the expandable sheath, the prosthetic device applying an outwardly directed radial force to an inner tubular layer of the expandable sheath, locally expanding the lumen of the sheath at a local axial location due to an outwardly directed radial force exerted by a prosthetic device against an inner surface of the lumen during advancement of the prosthetic device through the local axial location, wherein locally expanding the lumen comprises: moving a first fold of the inner layer circumferentially closer to a second fold of the inner layer and shortening an overlapping portion of the inner layer extending circumferentially between the first and second folds; and expanding an outer layer along at least one elongate gap generally aligned with the axis of the lumen and positioned adjacent to at least one of the folds, wherein expanding the outer layer along at least one elongate gap comprises moving a first portion of the outer layer away from a second portion of the outer layer, wherein the gap is defined between the first and second portions, as the first fold moves closer to the second fold, wherein the inner layer and the outer layer are at least partially adhered via a tie layer extending therebetween, locally contracting the lumen of the sheath at least partially back to an unexpanded configuration as the prosthetic device passes through the lumen; and delivering the prosthetic device to a procedure site.

Example 108: The method according to any example herein, particularly example 107, where an outer jacket extends around the outer layer and provides an inwardly directed radial force on the outer layer.

Example 109: The method according to any example herein, particularly examples 107-108, wherein the tie layer extends between an outer surface of the overlapping folded portion of the inner layer and a corresponding surface of the overlapping portion of the outer layer, the tie layer adhering the inner layer to the outer layer.

Example 110: The method according to any example herein, particularly examples 107-109, wherein the tie layer does not extend between an inner surface of the overlapping folded portion of the inner layer and a corresponding surface of the underlying portion of the outer surface of the outer layer such that the outer layer and the inner layer are not adhered, Wherein during expansion, the inner surface of the overlapping folded portion of the inner layer expands into the elongate gap of the outer layer.

Example 111: The method according to any example herein, particularly examples 107-110, wherein expanding the outer layer along at least one gap further comprises expanding the gap over the overlapping portion of the inner layer.

Example 112: The method according to any example herein, particularly examples 107-111, further comprising expanding the inner layer into the gap.

Example 113: The method according to any example herein, particularly examples 107-112, further comprising merging the first and second folds and eliminating the overlapping portion at the local axial location.

Example 114: The method according to any example herein, particularly examples 107-113, wherein expanding the inner layer at the local axial location into a substantially tubular, unfolded cross-section.

Example 115: The method according to any example herein, particularly examples 107-114, further comprising exerting a radial force on the gap of the outer layer and widening the outer layer along the gap.

Example 116: The method according to any example herein, particularly example 115, further comprising moving one of the folds closer to the gap during application of the radial force.

Example 117: The method according to any example herein, particularly example 116, wherein the gap is adjacent the first fold and further comprising passing the first fold radially under the gap as the first fold moves closer to the second fold.

Example 118: The method according to any example herein, particularly examples 107-117, wherein introducing the prosthetic device comprises introducing a stent-mounted heart valve into the proximal end of the lumen and further comprising extending the stent-mounted heart valve out of the distal end of the elongate lumen.

Example 119: The method according to any example herein, particularly example 118, further comprising expanding the stent-mounted heart valve after it exits the elongate lumen.

Example 120: The method according to any example herein, particularly examples 107-119, wherein a lubricant is provided between the outer jacket and the outer layer proximate a longitudinally extending edge of the overlapping portion, the lubricant reducing friction between the inner layer and the outer jacket during expansion of the sheath.

Example 121: A method of manufacturing a sheath for delivering a medical device, the method comprising: providing a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer; providing a discontinuous outer layer at least partially around the inner layer, the outer layer having an overlapping portion and an underlying portion, at least a portion of the folded portion of the inner layer is positioned between the overlapping portion and the underlying portion; providing a tie layer between the inner layer and the outer layer and at least partially adhering the inner layer to the outer layer; bonding the inner layer to the outer layer; providing a lubricant at a location proximate a longitudinally extending edge of the overlapping portion; and providing an outer jacket around the outer layer and bonding the outer jacket to the outer layer at least one of their proximal and distal ends.

Example 122: The method according to any example herein, particularly example 121, wherein the inner layer is bonded to the outer layer by the tie layer.

Example 123: The method according to any example herein, particularly example 122, wherein the tie layer is provided axially along a length of at least one of the inner and outer layers, wherein the inner layer is bonded to the outer layer axially along the length of the sheath via the tie layer.

Example 124: The method according to any example herein, particularly examples 121-123, wherein the tie layer bonds the inner layer to the outer layer by heat curing.

Example 125: The method according to any example herein, particularly example 124, wherein the tie layer bonds the inner layer to the outer layer by heat curing at room temperature.

Example 126: The method according to any example herein, particularly example 124, wherein the tie layer bonds the inner layer to the outer layer by heat curing at a temperature above room temperature.

Example 127: The method according to any example herein, particularly examples 121-126, wherein the outer layer and the tie layer are co-extruded.

Example 128: The method according to any example herein, particularly examples 121-127, wherein the lubricant is provided on an outer surface of the outer layer proximate a longitudinally extending edge of the overlapping portion.

Example 129: The method according to any example herein, particularly example 128, wherein at least a portion of the folded portion of the inner layer extends beyond the longitudinally extending edge of the overlapping portion and along an outer surface of the outer layer.

Example 130: The method according to any example herein, particularly example 129, wherein the lubricant is provided along the portion the folded portion of the inner layer extending along the outer surface of the outer layer.

Example 131: The method according to any example herein, particularly example 130, wherein the lubricant is provided along a portion of the outer surface of the outer layer adjacent the portion the folded portion of the inner layer extending along the outer surface of the outer layer.

Example 132: The method according to any example herein, particularly examples 121-131, wherein the lubricant is applied as a band extending around a portion of the circumference of the outer layer, the band of lubricant extending longitudinally along a length of the outer layer.

wherein the lubricant is applied to the outer layer before the outer jacket is applied.

Example 133: The method according to any example herein, particularly examples 121-132, wherein the lubricant is composed of a heat curable material.

Example 134: The method according to any example herein, particularly example 133, wherein the lubricant is curable at room temperature.

Example 135: The method according to any example herein, particularly examples 121-134 further comprising: etching at least a portion of an outer surface of the inner layer.

Example 136: The method according to any example herein, particularly example 135, wherein unetched portions of the outer surface of the inner layer extend longitudinally along a length of the inner layer and/or circumferentially around a length of a circumference of the inner layer.

Example 137: The method according to any example herein, particularly examples 135-136, wherein unetched portions of the inner layer are provided along portions of the inner layer that contact the outer layer.

Example 138: The method according to any example herein, particularly examples 135-137, wherein unetched portions of the inner layer are provided along those locations excluding the tie layer.

Example 139: The method according to any example herein, particularly examples 135-138, wherein the surface of the inner layer adjacent the underlying portion of the outer layer, when the sheath is not expanded, are unetched.

Example 140: The method according to any example herein, particularly examples 121-139, wherein the outer jacket is bonded to the outer layer at both the proximal and distal ends of the outer jacket and outer layer.

Example 141: The method according to any example herein, particularly examples 121-140, wherein the outer jacket is bonded to the outer layer of along a length of the outer layer.

Example 142: The method according to any example herein, particularly examples 121-141, wherein the outer jacket is bonded to the outer layer by heat treatment.

Example 143: The method according to any example herein, particularly examples 121-142 further comprising: releasing any bond formed between the inner layer and the underlying portion of the outer layer, wherein the proximal and distal ends of the of the inner layer and the outer layer remain bonded.

Example 144: The method according to any example herein, particularly example 143, wherein the tie layer is not provided along the underlying portion of the outer layer and the bond between the inner layer and outer layer along the tie layer remains intact.

Example 145: The method according to any example herein, particularly examples 143-144, wherein a mandrel is passed at least partially through the lumen of the inner layer to release any bond between the inner layer and the underlying portion of the outer layer.

Example 146: The method according to any example herein, particularly examples 121-145, further comprising: reflowing (re-rolling) the sheath to reduce an outer diameter and regain circular shape.

Example 147: A sheath for delivering a medical device, the sheath comprising: a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer; a discontinuous outer layer extending at least partially around the inner layer, the outer layer having an overlapping portion and an underlying portion, at least a portion of the folded portion of the inner layer is positioned between the overlapping portion and the underlying portion; a coiled wire along a length of the sheath, the coil wire providing uniform bending of the sheath to prevent kinking; a tie layer provided between the inner layer and the outer layer and at least partially adhering the inner layer to the outer layer; and an outer jacket extending around the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the prosthetic device passes through the lumen.

Example 148: The sheath according to any example herein, particularly example 147, wherein the coiled wire is embedded in the outer layer.

Example 149: The sheath according to any example herein, particularly examples 147-148, wherein the coiled wire is co-extruded with the outer layer.

Example 150: The sheath according to any example herein, particularly example 147, wherein the coiled wire is provided between the outer layer and the tie layer.

Example 151: The sheath according to any example herein, particularly example 147, wherein the coiled wire is embedded at least partially within both the outer layer and the tie layer.

Example 152: The sheath according to any example herein, particularly example 147, wherein the coiled wire is provided to an outer surface of the tie layer and the outer layer is reflowed over.

Example 153: The sheath according to any example herein, particularly examples 147-152, wherein the coiled wire is composed of a metal or a polymer wire.

Example 154: The sheath according to any example herein, particularly examples 147-153, wherein the coiled wire is composed of at least one of PET, PEEK, stainless steel, nitinol.

Example 155: The sheath according to any example herein, particularly examples 147-154, wherein the coiled wire defines a helical-shaped path around the longitudinal axis of the sheath.

Example 156: The sheath according to any example herein, particularly examples 147-155, wherein the coiled wire defines an overlapping helical-shaped path around the longitudinal axis of the sheath.

Example 157: The sheath according to any example herein, particularly example 156, wherein the overlapping helical-shaped path defines a continuous diamond pattern along a length of the sheath.

Example 158: The sheath according to any example herein, particularly examples 147-157, wherein the coiled wire is a flat wire.

Example 159: The sheath according to any example herein, particularly examples 147-157, wherein the coiled wire is a round wire.

Example 160: The sheath according to any example herein, particularly examples 147-159, wherein the coiled wire has a thickness of about 0.002" to about 0.008".

Example 161: The sheath according to any example herein, particularly examples 147-158, wherein the coiled wire has a thickness of about 0.003" to about 0.007".

Example 162: The sheath according to any example herein, particularly examples 147-159, wherein the coiled wire has a thickness of about 0.004" to about 0.007".

Example 163: The sheath according to any example herein, particularly examples 147-159, wherein the coiled wire has a thickness of about 0.006".

Example 164: The sheath according to any example herein, particularly examples 147-163, wherein a distance between adjacent coils of the coiled wire corresponds to a diameter of the coiled wire.

Example 165: The sheath according to any example herein, particularly examples 147-164, wherein a distance between adjacent coils of the coiled wire is about 0.006".

Example 166: The sheath according to any example herein, particularly example 165, wherein the coiled wire has a diameter of about 0.006".

Example 167: The sheath according to any example herein, particularly examples 147-166, wherein a lubricant is provided between the outer jacket and the outer layer for reducing friction during expansion of the sheath.

Example 168: The sheath according to any example herein, particularly example 167, wherein the lubricant is provided on an outer surface of the outer layer proximate a longitudinally extending edge of the overlapping portion.

Example 169: The sheath according to any example herein, particularly example 168, wherein at least a portion of the folded portion of the inner layer extends beyond the longitudinally extending edge of the overlapping portion and along an outer surface of the outer layer, wherein the lubricant is provided along the portion the folded portion of the inner layer extending along the outer surface of the outer layer for reducing friction between the inner layer and the outer jacket during expansion of the sheath.

Example 170: A method of delivering a prosthetic device to a procedure site, the method comprising; introducing an expandable sheath into the vasculature of a subject; advancing the prosthetic device through an inner lumen of the expandable sheath, the prosthetic device applying an outwardly directed radial force to an inner tubular layer of the expandable sheath; locally expanding the lumen of the sheath at a local axial location due to an outwardly directed radial force exerted by a medical device against an inner surface of the lumen during advancement of the prosthetic device through the local axial location, wherein locally expanding the lumen comprises: moving a first fold of the inner layer circumferentially closer to a second fold of the inner layer and shortening an overlapping portion of the inner layer extending circumferentially between the first and second folds, and expanding an outer layer along at least one elongate gap generally aligned with the axis of the lumen and positioned adjacent to at least one of the folds, wherein expanding the outer layer along at least one elongate gap comprises moving a first portion of the outer layer away from a second portion of the outer layer, wherein the gap is defined between the first and second portions, as the first fold moves closer to the second fold, wherein a coiled wire structure is embedded in the inner and/or outer layer, the coiled wire increasing the kink resistance and increasing the column strength of the expandable sheath; locally contracting the lumen of the sheath at least partially back to an unexpanded configuration as the prosthetic device passes through the lumen; and delivering the prosthetic device to a procedure site.

Example 171: The method according to any example herein, particularly example 170, wherein the coiled wire provides an inwardly directed radial force on the inner layer.

Example 172: The method according to any example herein, particularly example 170-171, where an outer jacket extends around the outer layer and provides an inwardly directed radial force on the outer layer.

Example 173: The method according to any example herein, particularly examples 170-172, wherein the tie layer extends between an outer surface of the overlapping (folded) portion of the inner layer and a corresponding surface of the overlapping portion of the outer layer, the tie layer adhering the inner layer to the outer layer.

Example 174: The method according to any example herein, particularly examples 170-173, wherein the tie layer does not extend between an inner surface of the overlapping folded portion of the inner layer and a corresponding surface of the underlying portion of the outer surface of the outer layer such that the outer layer and the inner layer are not adhered.

Example 175: The method according to any example herein, particularly examples 170-174, wherein expanding the outer layer along at least one gap further comprises expanding the gap over the overlapping portion.

Example 176: The method according to any example herein, particularly examples 170-175, further comprising expanding the inner layer into the gap.

Example 177: The method according to any example herein, particularly examples 170-176, further comprising merging the first and second folds and eliminating the overlapping portion at the local axial location.

Example 178: The method according to any example herein, particularly examples 170-177, expanding the inner layer at the local axial location into a substantially tubular, unfolded cross-section.

Example 179: The method according to any example herein, particularly examples 170-178, further comprising exerting a radial force on the gap of the outer layer and widening the outer layer along the gap.

Example 180: The method according to any example herein, particularly example 179, further comprising moving one of the folds closer to the gap during application of the radial force.

Example 181: The method according to any example herein, particularly example 180, wherein the gap is adjacent the first fold and further comprising passing the first fold radially under the gap as the first fold moves closer to the second fold.

Example 182: The method according to any example herein, particularly examples 170-181, wherein introducing the prosthetic device comprises introducing a stent-mounted heart valve into the proximal end of the lumen and further comprising extending the soft-tissue heart valve out of the distal end of the elongate lumen.

Example 183: The method according to any example herein, particularly example 182, further comprising expanding the stent-mounted heart valve after it exits the elongate lumen.

Example 184: The method according to any example herein, particularly examples 170-183, wherein a lubricant is provided between the outer jacket and the outer layer proximate a longitudinally extending edge of the overlapping portion, the lubricant reducing friction between the inner layer and the outer jacket during expansion of the sheath.

Example 185: An elastomeric jacket for an expandable and recoverable sheath including an axially reinforcing member embedded in an elastomeric jacket.

Example 186: The elastomeric jacket according to any example herein, particularly example 185, wherein the elastomeric jacket has an expansion force less than 50 N.

Example 187: The elastomeric jacket according to any example herein, particularly example 185-186, wherein the elastomeric jacket has a burst pressure greater than 8 psi.

Example 188: The elastomeric jacket according to any example herein, particularly examples 185-187, wherein the reinforcing member is constructed from a material having a Shore D durometer ranging from 45D to 76D.

Example 189: The elastomeric jacket according to any example herein, particularly examples 185-188, wherein the reinforcing member is constructed from high durometer polyether block amide, polyamide, or polyurethane.

Example 190: The elastomeric jacket according to any example herein, particularly examples 185-189, wherein the elastomeric jacket comprises at least one layer of material and at least one reinforcing member.

Example 191: The elastomeric jacket according to any example herein, particularly example 190, wherein the at least one reinforcing member is constructed from a material compatible with the at least one layer of the elastomeric jacket.

Example 192: The elastomeric jacket according to any example herein, particularly examples 185, wherein the reinforcing member comprised a thermally bondable member imbedded in the elastomeric jacket.

Example 193: The elastomeric jacket according to any example herein, particularly example 192, wherein the thermally bondable member is constructed from a polyolefin backbone material including at least one of LDPE (low-density polyethylene), LLDPE (linear low-density polyethylene), EVA (ethylene-vinyl acetate), HDPE (high-density polyethylene), a PP (polypropylene), or a polyolefin copolymer with grafted functional group including at least one of a maleic anhydride or an acrylic acid.

Example 194: The elastomeric jacket according to any example herein, particularly examples 192-193, wherein the thermally bondable member is fused to elastomeric jacket by at least one of heat or compression.

Example 195: The elastomeric jacket according to any example herein, particularly examples 185-194, wherein the reinforcing member reduces axial bunching of the elastomeric outer jacket during insertion into the patient's vasculature.

In view of the many possible examples to which the principles of the disclosed invention can be applied, it should be recognized that the illustrated examples are only preferred examples of the invention and should not be taken as limiting the scope of the invention. Rather, the scope of the invention is defined by the following claims. We therefore claim as our invention all that comes within the scope and spirit of these claims.

We claim:

1. A sheath for delivering a medical device, the sheath comprising:

a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer;

a discontinuous outer layer extending at least partially around the inner layer, the outer layer having an overlapping portion and an underlying portion, at least a portion of the folded portion of the inner layer is positioned between the overlapping portion and the underlying portion;

an adhesive layer is provided between the inner layer and the outer layer and at least partially adhering the inner layer to the outer layer; and an outer jacket extending around the outer layer, a wall thickness of the outer jacket is greater along a length of the outer jacket adjacent a proximal end of the sheath, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the medical device passes through the lumen.

2. The sheath of claim 1, wherein the wall thickness of the outer jacket varies along a length of the outer jacket.

3. The sheath of claim 1, wherein the sheath includes a tapered segment adjacent the proximal end of the sheath, wherein the thickness of the outer jacket is greater along the tapered segment.

4. The sheath of claim 1, wherein the outer jacket is bonded to the outer layer along a length of the outer layer between the proximal end and a distal end of the outer layer.

5. The sheath of claim 1, wherein the outer jacket includes an axially extending reinforcing member imbedded in the outer jacket for reducing axial bunching of the outer jacket during insertion into the patient's vasculature, the outer jacket including a first polymer layer and a second polymer layer, wherein the reinforcing member is constructed from a material having a Shore D durometer ranging from 45D to 76D, wherein the outer jacket has a burst pressure greater than 8 psi.

6. The sheath of claim 1, wherein the first fold is configured to move closer to the second fold to shorten the folded portion at a local axial location during passage of the medical device through the lumen, and wherein shortening of the folded portion corresponds with a local expansion of the lumen, wherein the inner layer extends through a longitudinally extending opening provided in the outer layer when the outer layer is expanded, wherein the longitudinally extending opening is provided between a longitudinally extending edge of the overlapping portion and a longitudinally extending edge of the underlying portion.

7. The sheath of claim 1, wherein the inner layer is composed of an etched PTFE, wherein unetched portions of the inner layer are provided along portions of the inner layer that contact an outer surface of the outer layer.

8. The sheath of claim 7, wherein unetched portions of the inner layer are provided along those locations excluding the adhesive layer, wherein a surface of the inner layer adjacent the underlying portion of the outer layer, when the sheath is not expanded, are unetched.

9. The sheath of any one of claim 1, wherein the adhesive layer extends at least partially around an outer surface of the inner layer.

10. The sheath of any one of claim 1, wherein the adhesive layer extends between the outer layer and the overlapping folded portion of the inner layer.

11. The sheath of claim 10, wherein the adhesive layer extends between an outer surface of the overlapping folded portion of the inner layer and a corresponding surface of the overlapping portion of the outer layer.

12. The sheath of claim 10, wherein the adhesive layer does not extend between an inner surface of the overlapping folded portion of the inner layer and a corresponding surface of the underlying portion of an outer surface of the outer layer.

13. A sheath for delivering a medical device, the sheath comprising:

a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer;

a discontinuous outer layer extending at least partially around the inner layer, the outer layer having an overlapping portion and an underlying portion, at least a portion of the folded portion of the inner layer is positioned between the overlapping portion and the underlying portion, at least a portion of the folded portion of the inner layer extends beyond a longitudinally extending edge of the overlapping portion and along an outer surface of the outer layer;

a tie layer provided between the inner layer and the outer layer and at least partially adhering the inner layer to the outer layer; and an outer jacket extending around the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the medical device passes through the lumen, wherein a lubricant is provided between the outer jacket and the outer layer, where the lubricant is provided on an outer surface of the outer layer proximate the longitudinally extending edge of the overlapping portion and along the portion the folded portion of the inner layer extending along the outer surface of the outer layer.

14. The sheath of claim 13, wherein the lubricant is provided along a portion of the outer surface of the outer layer adjacent the portion the folded portion of the inner layer extending along the outer surface of the outer layer.

15. The sheath of claim 13, wherein the lubricant is applied as a band around a portion of the circumference of the outer layer, the band of lubricant extending longitudinally along a length of the outer layer.

16. A method of delivering a prosthetic device through an expandable sheath, the method comprising;

advancing the prosthetic device through a lumen of an expandable sheath, the prosthetic device applying an outwardly directed radial force to a tubular inner layer of the expandable sheath, locally expanding the lumen of the sheath at a local axial location due to an outwardly directed radial force exerted by a prosthetic device against an inner surface of the lumen during advancement of the prosthetic device through the local axial location, wherein locally expanding the lumen comprises:

moving a first fold of the inner layer circumferentially closer to a second fold of the inner layer and shortening an overlapping folded portion of the inner layer extending circumferentially between the first and second folds; and expanding an outer layer along at least one elongate gap generally aligned with the axis of the lumen and positioned adjacent to at least one of the folds, wherein expanding the outer layer along at least one elongate gap comprises moving a first portion of the outer layer away from a second portion of the outer layer, wherein the at least one elongate gap is defined between the first and second portions, as the first fold moves closer to the second fold, wherein the inner layer and the outer layer are at least partially adhered via a tie layer extending therebetween, locally contracting the lumen of the sheath at least partially back to an unexpanded configuration as the prosthetic device passes through the lumen; and delivering the prosthetic device to a procedure site.

17. The method of claim 16, further comprising:

expanding the inner layer into the gap, merging the first and second folds and eliminating the overlapping folded portion at the local axial location, wherein expanding the outer layer along at least one gap further comprises expanding the gap over the overlapping folded portion of the inner layer, wherein the tie layer extends between an outer surface of the overlapping folded portion of the inner layer and a corresponding surface of the overlapping portion of the outer layer, the tie layer adhering the inner layer to the outer layer, wherein the tie layer does not extend between an inner surface of the overlapping folded portion of the inner layer and a corresponding surface of an underlying portion of the outer surface of the outer layer such that the outer layer and the inner layer are not adhered, wherein during expansion, the inner surface of the overlapping folded portion of the inner layer expands into the elongate gap of the outer layer.

18. A sheath for delivering a medical device, the sheath comprising:

a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer;

a discontinuous outer layer extending at least partially around the inner layer, the outer layer having an overlapping portion and an underlying portion, at least a portion of the folded portion of the inner layer is positioned between the overlapping portion and the underlying portion;

an adhesive layer is provided between the inner layer and the outer layer and at least partially adhering the inner layer to the outer layer; and an outer jacket extending around the outer layer, where the outer jacket is bonded to the outer layer along a length of the outer layer between a proximal and distal end of the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the medical device passes through the lumen.

19. A sheath for delivering a medical device, the sheath comprising:

a continuous inner layer defining a lumen therethrough, the inner layer including a first fold and a second fold and an overlapping folded portion extending circumferentially between the first and second folds, the folded portion comprising overlap in a radial direction of at least two thicknesses of the inner layer;

a discontinuous outer layer extending at least partially around the inner layer, the outer layer having an overlapping portion and an underlying portion, at least a portion of the folded portion of the inner layer is positioned between the overlapping portion and the underlying portion;

an adhesive layer is provided between the inner layer and the outer layer and at least partially adhering the inner layer to the outer layer; and an outer jacket extending around the outer layer, wherein at least a portion of the sheath is configured to locally expand from an unexpanded configuration in which the lumen has a first diameter to an expanded configuration in which the lumen has a second diameter larger than the first diameter due to an outwardly directed radial force exerted by a medical device against the inner layer, and then locally contract at least partially back to the unexpanded configuration as the medical device passes through the lumen, wherein the first fold is configured to move closer to the second fold to shorten the folded portion at a local axial location during passage of the medical device through the lumen, and wherein shortening of the folded portion corresponds with a local expansion of the lumen, wherein the inner layer extends through a longitudinally extending opening provided in the outer layer when the outer layer is expanded, wherein the longitudinally extending opening is provided between a longitudinally extending edge of the overlapping portion and a longitudinally extending edge of the underlying portion.

\* \* \* \* \*